United States Patent
Howarth

(10) Patent No.: US 10,526,379 B2
(45) Date of Patent: Jan. 7, 2020

(54) METHODS AND PRODUCTS FOR FUSION PROTEIN SYNTHESIS

(71) Applicant: OXFORD UNIVERSITY INNOVATION LIMITED, Oxford (GB)

(72) Inventor: Mark Howarth, Oxford (GB)

(73) Assignee: Oxford University Innovation Limited, Botley, Oxford (GB)

( * ) Notice: Subject to any disclaimer, the term of this patent is extended or adjusted under 35 U.S.C. 154(b) by 0 days.

(21) Appl. No.: 15/578,486

(22) PCT Filed: Jun. 3, 2016

(86) PCT No.: PCT/GB2016/051640
§ 371 (c)(1),
(2) Date: Nov. 30, 2017

(87) PCT Pub. No.: WO2016/193746
PCT Pub. Date: Dec. 8, 2016

(65) Prior Publication Data
US 2018/0244730 A1   Aug. 30, 2018

(30) Foreign Application Priority Data

Jun. 6, 2015 (GB) .................................. 1509782.7

(51) Int. Cl.
*C07K 14/31* (2006.01)
*C07K 1/04* (2006.01)
*C07K 14/315* (2006.01)

(52) U.S. Cl.
CPC ............ *C07K 14/3156* (2013.01); *C07K 1/04* (2013.01)

(58) Field of Classification Search
CPC .............................. C07K 14/3156; C07K 1/04
See application file for complete search history.

(56) References Cited

U.S. PATENT DOCUMENTS

| | | | |
|---|---|---|---|
| 4,336,173 A | 6/1982 | Ugelstad | |
| 6,936,252 B2 * | 8/2005 | Gilbert | A61K 39/092 424/184.1 |
| 7,632,515 B2 * | 12/2009 | Gilbert | A61K 39/092 424/184.1 |
| 7,648,708 B2 * | 1/2010 | Gilbert | A61K 39/092 424/184.1 |
| 7,713,534 B2 * | 5/2010 | Gilbert | A61K 39/092 424/184.1 |
| 2005/0276814 A1 * | 12/2005 | Gilbert | A61K 39/092 424/190.1 |
| 2011/0097360 A1 * | 4/2011 | Donati | C07K 14/3156 424/242.1 |
| 2011/0243976 A1 * | 10/2011 | Donati | A61K 39/092 424/190.1 |
| 2012/0259101 A1 * | 10/2012 | Tan | C07K 14/32 530/405 |
| 2013/0053544 A1 * | 2/2013 | Howarth | C07K 14/315 530/350 |
| 2014/0348868 A1 * | 11/2014 | Donati | A61K 39/092 424/190.1 |

FOREIGN PATENT DOCUMENTS

| | | |
|---|---|---|
| WO | 2011/098772 | 8/2011 |
| WO | 2012/127060 | 9/2012 |
| WO | 2012/142113 | 10/2012 |
| WO | 2014/201265 A1 | 12/2014 |
| WO | 2015/156870 A1 | 10/2015 |

OTHER PUBLICATIONS

Tettelin et al., 2001, Complete Genome Sequence of a Virulent Isolate of *Streptococcus* pneumonia, Science, 293: 498-506.*
Olson et al., 2013, Phylogenetic relationship and virulence inference of *Streptococcus anginosus* Group: curated annotation and whole-genome comparative analysis support distinct species designation, BMC Genomics, 14: 895-417.*
Dixon et al., "Nonenzymatic assembly of branched polyubiquitin chains for structural and biochemical studies," Bioorganic & Medicinal Chemistry, Pergamon, GB, vol. 21, No. 12, Mar. 15, 2013, pp. 3421-3429.
Fairhead et al., "SpyAvidin Hubs Enable Precise and Ultrastable Orthogonal Nanoassembly," Journal of the American Chemical Society, vol. 136, No. 35, Sep. 3, 2014, pp. 12355-12363.
Fierer et al., "SpyLigase peptide-peptide ligation polymerizes athbodies to enhance magnetic cancer cell capture," Proceedings of the National Academy of Sciences, vol. 111, No. 13, Mar. 17, 2014, pp. E1176-E1181.
Veggiani et al., "Superglue from bacteria: unbreakable bridges for protein nanotechnology," Trends in Biotechnology, Elsevier Publications, Cambridge, GB, vol. 32, No. 10, Aug. 26, 2014, pp. 506-512.
Hu et al., "Autocatalytic intramolecular isopeptide bond formation in Gram-positive bacterial pili: A QM/MM simulation," Journal of the American Chemical Society, American Chemical Society, US, vol. 133, No. 3, Jan. 26, 2011, pp. 178-485.

(Continued)

*Primary Examiner* — Amber D Steele
(74) *Attorney, Agent, or Firm* — McDonnell Boehnen Hulbert & Berghoff LLP

(57) ABSTRACT

A method of producing a fusion protein is provided. The method includes: a) contacting a first protein with a second protein under conditions that enable the formation of an isopeptide bond between said proteins to form a linked protein; and b) contacting the linked protein from (a) with a third protein under conditions that enable the formation of an isopeptide bond between said third protein and said linked protein to form a fusion protein. Peptide linkers and the use of orthogonal pairs of said linkers in the synthesis of fusion proteins are also provided. Recombinant proteins comprising said linkers, nucleic acid molecules encoding said proteins and linkers, vectors comprising said nucleic acid molecules and host cells comprising said vectors and nucleic acid molecules are also contemplated.

16 Claims, 18 Drawing Sheets
Specification includes a Sequence Listing.

(56) References Cited

OTHER PUBLICATIONS

Dasgupta et al., "Isopeptide Ligation Catalyzed by Quintessential Sortase A," Journal of Biological Chemistry, vol. 286, No. 27, Jul. 8, 2011, pp. 23996-24006.
Veggiani et al., "Programmable polyproteams built using twin peptide superglues," Proceedings of the National Academy of Sciences, vol. 113, No. 4, Jan. 19, 2016, pp. 1202-1207.
International Search Report and Written Opinion of International Searching Authority dated Aug. 31, 2016 for International Application No. PCT/GB2016/051640 filed Jun. 3, 2016, 16 pages.
Budzik, J.M., et al., "Intramolecular Amide Bonds Stabilize Pili on the Surface of Bacilli", Proc. Natl. Acad. Sci. USA, Nov. 24, 2009, vol. 106(47), pp. 19992-19997, doi:10.1073/pnas.0910887106.
Candi, E., et al., "Transglutaminase Cross-Linking Properties of the Small Proline-Rich 1 Family of Cornified Cell Envelope Proteins. Integration with Loricrin", J. Biol. Chem., Mar. 12, 1999, vol. 274(11), pp. 7226-7237.
Castañeda, C., et. al., "Nonenzymatic Assembly of Natural Polyubiquitin Chains of Any Linkage Composition and Isotopic Labeling Scheme", J. Am. Chem. Soc., Nov. 9, 2011, vol. 133(44), pp. 17855-17868, doi:10.1021/ja207220g.
El Mortaji, L., et al., "Stability and Assembly of Pilus Subunits of *Streptococcus* pneumoniae", J. Biol. Chem., Apr. 16, 2010, vol. 285(16), pp. 12405-12415, doi:10.1074/jbc.M109.082776.
Fairhead, M., et al., "Plug-and-Play Pairing Via Defined Divalent Streptavidins", J. Mol. Biol., Jan. 9, 2014, vol. 426(1), pp. 199-214, doi:10.1016/j.jmb.2013.09.016.
Forsgren, N., et al., "Two Intramolecular Isopeptide Bonds Are Identified in the Crystal Structure of the *Streptococcus* Gordonii Sspb C-Terminal Domain", J. Mol. Biol., Apr. 2, 2010, vol. 397(3), pp. 740-751, doi:10.1016/j.jmb.2010.01.065.
Hagan, R.M., et al., "NMR Spectroscopic and Theoretical Analysis of a Spontaneously Formed Lys-Asp Isopeptide Bond", Angew. Chem. Int. Ed., 2010, vol. 49, pp. 8421-8425, doi:10.1002/anie.201004340.
Kang, H.J., et al., "The Corynebacterium Diphtheriae Shaft Pilin Spaa is Built of Tandem Ig-Like Modules with Stabilizing Isopeptide and Disulfide Bonds", Proc. Natl. Acad. Sci. USA, Oct. 6, 2009, vol. 106(40), pp. 16967-16971, doi:10.1073/pnas.0906826106.
Kang, H.J, et al., "Intramolecular Isopeptide Bonds Give Thermodynamic and Proteolytic Stability to the Major Pilin Protein of *Streptococcus* Pyogenes", J. Biol. Chem., Jul. 31, 2009, vol. 284(31), pp. 20729-20737, doi:10.1074/jbc.M109.014514.
Kang, H.J., et al., "Intramolecular Isopeptide Bonds: Protein Crosslinks Built for Stress?", Trends Biochem. Sci., Apr. 2011, vol. 36(4), pp. 229-237, doi:10.1016/j.tibs.2010.09.007.
Kang, H.J., et al., "Stabilizing Isopeptide Bonds Revealed in Gram-Positive Bacterial Pilus Structure", Science, Dec. 7, 2007, vol. 318(5856), pp. 1625-1628, PubMed PMID: 18063798.
Kent, S.B., "Total Chemical Synthesis of Proteins", Chem. Soc. Rev., Feb. 2009, vol. 38(2), pp. 338-351, doi:10.1039/b700141j, Epub Sep. 16, 2008, Review.
Li, L. et al., "Structural Analysis and Optimization of the Covalent Association Between SpyCatcher and a Peptide Tag", J. Mol. Biol., Jan. 23, 2014, vol. 426(2), pp. 309-317, doi:10.1016/j.jmb.2013.10.021.
Modica, J.A., et al., "Modular Assembly of Protein Building Blocks to Create Precisely Defined Megamolecules", Chembiochem., Nov. 5, 2012, vol. 13(16), pp. 2331-2334, doi:10.1002/cbic.201200501.
Nylander, A., et al., "Structure of the C-Terminal Domain of the Surface Antigen SpaP from the Caries Pathogen *Streptococcus* Mutans", Acta Crystallogr. Sect F Struct. Biol. Cryst. Commun., Jan. 1, 2011, vol. 67(Pt 1), pp. 23-26, doi:10.1107/S174430911004443X.
Oke, M., et al., "The Scottish Structural Proteomics Facility: Targets, Methods and Outputs", J. Struct. Funct. Genomics, Jun. 2010, vol. 11(2), pp. 167-180, doi:10.1007/s10969-010-9090-y.
Pengo, P., et al., "Solid-Phase Preparation of Protein Complexes", J. Mol. Recognit., Nov.-Dec. 2010, vol. 23(6), pp. 551-558, doi:10.1002/jmr.1095.
Pointon, J.A., et al., "A Highly Unusual Thioester Bond in a Pilus Adhesin is Required for Efficient Host Cell Interaction", J. Biol. Chem., Oct. 29, 2010, vol. 285(44), pp. 33858-33866, doi:10.1074/jbc.M110.149385.
Rossi, E.A., et al., "Complex and Defined Biostructures with the Dock-and-Lock Method", Trends Pharmacol. Sci., Sep. 2012, vol. 33(9), pp. 474-481, doi:10.1016/j.tips.2012.06.001.
Russell, J., et al., "Defined Protein Conjugates as Signaling Agents in Immunoassays", Clin. Chem., Oct. 2004, vol. 50(10), pp. 1921-1929.
Strackharn, M., et al., "Nanoscale Arrangement of Proteins by Single-Molecule Cut-and-Paste", J. Am. Chem. Soc., Sep. 19, 2012, vol. 134(37), pp. 15193-15196.
Sun, F., et al., "Synthesis of Bioactive Protein Hydrogels by Genetically Encoded SpyTag-SpyCatcher Chemistry", Proc. Natl. Acad. Sci. USA, Aug. 5, 2015, vol. 111(31), pp. 11269-11274, doi:10.1073/pnas.1401291111.
Wikoff, W.R., et al., "Topologically Linked Protein Rings in the Bacteriophage HK97 Capsid", Science, Sep. 22, 2000, vol. 289(5487), pp. 2129-2133.
Wong, C.H., et al., "Orthogonality in Organic, Polymer, and Supramolecular Chemistry: From Merrifield to Click Chemistry", Chem. Commun. (Camb), Feb. 28, 2013, vol. 49(17), pp. 1679-1695, doi:10.1039/c2cc37316e.
Xiao, J., et al., "Synthesis of N-Terminally Linked Protein Dimers and Trimers by a Combined Native Chemical Ligation-CuAAC Click Chemistry Strategy", Org. Lett., Sep. 17, 2009, vol. 11(18), pp. 4144-4147, doi:10.1021/ol9016468.
Yang, X., et al., "Orthogonal Enzymatic Reactions for the Assembly of Proteins at Electrode Addresses", Langmuir, Jan. 6, 2009, vol. 25(1), pp. 338-344, doi:10.1021/la802618q.
Zakeri, B., et al., "Peptide Tag Forming a Rapid Covalent Bond to a Protein, Through Engineering a Bacterial Adhesin", Proc. Natl. Acad. Sci. USA, Mar. 20, 2012, vol. 109(12), pp. E690-E697, doi:10.1073/pnas.1115485109, Epub Feb. 24, 2012, PubMed PMID: 22366317.
Zhang, W.B., et al., "Controlling Macromolecular Topology with Genetically Encoded SpyTag-SpyCatcher Chemistry", J. Am. Chem. Soc., Sep. 18, 2013, vol. 135(37), pp. 13988-13997, doi:10.1021/ja4076452.
UK Search Report dated Mar. 24, 2016, received from the UK Intellectual Property Office, for Application No. GB1509782.7, pp. 1-5.
Presentation by Mark Howarth at University of Bristol, UK, on Dec. 3, 2014, "Bacterial Superglue, Spontaneous Amide Bond Formation, and Polymers to Fish for Cancer Cells".
Das, R., et al., "Macromolecular Modeling with Rosetta", Annual Review of Biochemistry, Jul. 2008, vol. 77, pp. 363-382, doi:10.1146/annurev.biochem.77.062906.171838. (Abstract only).
Izore, T., et al., "Structural Basis of Host Cell Recognition by the Pilus Adhesin from *Streptococcus* pneumoniae", Structure, Jan. 13, 2010, vol. 18(1), pp. 106-115, DOI:10.1016/j.str.2009.10.019.
Klán, P., et al., "Photoremovable Protecting Groups in Chemistry and Biology: Reaction Mechanisms and Efficacy" Chemical Reviews, Jan. 9, 2013, vol. 113(1), pp. 119-191, doi:10.1021/cr300177k, Epub Dec. 21, 2012.
Leriche, G., et al., "Cleavable Linkers in Chemical Biology", Bioorganic & Medicinal Chemistry, Jan. 15, 2012, vol. 20(2), pp. 571-582, doi:10.1016/j.bmc.2011.07.048, Epub Jul. 30, 2011. (Abstract only).
Li, J., et al., "Diels-Alder Reaction-Triggered Bioorthogonal Protein Decaging in Living Cells", Nature Chemical Biology, Dec. 2014, vol. 10(12), pp. 1003-1005, doi:10.1038/nchembio.1656, Epub Nov. 2, 2014. (Abstract only).

\* cited by examiner

A

B

C

D

A

B

A

B

A

B

A

B

SEQUENCE LISTING

```
<160> NUMBER OF SEQ ID NOS: 126

<210> SEQ ID NO 1
<211> LENGTH: 12
<212> TYPE: PRT
<213> ORGANISM: Artificial sequence
<220> FEATURE:
<223> OTHER INFORMATION: SnoopTag

<400> SEQUENCE: 1

Lys Leu Gly Asp Ile Glu Phe Ile Lys Val Asn Lys
1               5                   10

<210> SEQ ID NO 2
<211> LENGTH: 112
<212> TYPE: PRT
<213> ORGANISM: Artificial sequence
<220> FEATURE:
<223> OTHER INFORMATION: SnoopCatcher

<400> SEQUENCE: 2

Lys Pro Leu Arg Gly Ala Val Phe Ser Leu Gln Lys Gln His Pro Asp
1               5                   10                  15

Tyr Pro Asp Ile Tyr Gly Ala Ile Asp Gln Asn Gly Thr Tyr Gln Asn
                20                  25                  30

Val Arg Thr Gly Glu Asp Gly Lys Leu Thr Phe Lys Asn Leu Ser Asp
            35                  40                  45

Gly Lys Tyr Arg Leu Phe Glu Asn Ser Glu Pro Ala Gly Tyr Lys Pro
        50                  55                  60

Val Gln Asn Lys Pro Ile Val Ala Phe Gln Ile Val Asn Gly Glu Val
```

```
                65                  70                  75                  80
Arg Asp Val Thr Ser Ile Val Pro Gln Asp Ile Pro Ala Thr Tyr Glu
                    85                  90                  95

Phe Thr Asn Gly Lys His Tyr Ile Thr Asn Glu Pro Ile Pro Pro Lys
            100                 105                 110

<210> SEQ ID NO 3
<211> LENGTH: 36
<212> TYPE: DNA
<213> ORGANISM: Artificial sequence
<220> FEATURE:
<223> OTHER INFORMATION: SnoopTag

<400> SEQUENCE: 3
aaactgggcg atattgaatt tattaaagtg aacaaa                              36

<210> SEQ ID NO 4
<211> LENGTH: 336
<212> TYPE: DNA
<213> ORGANISM: Artificial sequence
<220> FEATURE:
<223> OTHER INFORMATION: SnoopCatcher

<400> SEQUENCE: 4
aagccgctgc gtggtgccgt gtttagcctg cagaaacagc atcccgacta tcccgatatc    60
tatggcgcga ttgatcagaa tgggacctat caaaatgtgc gtaccggcga agatggtaaa   120 ctgacccttta agaatctgag cgatggcaaa tatcgcctgt ttgaaaatag cgaacccgct   180
ggctataaac cggtgcagaa taagccgatt gtggcgtttc agattgtgaa tggcgaagtg   240
cgtgatgtga ccagcattgt gccgcaggat attccggcta catatgaatt taccaacggt   300
aaacattata tcaccaatga accgataccg ccgaaa                             336

<210> SEQ ID NO 5
<211> LENGTH: 13
<212> TYPE: PRT
<213> ORGANISM: Artificial sequence
<220> FEATURE:
<223> OTHER INFORMATION: PsCsTag

<400> SEQUENCE: 5

Gly Asn Lys Leu Thr Val Thr Asp Gln Ala Ala Pro Ser
1               5                   10

<210> SEQ ID NO 6
<211> LENGTH: 91
<212> TYPE: PRT
<213> ORGANISM: Artificial sequence
<220> FEATURE:
<223> OTHER INFORMATION: PsCsCatcher

<400> SEQUENCE: 6

Glu Gln Asp Val Val Phe Ser Lys Val Asn Val Ala Gly Glu Ile
1               5                   10                  15

Ala Gly Ala Lys Ile Gln Leu Lys Asp Ala Gln Gly Gln Val Val His
            20                  25                  30

Ser Trp Thr Ser Lys Ala Gly Gln Ser Glu Thr Val Lys Leu Lys Ala
        35                  40                  45

Gly Thr Tyr Thr Phe His Glu Ala Ser Ala Pro Thr Gly Tyr Leu Ala
    50                  55                  60

Val Thr Asp Ile Thr Phe Glu Val Asp Val Gln Gly Lys Val Thr Val
65                  70                  75                  80
```

```
Lys Asp Ala Asn Gly Asn Gly Val Lys Ala Asp
                85                  90
```

<210> SEQ ID NO 7
<211> LENGTH: 39
<212> TYPE: DNA
<213> ORGANISM: Artificial sequence
<220> FEATURE:
<223> OTHER INFORMATION: PsCsTag

<400> SEQUENCE: 7

```
ggcaacaaac tgaccgtgac cgatcaggcg gcgccgagc                              39
```

<210> SEQ ID NO 8
<211> LENGTH: 273
<212> TYPE: DNA
<213> ORGANISM: Artificial sequence
<220> FEATURE:
<223> OTHER INFORMATION: PsCsCatcher

<400> SEQUENCE: 8

```
gaacaggatg tggtgtttag caaagtgaat gtggctggcg aggaaattgc gggagcgaaa       60
attcagttga aagacgcgca gggccaggtg gtgcatagct ggaccagcaa agcgggccaa      120
agcgaaaccg tgaagctgaa agccggcacc tatacctttc atgaggcgag cgcaccgacc      180
ggctatctgg cggtgaccga tattaccttt gaagtggatg tgcagggcaa agttacagtg      240
aaagatgcga atggcaatgg tgtgaaagcg gat                                   273
```

<210> SEQ ID NO 9
<211> LENGTH: 19
<212> TYPE: PRT
<213> ORGANISM: Artificial sequence
<220> FEATURE:
<223> OTHER INFORMATION: RrgATag

<400> SEQUENCE: 9

```
Asp Ile Pro Ala Thr Tyr Glu Phe Thr Asn Asp Lys His Tyr Ile Thr
1               5                   10                  15

Asn Glu Pro
```

<210> SEQ ID NO 10
<211> LENGTH: 104
<212> TYPE: PRT
<213> ORGANISM: Artificial sequence
<220> FEATURE:
<223> OTHER INFORMATION: RrgACatcher

<400> SEQUENCE: 10

```
Lys Leu Gly Asp Ile Glu Phe Ile Lys Val Asn Lys Asn Asp Lys Lys
1               5                   10                  15

Pro Leu Arg Gly Ala Val Phe Ser Leu Gln Lys Gln His Pro Asp Tyr
                20                  25                  30

Pro Asp Ile Tyr Gly Ala Ile Asp Gln Asn Gly Thr Tyr Gln Asn Val
            35                  40                  45

Arg Thr Gly Glu Asp Gly Lys Leu Thr Phe Lys Asn Leu Ser Asp Gly
        50                  55                  60

Lys Tyr Arg Leu Phe Glu Asn Ser Glu Pro Ala Gly Tyr Lys Pro Val
65                  70                  75                  80

Gln Asn Lys Pro Ile Val Ala Phe Gln Ile Val Asn Gly Glu Val Arg
                85                  90                  95
```

Asp Val Thr Ser Ile Val Pro Gln
            100

<210> SEQ ID NO 11
<211> LENGTH: 57
<212> TYPE: DNA
<213> ORGANISM: Artificial sequence
<220> FEATURE:
<223> OTHER INFORMATION: RrgATag

<400> SEQUENCE: 11
gatattccgg ctacatatga atttaccaac gataaacatt atatcaccaa tgaaccg      57

<210> SEQ ID NO 12
<211> LENGTH: 312
<212> TYPE: DNA
<213> ORGANISM: Artificial sequence
<220> FEATURE:
<223> OTHER INFORMATION: RrgACatcher

<400> SEQUENCE: 12
aaactgggcg atattgaatt tattaaagtg aacaaaaacg ataaaaagcc gctgcgtggt      60
gccgtgttta gcctgcagaa acagcatccc gactatcccg atatctatgg cgcgattgat     120
cagaatggga cctatcaaaa tgtgcgtacc ggcgaagatg gtaaactgac ctttaagaat     180
ctgagcgatg gcaaatatcg cctgtttgaa aatagcgaac ccgctggcta taaaccggtg     240
cagaataagc cgattgtggc gtttcagatt gtgaatggcg aagtgcgtga tgtgaccagc     300
attgtgccgc ag                                                         312

<210> SEQ ID NO 13
<211> LENGTH: 13
<212> TYPE: PRT
<213> ORGANISM: Artificial sequence
<220> FEATURE:
<223> OTHER INFORMATION: SpyTag

<400> SEQUENCE: 13

Ala His Ile Val Met Val Asp Ala Tyr Lys Pro Thr Lys
1               5                   10

<210> SEQ ID NO 14
<211> LENGTH: 83
<212> TYPE: PRT
<213> ORGANISM: Artificial sequence
<220> FEATURE:
<223> OTHER INFORMATION: SpyCatcher

<400> SEQUENCE: 14

Asp Ser Ala Thr His Ile Lys Phe Ser Lys Arg Asp Glu Asp Gly Lys
1               5                   10                  15

Glu Leu Ala Gly Ala Thr Met Glu Leu Arg Asp Ser Ser Gly Lys Thr
            20                  25                  30

Ile Ser Thr Trp Ile Ser Asp Gly Gln Val Lys Asp Phe Tyr Leu Tyr
        35                  40                  45

Pro Gly Lys Tyr Thr Phe Val Glu Thr Ala Ala Pro Asp Gly Tyr Glu
    50                  55                  60

Val Ala Thr Ala Ile Thr Phe Thr Val Asn Glu Gln Gly Gln Val Thr
65                  70                  75                  80

Val Asn Gly

<210> SEQ ID NO 15

```
<211> LENGTH: 39
<212> TYPE: DNA
<213> ORGANISM: Artificial sequence
<220> FEATURE:
<223> OTHER INFORMATION: SpyTag

<400> SEQUENCE: 15
gcccacatcg tgatggtgga cgcctacaag ccgacgaag                    39

<210> SEQ ID NO 16
<211> LENGTH: 249
<212> TYPE: DNA
<213> ORGANISM: Artificial sequence
<220> FEATURE:
<223> OTHER INFORMATION: SpyCatcher

<400> SEQUENCE: 16
gatagtgcta cccatattaa attctcaaaa cgtgatgagg acggcaaaga gttagctggt    60
gcaactatgg agttgcgtga ttcatctggt aaaactatta gtacatggat ttcagatgga   120
caagtgaaag atttctacct gtatccagga aaatatacat tgtcgaaac cgcagcacca   180 gacggttatg aggtagcaac tgctattacc tttacagtta atgagcaagg tcaggttact   240
gtaaatggc                                                          249

<210> SEQ ID NO 17
<211> LENGTH: 16
<212> TYPE: PRT
<213> ORGANISM: Artificial sequence
<220> FEATURE:
<223> OTHER INFORMATION: Isopeptag

<400> SEQUENCE: 17

Thr Asp Lys Asp Met Thr Ile Thr Phe Thr Asn Lys Lys Asp Ala Glu
1               5                   10                  15

<210> SEQ ID NO 18
<211> LENGTH: 282
<212> TYPE: PRT
<213> ORGANISM: Artificial sequence
<220> FEATURE:
<223> OTHER INFORMATION: Pilin-C

<400> SEQUENCE: 18

Ala Thr Thr Val His Gly Glu Thr Val Val Asn Gly Ala Lys Leu Thr
1               5                   10                  15

Val Thr Lys Asn Leu Asp Leu Val Asn Ser Asn Ala Leu Ile Pro Asn
            20                  25                  30

Thr Asp Phe Thr Phe Lys Ile Glu Pro Asp Thr Thr Val Asn Glu Asp
        35                  40                  45

Gly Asn Lys Phe Lys Gly Val Ala Leu Asn Thr Pro Met Thr Lys Val
    50                  55                  60

Thr Tyr Thr Asn Ser Asp Lys Gly Gly Ser Asn Thr Lys Thr Ala Glu
65                  70                  75                  80

Phe Asp Phe Ser Glu Val Thr Phe Glu Lys Pro Gly Val Tyr Tyr Tyr
                85                  90                  95

Lys Val Thr Glu Glu Lys Ile Asp Lys Val Pro Gly Val Ser Tyr Asp
            100                 105                 110

Thr Thr Ser Tyr Thr Val Gln Val His Val Leu Trp Asn Glu Glu Gln
        115                 120                 125

Gln Lys Pro Val Ala Thr Tyr Ile Val Gly Tyr Lys Glu Gly Ser Lys
    130                 135                 140
```

```
Val Pro Ile Gln Phe Lys Asn Ser Leu Asp Ser Thr Thr Leu Thr Val
145                 150                 155                 160

Lys Lys Lys Val Ser Gly Thr Gly Gly Asp Arg Ser Lys Asp Phe Asn
                165                 170                 175

Phe Gly Leu Thr Leu Lys Ala Asn Gln Tyr Tyr Lys Ala Ser Glu Lys
            180                 185                 190

Val Met Ile Glu Lys Thr Thr Lys Gly Gly Gln Ala Pro Val Gln Thr
        195                 200                 205

Glu Ala Ser Ile Asp Gln Leu Tyr His Phe Thr Leu Lys Asp Gly Glu
    210                 215                 220

Ser Ile Lys Val Thr Asn Leu Pro Val Gly Val Asp Tyr Val Val Thr
225                 230                 235                 240

Glu Asp Asp Tyr Lys Ser Glu Lys Tyr Thr Thr Asn Val Glu Val Ser
                245                 250                 255

Pro Gln Asp Gly Ala Val Lys Asn Ile Ala Gly Asn Ser Thr Glu Gln
            260                 265                 270

Glu Thr Ser Thr Asp Lys Asp Met Thr Ile
            275                 280

<210> SEQ ID NO 19
<211> LENGTH: 48
<212> TYPE: DNA
<213> ORGANISM: Artificial sequence
<220> FEATURE:
<223> OTHER INFORMATION: Isopeptag

<400> SEQUENCE: 19
accgataaag atatgaccat tacctttacc aacaaaaaag atgcggaa          48

<210> SEQ ID NO 20
<211> LENGTH: 846
<212> TYPE: DNA
<213> ORGANISM: Artificial sequence
<220> FEATURE:
<223> OTHER INFORMATION: Pilin-C

<400> SEQUENCE: 20
gctacaacag ttcacgggga gactgttgta acggagcca aactaacagt tacaaaaaac      60
cttgatttag ttaatagcaa tgcattaatt ccaaatacag attttacatt taaaatcgaa    120
cctgatacta ctgtcaacga gacggaaat aagtttaaag gtgtagcttt gaacacaccg    180
atgactaaag tcacttacac caattcagat aaaggtggat caaatacgaa actgcagaa    240 tttgattttt cagaagttac tttttgaaaaa ccaggtgttt attattacaa agtaactgag    300
gagaagatag ataaagttcc tggtgtttct tatgatacaa catcttacac tgttcaagtt    360
catgtcttgt ggaatgaaga gcaacaaaaa ccagtagcta cttatattgt tggttataaa    420
gaaggtagta aggtgccaat tcagttcaaa aatagcttag attctactac attaacggtg    480
aagaaaaaag tttcaggtac cggtggagat cgctctaaag attttaattt tggtctgact    540
ttaaaagcaa atcagtatta taaggcgtca gaaaagtca tgattgagaa gacaactaaa    600
ggtggtcaag ctcctgttca acagaggct agtatagatc aactctatca ttttaccttg    660
aaagatggtg aatcaatcaa agtcacaaat cttccagtag gtgtggatta tgttgtcact    720
gaagacgatt acaaatcaga aaaatataca accaacgtgg aagttagtcc tcaagatgga    780
gctgtaaaaa atatcgcagg taattcaact gaacaagaga catctactga taaagatatg    840
accatt                                                              846
```

<210> SEQ ID NO 21
<211> LENGTH: 893
<212> TYPE: PRT
<213> ORGANISM: Streptococcus pneumoniae

<400> SEQUENCE: 21

Met Leu Asn Arg Glu Thr His Met Lys Lys Val Arg Lys Ile Phe Gln
1               5                   10                  15

Lys Ala Val Ala Gly Leu Cys Cys Ile Ser Gln Leu Thr Ala Phe Ser
            20                  25                  30

Ser Ile Val Ala Leu Ala Glu Thr Pro Glu Thr Ser Pro Ala Ile Gly
        35                  40                  45

Lys Val Val Ile Lys Glu Thr Gly Glu Gly Ala Leu Leu Gly Asp
    50                  55                  60

Ala Val Phe Glu Leu Lys Asn Asn Thr Asp Gly Thr Thr Val Ser Gln
65                  70                  75                  80

Arg Thr Glu Ala Gln Thr Gly Glu Ala Ile Phe Ser Asn Ile Lys Pro
                85                  90                  95

Gly Thr Tyr Thr Leu Thr Glu Ala Gln Pro Val Gly Tyr Lys Pro
            100                 105                 110

Ser Thr Lys Gln Trp Thr Val Glu Val Glu Lys Asn Gly Arg Thr Thr
        115                 120                 125

Val Gln Gly Glu Gln Val Glu Asn Arg Glu Glu Ala Leu Ser Asp Gln
    130                 135                 140

Tyr Pro Gln Thr Gly Thr Tyr Pro Asp Val Gln Thr Pro Tyr Gln Ile
145                 150                 155                 160

Ile Lys Val Asp Gly Ser Glu Lys Asn Gly Gln His Lys Ala Leu Asn
                165                 170                 175

Pro Asn Pro Tyr Glu Arg Val Ile Pro Glu Gly Thr Leu Ser Lys Arg
            180                 185                 190

Ile Tyr Gln Val Asn Asn Leu Asp Asp Asn Gln Tyr Gly Ile Glu Leu
        195                 200                 205

Thr Val Ser Gly Lys Thr Val Tyr Glu Gln Lys Asp Lys Ser Val Pro
    210                 215                 220

Leu Asp Val Val Ile Leu Leu Asp Asn Ser Asn Ser Met Ser Asn Ile
225                 230                 235                 240

Arg Asn Lys Asn Ala Arg Arg Ala Glu Arg Ala Gly Glu Ala Thr Arg
                245                 250                 255

Ser Leu Ile Asp Lys Ile Thr Ser Asp Ser Glu Asn Arg Val Ala Leu
            260                 265                 270

Val Thr Tyr Ala Ser Thr Ile Phe Asp Gly Thr Glu Phe Thr Val Glu
        275                 280                 285

Lys Gly Val Ala Asp Lys Asn Gly Lys Arg Leu Asn Asp Ser Leu Phe
    290                 295                 300

Trp Asn Tyr Asp Gln Thr Ser Phe Thr Thr Asn Thr Lys Asp Tyr Ser
305                 310                 315                 320

Tyr Leu Lys Leu Thr Asn Asp Lys Asn Asp Ile Val Glu Leu Lys Asn
                325                 330                 335

Lys Val Pro Thr Glu Ala Glu Asp His Asp Gly Asn Arg Leu Met Tyr
            340                 345                 350

Gln Phe Gly Ala Thr Phe Thr Gln Lys Ala Leu Met Lys Ala Asp Glu
        355                 360                 365

Ile Leu Thr Gln Gln Ala Arg Gln Asn Ser Gln Lys Val Ile Phe His

```
              370                 375                 380
Ile Thr Asp Gly Val Pro Thr Met Ser Tyr Pro Ile Asn Phe Asn His
385                 390                 395                 400

Ala Thr Phe Ala Pro Ser Tyr Gln Asn Gln Leu Asn Ala Phe Phe Ser
                    405                 410                 415

Lys Ser Pro Asn Lys Asp Gly Ile Leu Leu Ser Asp Phe Ile Thr Gln
                420                 425                 430

Ala Thr Ser Gly Glu His Thr Ile Val Arg Gly Asp Gly Gln Ser Tyr
            435                 440                 445

Gln Met Phe Thr Asp Lys Thr Val Tyr Glu Lys Gly Ala Pro Ala Ala
        450                 455                 460

Phe Pro Val Lys Pro Glu Lys Tyr Ser Glu Met Lys Ala Ala Gly Tyr
465                 470                 475                 480

Ala Val Ile Gly Asp Pro Ile Asn Gly Gly Tyr Ile Trp Leu Asn Trp
                    485                 490                 495

Arg Glu Ser Ile Leu Ala Tyr Pro Phe Asn Ser Asn Thr Ala Lys Ile
                500                 505                 510

Thr Asn His Gly Asp Pro Thr Arg Trp Tyr Tyr Asn Gly Asn Ile Ala
            515                 520                 525

Pro Asp Gly Tyr Asp Val Phe Thr Val Gly Ile Gly Ile Asn Gly Asp
        530                 535                 540

Pro Gly Thr Asp Glu Ala Thr Ala Thr Ser Phe Met Gln Ser Ile Ser
545                 550                 555                 560

Ser Lys Pro Glu Asn Tyr Thr Asn Val Thr Asp Thr Thr Lys Ile Leu
                    565                 570                 575

Glu Gln Leu Asn Arg Tyr Phe His Thr Ile Val Thr Glu Lys Lys Ser
                580                 585                 590

Ile Glu Asn Gly Thr Ile Thr Asp Pro Met Gly Glu Leu Ile Asp Leu
            595                 600                 605

Gln Leu Gly Thr Asp Gly Arg Phe Asp Pro Ala Asp Tyr Thr Leu Thr
        610                 615                 620

Ala Asn Asp Gly Ser Arg Leu Glu Asn Gly Gln Ala Val Gly Gly Pro
625                 630                 635                 640

Gln Asn Asp Gly Gly Leu Leu Lys Asn Ala Lys Val Leu Tyr Asp Thr
                    645                 650                 655

Thr Glu Lys Arg Ile Arg Val Thr Gly Leu Tyr Leu Gly Thr Asp Glu
                660                 665                 670

Lys Val Thr Leu Thr Tyr Asn Val Arg Leu Asn Asp Glu Phe Val Ser
            675                 680                 685

Asn Lys Phe Tyr Asp Thr Asn Gly Arg Thr Thr Leu His Pro Lys Glu
        690                 695                 700

Val Glu Gln Asn Thr Val Arg Asp Phe Pro Ile Pro Lys Ile Arg Asp
705                 710                 715                 720

Val Arg Lys Tyr Pro Glu Ile Thr Ile Ser Lys Glu Lys Lys Leu Gly
                    725                 730                 735

Asp Ile Glu Phe Ile Lys Val Asn Lys Asn Asp Lys Lys Pro Leu Arg
                740                 745                 750

Gly Ala Val Phe Ser Leu Gln Lys Gln His Pro Asp Tyr Pro Asp Ile
            755                 760                 765

Tyr Gly Ala Ile Asp Gln Asn Gly Thr Tyr Gln Asn Val Arg Thr Gly
        770                 775                 780

Glu Asp Gly Lys Leu Thr Phe Lys Asn Leu Ser Asp Gly Lys Tyr Arg
785                 790                 795                 800
```

```
Leu Phe Glu Asn Ser Glu Pro Ala Gly Tyr Lys Pro Val Gln Asn Lys
            805                 810                 815

Pro Ile Val Ala Phe Gln Ile Val Asn Gly Glu Val Arg Asp Val Thr
        820                 825                 830

Ser Ile Val Pro Gln Asp Ile Pro Ala Gly Tyr Glu Phe Thr Asn Asp
            835                 840                 845

Lys His Tyr Ile Thr Asn Glu Pro Ile Pro Lys Arg Glu Tyr Pro
        850                 855                 860

Arg Thr Gly Gly Ile Gly Met Leu Pro Phe Tyr Leu Ile Gly Cys Met
865                 870                 875                 880

Met Met Gly Gly Val Leu Leu Tyr Thr Arg Lys His Pro
            885                 890

<210> SEQ ID NO 22
<211> LENGTH: 2682
<212> TYPE: DNA
<213> ORGANISM: Streptococcus pneumoniae

<400> SEQUENCE: 22
```

| | | | | |
|---|---|---|---|---|
| atgctgaacc gcgaaaccca tatgaaaaaa gtaagaaaga tatttcagaa ggcagttgca | | | | 60 |
| ggactgtgct gtatatctca gttgacagct ttttcttcga tagttgcttt agcagaaacg | | | | 120 |
| cctgaaacca gtccagcgat aggaaaagta gtgattaagg agacaggcga aggaggagcg | | | | 180 |
| cttctaggag atgccgtctt tgagttgaaa acaatacgg atggcacaac tgtttcgcaa | | | | 240 |
| aggacagagg cgcaaacagg agaagcgata ttttcaaaca taaaacctgg acatacacc | | | | 300 |
| ttgacagaag cccaacctcc agttggttat aaaccctcta ctaaacaatg gactgttgaa | | | | 360 |
| gttgagaaga atggtcggac gactgtccaa ggtgaacagg tagaaaatcg agaagaggct | | | | 420 |
| ctatctgacc agtatccaca aacagggact tatccagatg ttcaaacacc ttatcagatt | | | | 480 |
| attaaggtag atggttcgga aaaaaacgga cagcacaagg cgttgaatcc gaatccatat | | | | 540 |
| gaacgtgtga ttccagaagg tacactttca agagaattt atcaagtgaa taatttggat | | | | 600 |
| gataaccaat atggaatcga attgacggtt agtgggaaaa cagtgtatga acaaaaagat | | | | 660 |
| aagtctgtgc cgctggatgt cgttatcttg ctcgataact caaatagtat gagtaacatt | | | | 720 |
| cgaaacaaga atgctcgacg tgcggaaaga gctggtgagg cgacacgttc tcttattgat | | | | 780 |
| aaaattacat ctgattcaga aaatagggta gcgcttgtga cttatgcttc cactatcttt | | | | 840 |
| gatgggaccg agtttacagt agaaaaaggg gtagcagata aaacggaaa gcgattgaat | | | | 900 |
| gattctcttt tttggaatta tgatcagacg agttttacaa ccaataccaa agattatagt | | | | 960 |
| tatttaaagc tgactaatga taagaatgac attgtagaat taaaaaataa ggtacctacc | | | | 1020 |
| gaggcagaag accatgatgg aaatagattg atgtaccaat tcggtgccac ttttactcag | | | | 1080 |
| aaagctttga tgaaggcaga tgagattttg acacaacaag cgagacaaaa tagtcaaaaa | | | | 1140 |
| gtcattttcc atattacgga tggtgtccca actatgtcgt atccgattaa ttttaatcat | | | | 1200 |
| gctacgtttg ctccatcata tcaaaatcaa ctaaatgcat ttttagtaa atctcctaat | | | | 1260 |
| aaagatggaa tactattaag tgattttatt acgcaagcaa ctagtggaga acatacaatt | | | | 1320 |
| gtacgcggag atgggcaaag ttaccagatg tttacagata agacagttta tgaaaaaggt | | | | 1380 |
| gctcctgcag ctttcccagt aaacctgaa aaatattctg aaatgaaggc ggctggttat | | | | 1440 |
| gcagttatag cgatccaat taatggtgga tatatttggc ttaattggag agagagtatt | | | | 1500 |
| ctggcttatc cgtttaattc taatactgct aaaattacca atcatggtga ccctacaaga | | | | 1560 |

```
tggtactata acgggaatat tgctcctgat gggtatgatg tctttacggt aggtattggt    1620
attaacggag atcctggtac ggatgaagca acggctacta gttttatgca aagtatttct    1680
agtaaacctg aaaactatac caatgttact gacacgacaa aaatattgga acagttgaat    1740
cgttatttcc acaccatcgt aactgaaaag aaatcaattg agaatggtac gattacagat    1800
ccgatgggtg agttaattga tttgcaattg gcacagatg gaagatttga tccagcagat    1860
tacactttaa ctgcaaacga tggtagtcgc ttggagaatg acaagctgt aggtggtcca    1920 caaaatgatg gtggttttgtt aaaaaatgca aaagtgctct atgatacgac tgagaaaagg    1980
attcgtgtaa caggtctgta ccttggaacg gatgaaaaag ttacgttgac ctacaatgtt    2040
cgtttgaatg atgagtttgt aagcaataaa ttttatgata ccaatggtcg aacaacctta    2100
catcctaagg aagtagaaca gaacacagtg cgcgacttcc cgattcctaa gattcgtgat    2160
gtgcggaagt atccagaaat cacaatttca aaagagaaaa aacttggtga cattgagttt    2220
attaaggtca ataaaaatga taaaaaacca ctgagaggtg cggtctttag tcttcaaaaa    2280
caacatccgg attatccaga tatttatgga gctattgatc aaaatggcac ttatcaaaat    2340
gtgagaacag gtgaagatgg taagttgacc tttaaaaatc tgtcagatgg gaaatatcga    2400
ttatttgaaa attctgaacc agctggttat aaacccgttc aaaataagcc tatcgttgcc    2460
ttccaaatag taaatggaga agtcagagat gtgacttcaa tcgttccaca agatatacca    2520
gcgggttacg agtttacgaa tgataagcac tatattacca atgaacctat tcctccaaag    2580
agagaatatc ctcgaactgg tggtatcgga atgttgccat tctatctgat aggttgcatg    2640
atgatgggag gagttctatt atacacacgg aaacatccgt aa                       2682
```

<210> SEQ ID NO 23
<211> LENGTH: 340
<212> TYPE: PRT
<213> ORGANISM: Streptococcus pyogenes

<400> SEQUENCE: 23

```
Met Lys Leu Arg His Leu Leu Thr Gly Ala Ala Leu Thr Ser Phe
1               5                   10                  15

Ala Ala Thr Thr Val His Gly Glu Thr Val Val Asn Gly Ala Lys Leu
            20                  25                  30

Thr Val Thr Lys Asn Leu Asp Leu Val Asn Ser Asn Ala Leu Ile Pro
        35                  40                  45

Asn Thr Asp Phe Thr Phe Lys Ile Glu Pro Asp Thr Thr Val Asn Glu
    50                  55                  60

Asp Gly Asn Lys Phe Lys Gly Val Ala Leu Asn Thr Pro Met Thr Lys
65                  70                  75                  80

Val Thr Tyr Thr Asn Ser Asp Lys Gly Gly Ser Asn Thr Lys Thr Ala
                85                  90                  95

Glu Phe Asp Phe Ser Glu Val Thr Phe Glu Lys Pro Gly Val Tyr Tyr
            100                 105                 110

Tyr Lys Val Thr Glu Glu Lys Ile Asp Lys Val Pro Gly Val Ser Tyr
        115                 120                 125

Asp Thr Thr Ser Tyr Thr Val Gln Val His Val Leu Trp Asn Glu Glu
    130                 135                 140

Gln Gln Lys Pro Val Ala Thr Tyr Ile Val Gly Tyr Lys Glu Gly Ser
145                 150                 155                 160

Lys Val Pro Ile Gln Phe Lys Asn Ser Leu Asp Ser Thr Thr Leu Thr
                165                 170                 175
```

Val Lys Lys Lys Val Ser Gly Thr Gly Gly Asp Arg Ser Lys Asp Phe
            180                 185                 190

Asn Phe Gly Leu Thr Leu Lys Ala Asn Gln Tyr Tyr Lys Ala Ser Glu
        195                 200                 205

Lys Val Met Ile Glu Lys Thr Thr Lys Gly Gly Gln Ala Pro Val Gln
            210                 215                 220

Thr Glu Ala Ser Ile Asp Gln Leu Tyr His Phe Thr Leu Lys Asp Gly
225                 230                 235                 240

Glu Ser Ile Lys Val Thr Asn Leu Pro Val Gly Val Asp Tyr Val Val
                245                 250                 255

Thr Glu Asp Asp Tyr Lys Ser Glu Lys Tyr Thr Thr Asn Val Glu Val
            260                 265                 270

Ser Pro Gln Asp Gly Ala Val Lys Asn Ile Ala Gly Asn Ser Thr Glu
        275                 280                 285

Gln Glu Thr Ser Thr Asp Lys Asp Met Thr Ile Thr Phe Thr Asn Lys
    290                 295                 300

Lys Asp Phe Glu Val Pro Thr Gly Val Ala Met Thr Val Ala Pro Tyr
305                 310                 315                 320

Ile Ala Leu Gly Ile Val Ala Val Gly Gly Ala Leu Tyr Phe Val Lys
                325                 330                 335

Lys Lys Asn Ala
        340

<210> SEQ ID NO 24
<211> LENGTH: 1023
<212> TYPE: DNA
<213> ORGANISM: Streptococcus pyogenes

<400> SEQUENCE: 24

```
atgaaattac gtcacttact attaacggga gcagccctaa ctagttttgc tgctacaaca      60
gttcacgggg agactgttgt aaacggagcc aaactaacag ttacaaaaaa ccttgattta     120
gttaatagca atgcattaat tccaaataca gattttacat ttaaaatcga acctgatact     180
actgtcaacg aagacggaaa taagtttaaa ggtgtagctt tgaacacacc gatgactaaa     240
gtcacttaca ccaattcaga taaaggtgga tcaaatacga aaactgcaga atttgatttt     300
tcagaagtta cttttgaaaa accaggtgtt tattattaca agtaactga ggagaagata      360
gataaagttc ctggtgtttc ttatgataca acatcttaca ctgttcaagt tcatgtcttg     420
tggaatgaag agcaacaaaa accagtagct acttatattg ttggttataa agaaggtagt     480
aaggtgccaa ttcagttcaa aaatagctta gattctacta cattaacggt gaagaaaaaa     540
gtttcaggta ccggtggaga tcgctctaaa gattttaatt ttggtctgac tttaaaagca     600
aatcagtatt ataaggcgtc agaaaaagtc atgattgaga agacaactaa aggtggtcaa     660
gctcctgttc aaacagaggc tagtatagat caactctatc attttacctt gaaagatggt     720
gaatcaatca agtcacaaa tcttccagta ggtgtggatt atgttgtcac tgaagacgat     780
tacaaatcag aaaaatatac aaccaacgtg aagttagtc ctcaagatgg agctgtaaaa     840
aatatcgcag gtaattcaac tgaacaagag acatctactg ataaagatat gaccattact     900
tttacaaata aaaaagactt tgaagtgcca acaggagtag caatgactgt ggcaccatat     960
attgctttag gaattgtagc agttggtgga gctctttact tgttaaaaaa gaaaaatgct    1020
taa                                                                  1023
```

<210> SEQ ID NO 25

<211> LENGTH: 102
<212> TYPE: PRT
<213> ORGANISM: Streptococcus pyogenes

<400> SEQUENCE: 25

```
Met Thr Ile Glu Glu Asp Ser Ala Thr His Ile Lys Phe Ser Lys Arg
1               5                   10                  15

Asp Ile Asp Gly Lys Glu Leu Ala Gly Ala Thr Met Glu Leu Arg Asp
            20                  25                  30

Ser Ser Gly Lys Thr Ile Ser Thr Trp Ile Ser Asp Gly Gln Val Lys
        35                  40                  45

Asp Phe Tyr Leu Met Pro Gly Lys Tyr Thr Phe Val Glu Thr Ala Ala
    50                  55                  60

Pro Asp Gly Tyr Glu Val Ala Thr Ala Ile Thr Phe Thr Val Asn Glu
65                  70                  75                  80

Gln Gly Gln Val Thr Val Asn Gly Lys Ala Thr Lys Gly Asp Ala His
                85                  90                  95

Ile Val Met Val Asp Ala
            100
```

<210> SEQ ID NO 26
<211> LENGTH: 309
<212> TYPE: DNA
<213> ORGANISM: Streptococcus pyogenes

<400> SEQUENCE: 26

```
atgacaattg aagaagatag tgctacccat attaaattct caaaacgtga tattgacggc      60
aaagagttag ctggtgcaac tatggagttg cgtgattcat ctggtaaaac tattagtaca     120
tggatttcag atggacaagt gaaagatttc tacctgatgc aggaaaata tacatttgtc     180 gaaaccgcag caccagacgg ttatgaggta gcaactgcta ttacctttac agttaatgag     240
caaggtcagg ttactgtaaa tggcaaagca actaaaggtg acgctcatat tgtcatggtt     300
gatgcttga                                                             309
```

<210> SEQ ID NO 27
<211> LENGTH: 674
<212> TYPE: PRT
<213> ORGANISM: Enterococcus faecalis

<400> SEQUENCE: 27

```
Met Thr Lys Ser Val Lys Phe Leu Val Leu Leu Val Met Ile Leu
1               5                   10                  15

Pro Ile Ala Gly Ala Leu Leu Ile Gly Pro Ile Ser Phe Gly Ala Glu
            20                  25                  30

Leu Ser Lys Ser Ser Ile Val Asp Lys Val Glu Leu Asp His Thr Thr
        35                  40                  45

Leu Tyr Gln Gly Glu Met Thr Ser Ile Lys Val Ser Phe Ser Asp Lys
    50                  55                  60

Glu Asn Gln Lys Ile Lys Pro Gly Asp Thr Ile Thr Leu Thr Leu Pro
65                  70                  75                  80

Asp Ala Leu Val Gly Met Thr Glu Asn Asp Ser Ser Pro Arg Lys Ile
                85                  90                  95

Asn Leu Asn Gly Leu Gly Glu Val Phe Ile Tyr Lys Asp His Val Val
            100                 105                 110

Ala Thr Phe Asn Glu Lys Val Glu Ser Leu His Asn Val Asn Gly His
        115                 120                 125
```

```
Phe Ser Phe Gly Ile Lys Thr Leu Ile Thr Asn Ser Ser Gln Pro Asn
    130                 135                 140

Val Ile Glu Thr Asp Phe Gly Thr Ala Thr Ala Thr Gln Arg Leu Thr
145                 150                 155                 160

Ile Glu Gly Val Thr Asn Thr Glu Thr Gly Gln Ile Glu Arg Asp Tyr
                    165                 170                 175

Pro Phe Phe Tyr Lys Val Gly Asp Leu Ala Gly Glu Ser Asn Gln Val
                180                 185                 190

Arg Trp Phe Leu Asn Val Asn Leu Asn Lys Ser Asp Val Thr Glu Asp
            195                 200                 205

Ile Ser Ile Ala Asp Arg Gln Gly Ser Gly Gln Gln Leu Asn Lys Glu
210                 215                 220

Ser Phe Thr Phe Asp Ile Val Asn Asp Lys Glu Thr Lys Tyr Ile Ser
225                 230                 235                 240

Leu Ala Glu Phe Glu Gln Gln Gly Tyr Gly Lys Ile Asp Phe Val Thr
                245                 250                 255

Asp Asn Asp Phe Asn Leu Arg Phe Tyr Arg Asp Lys Ala Arg Phe Thr
            260                 265                 270

Ser Phe Ile Val Arg Tyr Thr Ser Thr Ile Thr Glu Ala Gly Gln His
        275                 280                 285

Gln Ala Thr Phe Glu Asn Ser Tyr Asp Ile Asn Tyr Gln Leu Asn Asn
290                 295                 300

Gln Asp Ala Thr Asn Glu Lys Asn Thr Ser Gln Val Lys Asn Val Phe
305                 310                 315                 320

Val Glu Gly Glu Ala Ser Gly Asn Gln Asn Val Glu Met Pro Thr Glu
                325                 330                 335

Glu Ser Leu Asp Ile Pro Leu Glu Thr Ile Asp Glu Trp Glu Pro Lys
            340                 345                 350

Thr Pro Thr Ser Glu Gln Ala Thr Glu Thr Ser Glu Lys Thr Asp Thr
        355                 360                 365

Thr Glu Thr Ala Glu Ser Ser Gln Pro Glu Val His Val Ser Pro Thr
    370                 375                 380

Glu Glu Glu Asn Pro Asp Glu Gly Glu Thr Leu Gly Thr Ile Glu Pro
385                 390                 395                 400

Ile Ile Pro Glu Lys Pro Ser Val Thr Thr Glu Glu Asn Gly Thr Thr
                405                 410                 415

Glu Thr Ala Glu Ser Ser Gln Pro Glu Val His Val Ser Pro Thr Glu
            420                 425                 430

Glu Glu Asn Pro Asp Glu Ser Glu Thr Leu Gly Thr Ile Glu Pro Ile
        435                 440                 445

Ile Pro Glu Lys Pro Ser Val Thr Thr Glu Glu Asn Gly Thr Thr Glu
450                 455                 460

Thr Ala Glu Ser Ser Gln Pro Glu Val His Val Ser Pro Ala Glu Glu
465                 470                 475                 480

Glu Asn Pro Asp Glu Ser Glu Thr Leu Gly Thr Ile Leu Pro Ile Leu
                485                 490                 495

Pro Glu Lys Pro Ser Val Thr Thr Glu Glu Asn Gly Thr Thr Glu Thr
            500                 505                 510

Ala Glu Ser Ser Gln Pro Glu Val His Val Ser Pro Thr Glu Glu Glu
        515                 520                 525

Asn Pro Asp Glu Ser Glu Thr Leu Gly Thr Ile Ala Pro Ile Ile Pro
530                 535                 540

Glu Lys Pro Ser Val Thr Thr Glu Glu Asn Gly Ile Thr Glu Thr Ala
```

```
                545                 550                 555                 560
Glu Ser Ser Gln Pro Glu Val His Val Ser Pro Thr Lys Glu Ile Thr
                565                 570                 575
Thr Thr Glu Lys Lys Gln Pro Ser Thr Glu Thr Thr Val Glu Lys Asn
                580                 585                 590
Lys Asn Val Thr Ser Lys Asn Gln Pro Gln Ile Leu Asn Ala Pro Leu
                595                 600                 605
Asn Thr Leu Lys Asn Glu Gly Ser Pro Gln Leu Ala Pro Gln Leu Leu
        610                 615                 620
Ser Glu Pro Ile Gln Lys Leu Asn Glu Ala Asn Gly Gln Arg Glu Leu
625                 630                 635                 640
Pro Lys Thr Gly Thr Thr Lys Thr Pro Phe Met Leu Ile Ala Gly Ile
                645                 650                 655
Leu Ala Ser Thr Phe Ala Val Leu Gly Val Ser Tyr Leu Gln Ile Arg
                660                 665                 670
Lys Asn

<210> SEQ ID NO 28
<211> LENGTH: 2025
<212> TYPE: DNA
<213> ORGANISM: Enterococcus faecalis

<400> SEQUENCE: 28
atgacaaaaa gtgtaaaatt tttagtgtta ctgttggtaa tgattctacc aattgcgggg    60
gcgttattga ttggtccaat tcgtttggc gccgaattga gcaaaagttc aatcgttgac   120
aaagtagaat tagatcacac tactttatat caaggagaga tgacctcaat taaagtatct   180
tttagtgaca agaaaatca gaaaataaaa cctggagata ctattacttt aactttacca   240
gacgcactag ttggaatgac cgagaacgat agttcaccac gaaaaatcaa tttaaatggt   300
ttaggggaag ttttttatcta taaagatcat gttgtagcaa catttaacga aaaagttgaa   360
tctttacata atgtgaatgg gcattttct ttcgggatta aaacgcttat caccaatagt   420
tctcaaccga atgtgataga acgggattc ggaacagcaa cggcgactca acgtttgacg   480
attgaaggag tgactaacac agagactggc caaattgagc gagactatcc gttttttat   540 aaagtaggcg atttggctgg agagtcaaat caagtacgtt ggttttaaa tgtgaacctc   600 aataatccg atgtcacaga agatatttca attgcggatc gacaaggaag tggtcaacaa   660 ttaataaag agagttttac atttgatatt gtgaatgaca agaaactaa atatatttca   720 cttgccgagt ttgagcaaca aggttatggc aaaattgact cgtaacaga taatgacttt   780 aacttacgtt tttatcggga taaagcacgc tttacttcct ttatcgtccg ttacacttcg   840
acaatcacag aagcaggcca acatcaagca acatttgaaa atagttatga catcaattat   900
caactaaaca atcaagacgc aacgaatgaa aaaaatacat cacaggttaa aatgttttt   960 gtagaaggcg aggcaagcgg caatcaaaat gtggaaatgc aacagaaga agtctagac  1020 attcctttag acaatataga tgaatgggaa ccaaagacac ctacttcgga acaggcaaca  1080
gaaacaagtg aaaagacaga cacaacagaa accgcagaaa gcagccaacc agaagttcat  1140
gtctcaccaa cagaagaaga aaatccagat gaaggtaaa cactaggcac gattgagcca  1200 atcataccg aaaaaccag tgtgacaact gaagagaatg cacgacaga aactgcagaa  1260 agcagccaac cagaagttca tgtctcacca acagaagaag aaaatccaga tgaaagtgaa  1320
acactaggca cgattgagcc aatcataccg gaaaaaccaa gtgtgacaac tgaagagaac  1380
```

```
ggcacaacag aaaccgcaga aagcagccaa ccagaagttc atgtctcacc agcggaagaa    1440
gaaaatccag atgaaagtga aacgttaggt acaattttac caatcctacc tgaaaaacca    1500
agtgtgacaa ctgaagagaa tggcacaacg gaaactgcag aaagcagtca accagaagtc    1560
catgtgtcgc caacggaaga agaaaatcca gatgaaagtg aaacactagg cacgattgca    1620
ccaatcatac ctgaaaaacc aagcgtaaca actgaagaga atggtataac ggaaacggca    1680
gaaagcagcc agccagaagt tcatgtctca ccaacaaaag aaattactac aactgagaaa    1740
aaacagccat ccacagaaac aactgtggag aaaaataaaa atgttacatc aaaaaatcaa    1800
ccacaaatac taaacgctcc attaaataca ttgaaaaatg aaggaagccc acagttggct    1860
ccccaactgc ttagtgaacc aattcaaaaa ttaaatgaag caaacgggca acgagaactt    1920
cccaaaacag gcacaacaaa aacaccgttt atgctaatag caggaatact ggcaagtaca    1980
tttgccgttt taggtgtaag ttatctacaa atcagaaaga attaa                    2025
```

<210> SEQ ID NO 29
<211> LENGTH: 331
<212> TYPE: PRT
<213> ORGANISM: Staphylococcus aureus

<400> SEQUENCE: 29

```
Met Asn Lys Asn Val Leu Lys Phe Met Val Phe Ile Met Leu Leu Asn
1               5                   10                  15

Ile Ile Thr Pro Leu Phe Asn Lys Glu Ala Phe Ala Ala Arg Asp
            20                  25                  30

Ile Ser Ser Thr Asn Val Thr Asp Leu Thr Val Ser Pro Ser Lys Ile
            35                  40                  45

Glu Asp Gly Gly Lys Thr Thr Val Lys Met Thr Phe Asp Asp Lys Asn
50                  55                  60

Gly Lys Ile Gln Asn Gly Asp Met Ile Lys Val Ala Trp Pro Thr Ser
65                  70                  75                  80

Gly Thr Val Lys Ile Glu Gly Tyr Ser Lys Thr Val Pro Leu Thr Val
                85                  90                  95

Lys Gly Glu Gln Val Gly Gln Ala Val Ile Thr Pro Asp Gly Ala Thr
            100                 105                 110

Ile Thr Phe Asn Asp Lys Val Glu Lys Leu Ser Asp Val Ser Gly Phe
        115                 120                 125

Ala Glu Phe Glu Val Gln Gly Arg Asn Leu Thr Gln Thr Asn Thr Ser
130                 135                 140

Asp Asp Lys Val Ala Thr Ile Thr Ser Gly Asn Lys Ser Thr Asn Val
145                 150                 155                 160

Thr Val His Lys Ser Glu Ala Gly Thr Ser Ser Val Phe Tyr Tyr Lys
                165                 170                 175

Thr Gly Asp Met Leu Pro Glu Asp Thr Thr His Val Arg Trp Phe Leu
            180                 185                 190

Asn Ile Asn Asn Glu Lys Ser Tyr Val Ser Lys Asp Ile Thr Ile Lys
        195                 200                 205

Asp Gln Ile Gln Gly Gly Gln Gln Leu Asp Leu Ser Thr Leu Asn Ile
210                 215                 220

Asn Val Thr Gly Thr His Ser Asn Tyr Tyr Ser Gly Gln Ser Ala Ile
225                 230                 235                 240

Thr Asp Phe Glu Lys Ala Phe Pro Gly Ser Lys Ile Thr Val Asp Asn
                245                 250                 255

Thr Lys Asn Thr Ile Asp Val Thr Ile Pro Gln Gly Tyr Gly Ser Tyr
```

```
                260                 265                 270
Asn Ser Phe Ser Ile Asn Tyr Lys Thr Lys Ile Thr Asn Glu Gln Gln
            275                 280                 285

Lys Glu Phe Val Asn Asn Ser Gln Ala Trp Tyr Gln Glu His Gly Lys
        290                 295                 300

Glu Glu Val Asn Gly Lys Ser Phe Asn His Thr Val His Asn Ile Asn
305                 310                 315                 320

Ala Asn Ala Gly Ile Glu Gly Thr Val Lys Gly
                325                 330

<210> SEQ ID NO 30
<211> LENGTH: 993
<212> TYPE: DNA
<213> ORGANISM: Staphylococcus aureus

<400> SEQUENCE: 30
atgaacaaaa atgtgttgaa gtttatggtc tttataatgt tattaaatat catcacacct      60
ttatttaata aaaatgaagc atttgcagca cgagatattt catcaacgaa tgttacagat     120
ttaactgtat caccgtctaa gatagaagat ggtggtaaaa cgacagtaaa aatgacgttc     180
gacgataaaa atggaaaaat acaaaatggt gacatgatta agtggcatg gccgacaagc      240 ggtacagtaa agatagaggg ttatagtaaa acagtaccat taactgttaa aggtgaacag     300
gtgggtcaag cagttattac accagacggt gcaacaatta cattcaatga taaagtagaa     360
aaattaagtg atgtttcggg atttgcagaa tttgaagtac aaggaagaaa tttaacgcaa     420
acaaatactt cagatgacaa agtagctacg ataacatctg gaataaaatc aacgaatgtt     480
acggttcata aaagtgaagc gggaacaagt agtgttttct attataaaac gggagatatg     540
ctaccagaag atacgacaca tgtacgatgg ttttttaaata ttaacaatga aaaaagttat     600
gtatcgaaag atattactat aaaggatcag attcaaggtg acagcagtt agatttaagc      660 acattaaaca ttaatgtgac aggtacacat agcaattatt atagtggaca aagtgcaatt     720
actgattttg aaaaagcctt tccaggttct aaaataactg ttgataatac gaagaacaca     780
attgatgtaa caattccaca aggctatggg tcatataata gttttttcaat taactacaaa     840 accaaaatta cgaatgaaca gcaaaaagag tttgttaata attcacaagc ttggtatcaa     900
gagcatggta aggaagaagt gaacgggaaa tcatttaatc atactgtgca caatattaat     960
gctaatgccg gtattgaagg tactgtaaaa ggt                                   993

<210> SEQ ID NO 31
<211> LENGTH: 738
<212> TYPE: PRT
<213> ORGANISM: Streptococcus intermedius

<400> SEQUENCE: 31

Met Lys Lys Arg Arg Gly Gln Phe Phe Lys Ser Ala Ile Ser Phe Leu
1               5                   10                  15

Val Val Phe Leu Met Val Met Val Ser Ile Ile Tyr Pro Ser Ser Lys
            20                  25                  30

Ile Lys Ala Asp Gly Phe Pro Asn Asp Ala Thr Gly Val Ser Pro Asn
        35                  40                  45

Gly Lys Tyr Tyr Ser Ala Gly Arg Glu Asn Arg Leu Gly Met Val Thr
    50                  55                  60

Ser Asp Glu Leu His Thr Ala Thr Glu Leu Phe Gly Phe Cys Met Ala
65                  70                  75                  80
```

```
Asn Ser Lys Lys Tyr Pro Gly Tyr Asp Ser Lys Lys Asp Glu Tyr Phe
                85                  90                  95
Gly Val Tyr Glu Gln Ile Leu Asn Leu Asn Lys Glu Ser Phe Asn Lys
            100                 105                 110
Leu Val Arg Asp Asn His Thr Tyr Gly Asn Ile Pro Thr Ser Pro Glu
            115                 120                 125
Glu Leu Trp Asp Lys Val Ser Lys Leu Ile Tyr Ile Tyr Leu Lys Asp
            130                 135                 140
Pro Thr Asn Val Ile Gly Gln Ala Gly Trp Thr Asn Pro Gln Asp Ala
145                 150                 155                 160
Met Tyr Glu Phe Tyr Thr Val Gln Gln Glu Ile Trp Arg Tyr Thr
                165                 170                 175
Asp Gly Gln Lys Val Asp Lys Asp Thr Asn Ser Tyr Leu Tyr Tyr Lys
            180                 185                 190
Tyr Ser Lys Gln Gly Gln Lys Ala Val Tyr Leu Leu Arg Asp Ala Val
            195                 200                 205
Asn Ser Ile Ser Ile Pro Ser Asn Phe Glu Leu Arg Gly Tyr Lys Pro
            210                 215                 220
Glu Trp Val Gln Gly Gln Lys Gly Tyr Gln Ala Ile Val Thr Gly Arg
225                 230                 235                 240
Leu Lys Val Asp Gln Pro Val Gly Glu Ile Lys Thr Val Thr Ala
                245                 250                 255
Gly Gly Lys Thr Ser Ser Glu Asn Asp Ile Ala Thr Leu Lys Ala Gln
            260                 265                 270
Asp Val Ile Gly Gly Val Glu Val Ser Asp Lys Ile Thr Tyr Ser Gly
            275                 280                 285
Leu Tyr Pro Asn Thr Glu Tyr Asp Val Ile Gly Glu Ile Tyr Glu Val
            290                 295                 300
Lys Asp Gly Glu Leu Val Asn Pro Gly Arg Pro Val Ser Val Val Asn
305                 310                 315                 320
Ser Gly Asp Asp Leu Lys Thr Asp Ala Thr Gly Lys Gly Lys Trp Thr
            325                 330                 335
Leu Asn Phe Gly Lys Leu Asp Leu Glu Ala Gly Lys Ser Tyr Val Val
            340                 345                 350
Phe Glu Lys Val Val Ser Leu Lys Asn Val Ile Asp Thr Asp Gly Asp
            355                 360                 365
Gly Lys Pro Asp Lys Lys Gln Glu Leu Ser His Asn Asp Pro Lys Asp
            370                 375                 380
Lys Ser Gln Thr Phe Thr Ile Leu Pro Lys Glu Ile Val Glu Gln Asp
385                 390                 395                 400
Val Val Phe Ser Lys Val Asn Val Ala Gly Glu Glu Ile Ala Gly Ala
            405                 410                 415
Lys Ile Gln Leu Lys Asp Ala Gln Gly Gln Val Val His Ser Trp Thr
            420                 425                 430
Ser Lys Ala Gly Gln Ser Glu Thr Val Lys Leu Lys Ala Gly Thr Tyr
            435                 440                 445
Thr Phe His Glu Ala Ser Ala Pro Thr Gly Tyr Leu Ala Val Thr Asp
            450                 455                 460
Ile Thr Phe Glu Val Asp Val Gln Gly Lys Val Thr Val Lys Asp Ala
465                 470                 475                 480
Asn Gly Asn Gly Val Lys Ala Asp Gly Asn Lys Leu Thr Val Thr Asp
            485                 490                 495
Gln Ala Ala Pro Ser Val Pro Asn Glu Gln Asp Val Val Phe Ser Lys
```

```
                500                 505                 510
Val Asn Val Ala Gly Glu Glu Ile Ala Gly Ala Lys Ile Gln Leu Lys
            515                 520                 525

Asp Ala Gln Gly Gln Val Val His Ser Trp Thr Ser Lys Ala Gly Gln
        530                 535                 540

Ser Glu Thr Val Lys Leu Lys Ala Gly Thr Tyr Thr Phe His Glu Ala
545                 550                 555                 560

Ser Ala Pro Thr Gly Tyr Leu Ala Val Thr Asp Ile Thr Phe Glu Val
                565                 570                 575

Asp Val Gln Gly Lys Val Thr Val Lys Asp Ala Asn Gly Asn Gly Val
            580                 585                 590

Lys Ala Asp Gly Asn Lys Leu Thr Val Thr Asp Gln Ala Ala Pro Ser
        595                 600                 605

Val Pro Asn Glu Gln Asp Val Val Phe Ser Lys Val Asn Val Ala Gly
    610                 615                 620

Glu Glu Ile Ala Gly Ala Lys Ile Gln Leu Lys Asp Ala Gln Gly Gln
625                 630                 635                 640

Val Val His Ser Trp Thr Ser Lys Ala Gly Gln Ser Glu Thr Val Lys
                645                 650                 655

Leu Lys Ala Gly Thr Tyr Thr Phe His Glu Ala Ser Ala Pro Thr Gly
            660                 665                 670

Tyr Leu Ala Val Thr Asp Ile Thr Phe Glu Val Asp Val Gln Gly Lys
        675                 680                 685

Val Thr Val Lys Asp Ala Asn Gly Asn Gly Val Lys Ala Asp Gly Asn
    690                 695                 700

Lys Leu Thr Val Thr Asp Gln Ala Ala Pro Ser Val Pro Asn Glu Gln
705                 710                 715                 720

Asp Val Val Phe Ser Lys Val Asn Val Ala Gly Glu Glu Ile Ala Gly
                725                 730                 735

Ala Lys

<210> SEQ ID NO 32
<211> LENGTH: 2215
<212> TYPE: DNA
<213> ORGANISM: Streptococcus intermedius

<400> SEQUENCE: 32
atgaaaaaga gaagaggaca attttttcaaa agtgcaattt cgttttttggt tgtatttttg      60 atggtaatgg taagtatcat ttacccatct tcaaaaatta agcagatgg atttcctaat       120 gatgctacgg gagtatcgcc aaatggtaaa tattactcgg cagggagaga aaccgttta      180 ggaatggtta catcagatga attgcataca gctacagaat tattcggttt ttgtatggca     240
aatagcaaga aatatccagg atatgattca aaaaaggatg agtattttgg ggtgtatgaa     300
caaatcttaa accttaataa agaaagcttt aataagcttg ttagagataa tcatacgtat     360
ggtaacattc ctacaagtcc agaggaactt tgggataaag tatctaaact gatttatatt     420
tatttgaaag accctacaaa tgttattgga caagctgggt ggacgaatcc acaggatgca     480
atgtatgaat ttatactgt tgtacaacag gaaatggc gttatacaga tggacaaaag      540
gtggataaag acaccaattc atatttgtat tataaatatt caaacaagg tcaaaaagca     600 gtgtacttac tgcgtgacgc tgtgaatagc atcagtatac ctagtaattt tgaacttcgt     660
ggctataaac ctgaatgggt tcaaggtcaa aaaggatacc aagctattgt aactggtaga     720
ttgaaagtag atcaacctgt cggggaaata aagactacag taacagcagg tggaaaaacc     780
```

```
tcaagtgaaa acgacattgc tacattgaag gcgcaagacg ttataggtgg ggttgaagtc    840
tctgataaga taacatatag tggtctttat ccaaatacag aatatgatgt tataggtgaa    900
atttacgaag taaaagatgg agaacttgtt aatccaggac gaccggtttc tgtagtcaat    960
agtggtgacg atttaaaaac agatgcaaca ggaaaaggga aatggacatt aaactttgga   1020
aagcttgatt tagaagcagg aaaatcctat gtggtctttg aaaaagttgt tcattaaaa    1080 aacgtgatag atacagatgg agatggaaaa ccggataaaa acaagaact atcgcataat    1140 gatccaaaag ataaatcgca aacatttaca attttaccta aggaaatagt tgaacaagac   1200
gttgtcttca gtaaggtgaa tgtggctggt gaagaaatcg ctggtgcgaa gatccaactg   1260
aaggatgcgc aaggtcaagt tgttcattcc tggacttcta aagcgggtca aagtgaaacg   1320
gtcaaattga agctggcac ctatactttc catgaagcat ccgctccgac tggttacttg   1380
gccgtaacgg atatcacatt cgaagtagat gttcaaggaa aagtgacggt taaggatgcc   1440
aacggcaatg gtgttaaggc ggatggtaat aagttaacgg tgaccgatca agctgctcct   1500
agcgtaccga atgaacaaga cgttgtcttc agtaaggtga atgtggctgg tgaagaaatc   1560
gctggtgcga agatccaact gaaggatgcg caaggtcaag ttgttcattc ctggacttct   1620
aaagcgggtc aaagtgaaac ggtcaaattg aaagctggca cctatacttt ccatgaagca   1680
tccgctccga ctggttactt ggccgtaacg gatatcacat tcgaagtaga tgttcaagga   1740
aaagtgacgg ttaaggatgc caacggcaat ggtgttaagg cggatggtaa taagttaacg   1800
gtgaccgatc aagctgctcc tagcgtaccg aatgaacaag acgttgtctt cagtaaggtg   1860
aatgtggctg gtgaagaaat cgctggtgcg aagatccaac tgaaggatgc gcaaggtcaa   1920
gttgttcatt cctggacttc taaagcgggt caaagtgaaa cggtcaaatt gaaagctggc   1980
acctatactt tccatgaagc atccgctccg actggttact tggccgtaac ggatatcaca   2040
ttcgaagtag atgttcaagg aaaagtgacg gttaaggatg ccaacggcaa tggtgttaag   2100
gcggatggta ataagttaac ggtgaccgat caagctgctc ctagcgtacc gaatgaacaa   2160
gacgttgtct tcagtaaggt gaatgtggct ggtgaagaaa tcgctggtgc gaaga        2215
```

<210> SEQ ID NO 33
<211> LENGTH: 10
<212> TYPE: PRT
<213> ORGANISM: Artificial sequence
<220> FEATURE:
<223> OTHER INFORMATION: K-tag

<400> SEQUENCE: 33

Ala Thr His Ile Lys Phe Ser Lys Arg Asp
1               5                   10

<210> SEQ ID NO 34
<211> LENGTH: 108
<212> TYPE: PRT
<213> ORGANISM: Artificial sequence
<220> FEATURE:
<223> OTHER INFORMATION: SpyLigase

<400> SEQUENCE: 34

Met Ser Tyr Tyr His His His His His His Asp Tyr Asp Gly Gln Ser
1               5                   10                  15

Gly Asp Gly Lys Glu Leu Ala Gly Ala Thr Met Glu Leu Arg Asp Ser
            20                  25                  30

Ser Gly Lys Thr Ile Ser Thr Trp Ile Ser Asp Gly Gln Val Lys Asp

```
                35                  40                  45
Phe Tyr Leu Tyr Pro Gly Lys Tyr Thr Phe Val Glu Thr Ala Ala Pro
         50                  55                  60

Asp Gly Tyr Glu Val Ala Thr Ala Ile Thr Phe Thr Val Asn Glu Gln
65                  70                  75                  80

Gly Gln Val Thr Val Asn Gly Lys Ala Thr Lys Gly Ser Gly Gly
                85                  90                  95

Ser Gly Gly Ser Gly Glu Asp Ser Ala Thr His Ile
            100                 105

<210> SEQ ID NO 35
<211> LENGTH: 327
<212> TYPE: DNA
<213> ORGANISM: Artificial sequence
<220> FEATURE:
<223> OTHER INFORMATION: SpyLigase

<400> SEQUENCE: 35
atgtcgtact accatcacca tcaccatcac gattacgacg gtcagtccgg tgacggcaaa      60
gagttagctg gtgcaactat ggagttgcgt gattcatctg gtaaaactat tagtacatgg    120
atttcagatg gacaagtgaa agatttctac ctgtatccag aaaatatac atttgtcgaa     180 accgcagcac cagacggtta tgaggtagca actgctatta cctttacagt taatgagcaa    240
ggtcaggtta ctgtaaatgg caaagcaact aaaggtggga gtggtggcag cggaggtagt    300
ggcgaggaca gcgctaccca tatttaa                                         327

<210> SEQ ID NO 36
<211> LENGTH: 12
<212> TYPE: PRT
<213> ORGANISM: Artificial sequence
<220> FEATURE:
<223> OTHER INFORMATION: Spacer

<400> SEQUENCE: 36

Ser Ser Gly Leu Val Pro Arg Gly Ser His Met Gly
1               5                   10

<210> SEQ ID NO 37
<211> LENGTH: 6
<212> TYPE: PRT
<213> ORGANISM: Artificial sequence
<220> FEATURE:
<223> OTHER INFORMATION: Spacer

<400> SEQUENCE: 37

Gly Ser Gly Glu Ser Gly
1               5

<210> SEQ ID NO 38
<211> LENGTH: 33
<212> TYPE: PRT
<213> ORGANISM: Artificial sequence
<220> FEATURE:
<223> OTHER INFORMATION: SnoopTag-His

<400> SEQUENCE: 38

Met Gly Ser Ser His His His His His His Ser Ser Gly Leu Val Pro
1               5                   10                  15

Arg Gly Ser His Met Lys Leu Gly Asp Ile Glu Phe Ile Lys Val Asn
            20                  25                  30

Lys
```

<210> SEQ ID NO 39
<211> LENGTH: 133
<212> TYPE: PRT
<213> ORGANISM: Artificial sequence
<220> FEATURE:
<223> OTHER INFORMATION: SnoopCatcher-His

<400> SEQUENCE: 39

Met Gly Ser Ser His His His His His Ser Gly Leu Val Pro
1               5                   10                  15

Arg Gly Ser His Met Lys Pro Leu Arg Gly Ala Val Phe Ser Leu Gln
            20                  25                  30

Lys Gln His Pro Asp Tyr Pro Asp Ile Tyr Gly Ala Ile Asp Gln Asn
        35                  40                  45

Gly Thr Tyr Gln Asn Val Arg Thr Gly Glu Asp Gly Lys Leu Thr Phe
    50                  55                  60

Lys Asn Leu Ser Asp Gly Lys Tyr Arg Leu Phe Glu Asn Ser Glu Pro
65                  70                  75                  80

Ala Gly Tyr Lys Pro Val Gln Asn Lys Pro Ile Val Ala Phe Gln Ile
                85                  90                  95

Val Asn Gly Glu Val Arg Asp Val Thr Ser Ile Val Pro Gln Asp Ile
            100                 105                 110

Pro Ala Thr Tyr Glu Phe Thr Asn Gly Lys His Tyr Ile Thr Asn Glu
        115                 120                 125

Pro Ile Pro Pro Lys
    130

<210> SEQ ID NO 40
<211> LENGTH: 99
<212> TYPE: DNA
<213> ORGANISM: Artificial sequence
<220> FEATURE:
<223> OTHER INFORMATION: SnoopTag-His

<400> SEQUENCE: 40
atgggcagca gccatcatca tcatcatcac agcagcggcc tggtgccgcg cggcagccat      60
atgaaactgg gcgatattga atttattaaa gtgaacaaa                             99

<210> SEQ ID NO 41
<211> LENGTH: 399
<212> TYPE: DNA
<213> ORGANISM: Artificial sequence
<220> FEATURE:
<223> OTHER INFORMATION: SnoopCatcher-His

<400> SEQUENCE: 41
atgggcagca gccatcatca tcatcatcac agcagcggcc tggtgccgcg cggcagccat      60
atgaagccgc tgcgtggtgc cgtgtttagc ctgcagaaac agcatcccga ctatcccgat     120
atctatggcg cgattgatca gaatgggacc tatcaaaatg tgcgtaccgg cgaagatggt     180
aaactgacct ttaagaatct gagcgatggc aaatatcgcc tgtttgaaaa tagcgaaccc     240
gctggctata aaccggtgca gaataagccg attgtggcgt ttcagattgt gaatggcgaa     300
gtgcgtgatg tgaccagcat tgtgccgcag gatattccgg ctacatatga atttaccaac     360
ggtaaacatt atatcaccaa tgaaccgata ccgccgaaa                            399

<210> SEQ ID NO 42
<211> LENGTH: 35

```
<212> TYPE: PRT
<213> ORGANISM: Artificial sequence
<220> FEATURE:
<223> OTHER INFORMATION: PsCsTag-His

<400> SEQUENCE: 42

Met Gly Ser Ser His His His His His His Ser Ser Gly Leu Val Pro
1               5                   10                  15

Arg Gly Ser His Met Gly Gly Asn Lys Leu Thr Val Thr Asp Gln Ala
            20                  25                  30

Ala Pro Ser
        35

<210> SEQ ID NO 43
<211> LENGTH: 112
<212> TYPE: PRT
<213> ORGANISM: Artificial sequence
<220> FEATURE:
<223> OTHER INFORMATION: PsCsCatcher-His

<400> SEQUENCE: 43

Met Gly Ser Ser His His His His His His Ser Ser Gly Leu Val Pro
1               5                   10                  15

Arg Gly Ser His Met Glu Gln Asp Val Val Phe Ser Lys Val Asn Val
            20                  25                  30

Ala Gly Glu Glu Ile Ala Gly Ala Lys Ile Gln Leu Lys Asp Ala Gln
            35                  40                  45

Gly Gln Val Val His Ser Trp Thr Ser Lys Ala Gly Gln Ser Glu Thr
    50                  55                  60

Val Lys Leu Lys Ala Gly Thr Tyr Thr Phe His Glu Ala Ser Ala Pro
65                  70                  75                  80

Thr Gly Tyr Leu Ala Val Thr Asp Ile Thr Phe Glu Val Asp Val Gln
                85                  90                  95

Gly Lys Val Thr Val Lys Asp Ala Asn Gly Asn Gly Val Lys Ala Asp
                100                 105                 110

<210> SEQ ID NO 44
<211> LENGTH: 105
<212> TYPE: DNA
<213> ORGANISM: Artificial sequence
<220> FEATURE:
<223> OTHER INFORMATION: PsCsTag-His

<400> SEQUENCE: 44
atgggcagca gccatcatca tcatcatcac agcagcggcc tggtgccgcg cggcagccat    60
atgggaggca acaaactgac cgtgaccgat caggcggcgc cgagc                   105

<210> SEQ ID NO 45
<211> LENGTH: 336
<212> TYPE: DNA
<213> ORGANISM: Artificial sequence
<220> FEATURE:
<223> OTHER INFORMATION: PsCsCatcher-His

<400> SEQUENCE: 45
atgggcagca gccatcatca tcatcatcac agcagcggcc tggtgccgcg cggcagccat    60
atggaacagg atgtggtgtt tagcaaagtg aatgtggctg gcgaggaaat tgcgggagcg   120
aaaattcagt tgaaagacgc gcagggccag gtggtgcata gctggaccag caaagcgggc   180
caaagcgaaa ccgtgaagct gaaagccggc acctatacct tcatgaggc gagcgcaccg   240
```

```
accggctatc tggcggtgac cgatattacc tttgaagtgg atgtgcaggg caaagttaca    300
gtgaaagatg cgaatggcaa tggtgtgaaa gcggat                              336
```

<210> SEQ ID NO 46
<211> LENGTH: 41
<212> TYPE: PRT
<213> ORGANISM: Artificial sequence
<220> FEATURE:
<223> OTHER INFORMATION: RrgATag-His

<400> SEQUENCE: 46

Met Gly Ser Ser His His His His His His Ser Ser Gly Leu Val Pro
1               5                   10                  15

Arg Gly Ser His Met Gly Asp Ile Pro Ala Thr Tyr Glu Phe Thr Asn
            20                  25                  30

Asp Lys His Tyr Ile Thr Asn Glu Pro
        35                  40

<210> SEQ ID NO 47
<211> LENGTH: 125
<212> TYPE: PRT
<213> ORGANISM: Artificial sequence
<220> FEATURE:
<223> OTHER INFORMATION: RrgACatcher-His

<400> SEQUENCE: 47

Met Gly Ser Ser His His His His His His Ser Ser Gly Leu Val Pro
1               5                   10                  15

Arg Gly Ser His Met Lys Leu Gly Asp Ile Glu Phe Ile Lys Val Asn
            20                  25                  30

Lys Asn Asp Lys Lys Pro Leu Arg Gly Ala Val Phe Ser Leu Gln Lys
        35                  40                  45

Gln His Pro Asp Tyr Pro Asp Ile Tyr Gly Ala Ile Asp Gln Asn Gly
    50                  55                  60

Thr Tyr Gln Asn Val Arg Thr Gly Glu Asp Gly Lys Leu Thr Phe Lys
65                  70                  75                  80

Asn Leu Ser Asp Gly Lys Tyr Arg Leu Phe Glu Asn Ser Glu Pro Ala
                85                  90                  95

Gly Tyr Lys Pro Val Gln Asn Lys Pro Ile Val Ala Phe Gln Ile Val
            100                 105                 110

Asn Gly Glu Val Arg Asp Val Thr Ser Ile Val Pro Gln
        115                 120                 125

<210> SEQ ID NO 48
<211> LENGTH: 123
<212> TYPE: DNA
<213> ORGANISM: Artificial sequence
<220> FEATURE:
<223> OTHER INFORMATION: RrgATag-His

<400> SEQUENCE: 48

```
atgggcagca gccatcatca tcatcatcac agcagcggcc tgtgccgcg cggcagccat    60 atgggagata ttccggctac atatgaattt accaacgata acattatat caccaatgaa   120 ccg                                                                 123
```

<210> SEQ ID NO 49
<211> LENGTH: 375
<212> TYPE: DNA
<213> ORGANISM: Artificial sequence
<220> FEATURE:

<223> OTHER INFORMATION: RrgACatcher-His

<400> SEQUENCE: 49

```
atgggcagca gccatcatca tcatcatcac agcagcggcc tggtgccgcg cggcagccat      60
atgaaactgg gcgatattga atttattaaa gtgaacaaaa acgataaaaa gccgctgcgt     120
ggtgccgtgt ttagcctgca gaaacagcat cccgactatc cgatatcta tggcgcgatt     180
gatcagaatg ggacctatca aaatgtgcgt accggcgaag atggtaaact gacctttaag    240
aatctgagcg atggcaaata tcgcctgttt gaaaatagcg aacccgctgg ctataaaccg    300
gtgcagaata gccgattgt ggcgtttcag attgtgaatg cgaagtgcg tgatgtgacc      360
agcattgtgc cgcag                                                       375
```

<210> SEQ ID NO 50
<211> LENGTH: 409
<212> TYPE: PRT
<213> ORGANISM: Artificial sequence
<220> FEATURE:
<223> OTHER INFORMATION: SnoopTag-MBP

<400> SEQUENCE: 50

```
Met Gly Ser Ser His His His His His Ser Ser Gly Leu Val Pro
1               5                   10                  15
Arg Gly Ser His Met Lys Leu Gly Asp Ile Glu Phe Ile Lys Val Asn
                20                  25                  30
Lys Gly Ser Gly Glu Ser Gly Lys Ile Glu Glu Gly Lys Leu Val Ile
            35                  40                  45
Trp Ile Asn Gly Asp Lys Gly Tyr Asn Gly Leu Ala Glu Val Gly Lys
        50                  55                  60
Lys Phe Glu Lys Asp Thr Gly Ile Lys Val Thr Val Glu His Pro Asp
65                  70                  75                  80
Lys Leu Glu Glu Lys Phe Pro Gln Val Ala Ala Thr Gly Asp Gly Pro
                85                  90                  95
Asp Ile Ile Phe Trp Ala His Asp Arg Phe Gly Gly Tyr Ala Gln Ser
            100                 105                 110
Gly Leu Leu Ala Glu Ile Thr Pro Asp Lys Ala Phe Gln Asp Lys Leu
        115                 120                 125
Tyr Pro Phe Thr Trp Asp Ala Val Arg Tyr Asn Gly Lys Leu Ile Ala
130                 135                 140
Tyr Pro Ile Ala Val Glu Ala Leu Ser Leu Ile Tyr Asn Lys Asp Leu
145                 150                 155                 160
Leu Pro Asn Pro Pro Lys Thr Trp Glu Glu Ile Pro Ala Leu Asp Lys
                165                 170                 175
Glu Leu Lys Ala Lys Gly Lys Ser Ala Leu Met Phe Asn Leu Gln Glu
            180                 185                 190
Pro Tyr Phe Thr Trp Pro Leu Ile Ala Ala Asp Gly Gly Tyr Ala Phe
        195                 200                 205
Lys Tyr Glu Asn Gly Lys Tyr Asp Ile Lys Asp Val Gly Val Asp Asn
210                 215                 220
Ala Gly Ala Lys Ala Gly Leu Thr Phe Leu Val Asp Leu Ile Lys Asn
225                 230                 235                 240
Lys His Met Asn Ala Asp Thr Asp Tyr Ser Ile Ala Glu Ala Ala Phe
                245                 250                 255
Asn Lys Gly Glu Thr Ala Met Thr Ile Asn Gly Pro Trp Ala Trp Ser
            260                 265                 270
```

```
Asn Ile Asp Thr Ser Lys Val Asn Tyr Gly Val Thr Val Leu Pro Thr
            275                 280                 285

Phe Lys Gly Gln Pro Ser Lys Pro Phe Val Gly Val Leu Ser Ala Gly
290                 295                 300

Ile Asn Ala Ala Ser Pro Asn Lys Glu Leu Ala Lys Glu Phe Leu Glu
305                 310                 315                 320

Asn Tyr Leu Leu Thr Asp Glu Gly Leu Glu Ala Val Asn Lys Asp Lys
                325                 330                 335

Pro Leu Gly Ala Val Ala Leu Lys Ser Tyr Glu Glu Glu Leu Ala Lys
                340                 345                 350

Asp Pro Arg Ile Ala Ala Thr Met Glu Asn Ala Gln Lys Gly Glu Ile
            355                 360                 365

Met Pro Asn Ile Pro Gln Met Ser Ala Phe Trp Tyr Ala Val Arg Thr
370                 375                 380

Ala Val Ile Asn Ala Ala Ser Gly Arg Gln Thr Val Asp Glu Ala Leu
385                 390                 395                 400

Lys Asp Ala Gln Thr Asn Ser Ser Ser
                405
```

<210> SEQ ID NO 51
<211> LENGTH: 509
<212> TYPE: PRT
<213> ORGANISM: Artificial sequence
<220> FEATURE:
<223> OTHER INFORMATION: SnoopCatcher-MBP

<400> SEQUENCE: 51

```
Met Gly Ser Ser His His His His His His Ser Ser Gly Leu Val Pro
1               5                   10                  15

Arg Gly Ser His Met Lys Pro Leu Arg Gly Ala Val Phe Ser Leu Gln
                20                  25                  30

Lys Gln His Pro Asp Tyr Pro Asp Ile Tyr Gly Ala Ile Asp Gln Asn
            35                  40                  45

Gly Thr Tyr Gln Asn Val Arg Thr Gly Glu Asp Gly Lys Leu Thr Phe
        50                  55                  60

Lys Asn Leu Ser Asp Gly Lys Tyr Arg Leu Phe Glu Asn Ser Glu Pro
65                  70                  75                  80

Ala Gly Tyr Lys Pro Val Gln Asn Lys Pro Ile Val Ala Phe Gln Ile
                85                  90                  95

Val Asn Gly Glu Val Arg Asp Val Thr Ser Ile Val Pro Gln Asp Ile
                100                 105                 110

Pro Ala Thr Tyr Glu Phe Thr Asn Gly Lys His Tyr Ile Thr Asn Glu
            115                 120                 125

Pro Ile Pro Pro Lys Gly Ser Gly Glu Ser Gly Lys Ile Glu Glu Gly
        130                 135                 140

Lys Leu Val Ile Trp Ile Asn Gly Asp Lys Gly Tyr Asn Gly Leu Ala
145                 150                 155                 160

Glu Val Gly Lys Lys Phe Glu Lys Asp Thr Gly Ile Lys Val Thr Val
                165                 170                 175

Glu His Pro Asp Lys Leu Glu Glu Lys Phe Pro Gln Val Ala Ala Thr
            180                 185                 190

Gly Asp Gly Pro Asp Ile Ile Phe Trp Ala His Asp Arg Phe Gly Gly
        195                 200                 205

Tyr Ala Gln Ser Gly Leu Leu Ala Glu Ile Thr Pro Asp Lys Ala Phe
    210                 215                 220
```

-continued

```
Gln Asp Lys Leu Tyr Pro Phe Thr Trp Asp Ala Val Arg Tyr Asn Gly
225                 230                 235                 240

Lys Leu Ile Ala Tyr Pro Ile Ala Val Glu Ala Leu Ser Leu Ile Tyr
            245                 250                 255

Asn Lys Asp Leu Leu Pro Asn Pro Pro Lys Thr Trp Glu Glu Ile Pro
        260                 265                 270

Ala Leu Asp Lys Glu Leu Lys Ala Lys Gly Lys Ser Ala Leu Met Phe
    275                 280                 285

Asn Leu Gln Glu Pro Tyr Phe Thr Trp Pro Leu Ile Ala Ala Asp Gly
290                 295                 300

Gly Tyr Ala Phe Lys Tyr Glu Asn Gly Lys Tyr Asp Ile Lys Asp Val
305                 310                 315                 320

Gly Val Asp Asn Ala Gly Ala Lys Ala Gly Leu Thr Phe Leu Val Asp
            325                 330                 335

Leu Ile Lys Asn Lys His Met Asn Ala Asp Thr Asp Tyr Ser Ile Ala
        340                 345                 350

Glu Ala Ala Phe Asn Lys Gly Glu Thr Ala Met Thr Ile Asn Gly Pro
    355                 360                 365

Trp Ala Trp Ser Asn Ile Asp Thr Ser Lys Val Asn Tyr Gly Val Thr
370                 375                 380

Val Leu Pro Thr Phe Lys Gly Gln Pro Ser Lys Pro Phe Val Gly Val
385                 390                 395                 400

Leu Ser Ala Gly Ile Asn Ala Ala Ser Pro Asn Lys Glu Leu Ala Lys
            405                 410                 415

Glu Phe Leu Glu Asn Tyr Leu Leu Thr Asp Glu Gly Leu Glu Ala Val
        420                 425                 430

Asn Lys Asp Lys Pro Leu Gly Ala Val Ala Leu Lys Ser Tyr Glu Glu
    435                 440                 445

Glu Leu Ala Lys Asp Pro Arg Ile Ala Ala Thr Met Glu Asn Ala Gln
450                 455                 460

Lys Gly Glu Ile Met Pro Asn Ile Pro Gln Met Ser Ala Phe Trp Tyr
465                 470                 475                 480

Ala Val Arg Thr Ala Val Ile Asn Ala Ala Ser Gly Arg Gln Thr Val
            485                 490                 495

Asp Glu Ala Leu Lys Asp Ala Gln Thr Asn Ser Ser Ser
        500                 505
```

<210> SEQ ID NO 52
<211> LENGTH: 411
<212> TYPE: PRT
<213> ORGANISM: Artificial sequence
<220> FEATURE:
<223> OTHER INFORMATION: PsCsTag-MBP

<400> SEQUENCE: 52

```
Met Gly Ser Ser His His His His His His Ser Ser Gly Leu Val Pro
1               5                   10                  15

Arg Gly Ser His Met Gly Gly Asn Lys Leu Thr Val Thr Asp Gln Ala
            20                  25                  30

Ala Pro Ser Gly Ser Gly Glu Ser Gly Lys Ile Glu Glu Gly Lys Leu
        35                  40                  45

Val Ile Trp Ile Asn Gly Asp Lys Gly Tyr Asn Gly Leu Ala Glu Val
    50                  55                  60

Gly Lys Lys Phe Glu Lys Asp Thr Gly Ile Lys Val Thr Val Glu His
65                  70                  75                  80
```

Pro Asp Lys Leu Glu Glu Lys Phe Pro Gln Val Ala Ala Thr Gly Asp
            85                  90                  95

Gly Pro Asp Ile Ile Phe Trp Ala His Asp Arg Phe Gly Gly Tyr Ala
        100                 105                 110

Gln Ser Gly Leu Leu Ala Glu Ile Thr Pro Asp Lys Ala Phe Gln Asp
        115                 120                 125

Lys Leu Tyr Pro Phe Thr Trp Asp Ala Val Arg Tyr Asn Gly Lys Leu
    130                 135                 140

Ile Ala Tyr Pro Ile Ala Val Glu Ala Leu Ser Leu Ile Tyr Asn Lys
145                 150                 155                 160

Asp Leu Leu Pro Asn Pro Pro Lys Thr Trp Glu Glu Ile Pro Ala Leu
                165                 170                 175

Asp Lys Glu Leu Lys Ala Lys Gly Lys Ser Ala Leu Met Phe Asn Leu
            180                 185                 190

Gln Glu Pro Tyr Phe Thr Trp Pro Leu Ile Ala Ala Asp Gly Gly Tyr
        195                 200                 205

Ala Phe Lys Tyr Glu Asn Gly Lys Tyr Asp Ile Lys Asp Val Gly Val
        210                 215                 220

Asp Asn Ala Gly Ala Lys Ala Gly Leu Thr Phe Leu Val Asp Leu Ile
225                 230                 235                 240

Lys Asn Lys His Met Asn Ala Asp Thr Asp Tyr Ser Ile Ala Glu Ala
                245                 250                 255

Ala Phe Asn Lys Gly Glu Thr Ala Met Thr Ile Asn Gly Pro Trp Ala
            260                 265                 270

Trp Ser Asn Ile Asp Thr Ser Lys Val Asn Tyr Gly Val Thr Val Leu
    275                 280                 285

Pro Thr Phe Lys Gly Gln Pro Ser Lys Pro Phe Val Gly Val Leu Ser
290                 295                 300

Ala Gly Ile Asn Ala Ala Ser Pro Asn Lys Glu Leu Ala Lys Glu Phe
305                 310                 315                 320

Leu Glu Asn Tyr Leu Leu Thr Asp Glu Gly Leu Glu Ala Val Asn Lys
            325                 330                 335

Asp Lys Pro Leu Gly Ala Val Ala Leu Lys Ser Tyr Glu Glu Glu Leu
        340                 345                 350

Ala Lys Asp Pro Arg Ile Ala Ala Thr Met Glu Asn Ala Gln Lys Gly
        355                 360                 365

Glu Ile Met Pro Asn Ile Pro Gln Met Ser Ala Phe Trp Tyr Ala Val
    370                 375                 380

Arg Thr Ala Val Ile Asn Ala Ala Ser Gly Arg Gln Thr Val Asp Glu
385                 390                 395                 400

Ala Leu Lys Asp Ala Gln Thr Asn Ser Ser Ser
                405                 410

<210> SEQ ID NO 53
<211> LENGTH: 488
<212> TYPE: PRT
<213> ORGANISM: Artificial sequence
<220> FEATURE:
<223> OTHER INFORMATION: PsCsCatcherMBP

<400> SEQUENCE: 53

Met Gly Ser Ser His His His His His His Ser Ser Gly Leu Val Pro
1               5                   10                  15

Arg Gly Ser His Met Glu Gln Asp Val Val Phe Ser Lys Val Asn Val
            20                  25                  30

-continued

Ala Gly Glu Glu Ile Ala Gly Ala Lys Ile Gln Leu Lys Asp Ala Gln
             35                  40                  45

Gly Gln Val Val His Ser Trp Thr Ser Lys Ala Gly Gln Ser Glu Thr
 50                  55                  60

Val Lys Leu Lys Ala Gly Thr Tyr Thr Phe His Glu Ala Ser Ala Pro
 65                  70                  75                  80

Thr Gly Tyr Leu Ala Val Thr Asp Ile Thr Phe Glu Val Asp Val Gln
                 85                  90                  95

Gly Lys Val Thr Val Lys Asp Ala Asn Gly Asn Gly Val Lys Ala Asp
                100                 105                 110

Gly Ser Gly Glu Ser Gly Lys Ile Glu Glu Gly Lys Leu Val Ile Trp
             115                 120                 125

Ile Asn Gly Asp Lys Gly Tyr Asn Gly Leu Ala Glu Val Gly Lys Lys
130                 135                 140

Phe Glu Lys Asp Thr Gly Ile Lys Val Thr Val Glu His Pro Asp Lys
145                 150                 155                 160

Leu Glu Glu Lys Phe Pro Gln Val Ala Ala Thr Gly Asp Gly Pro Asp
                165                 170                 175

Ile Ile Phe Trp Ala His Asp Arg Phe Gly Gly Tyr Ala Gln Ser Gly
             180                 185                 190

Leu Leu Ala Glu Ile Thr Pro Asp Lys Ala Phe Gln Asp Lys Leu Tyr
            195                 200                 205

Pro Phe Thr Trp Asp Ala Val Arg Tyr Asn Gly Lys Leu Ile Ala Tyr
            210                 215                 220

Pro Ile Ala Val Glu Ala Leu Ser Leu Ile Tyr Asn Lys Asp Leu Leu
225                 230                 235                 240

Pro Asn Pro Pro Lys Thr Trp Glu Glu Ile Pro Ala Leu Asp Lys Glu
                245                 250                 255

Leu Lys Ala Lys Gly Lys Ser Ala Leu Met Phe Asn Leu Gln Glu Pro
            260                 265                 270

Tyr Phe Thr Trp Pro Leu Ile Ala Ala Asp Gly Gly Tyr Ala Phe Lys
            275                 280                 285

Tyr Glu Asn Gly Lys Tyr Asp Ile Lys Asp Val Gly Val Asp Asn Ala
290                 295                 300

Gly Ala Lys Ala Gly Leu Thr Phe Leu Val Asp Leu Ile Lys Asn Lys
305                 310                 315                 320

His Met Asn Ala Asp Thr Asp Tyr Ser Ile Ala Glu Ala Ala Phe Asn
                325                 330                 335

Lys Gly Glu Thr Ala Met Thr Ile Asn Gly Pro Trp Ala Trp Ser Asn
            340                 345                 350

Ile Asp Thr Ser Lys Val Asn Tyr Gly Val Thr Val Leu Pro Thr Phe
            355                 360                 365

Lys Gly Gln Pro Ser Lys Pro Phe Val Gly Val Leu Ser Ala Gly Ile
370                 375                 380

Asn Ala Ala Ser Pro Asn Lys Glu Leu Ala Lys Glu Phe Leu Glu Asn
385                 390                 395                 400

Tyr Leu Leu Thr Asp Glu Gly Leu Glu Ala Val Asn Lys Asp Lys Pro
                405                 410                 415

Leu Gly Ala Val Ala Leu Lys Ser Tyr Glu Glu Glu Leu Ala Lys Asp
            420                 425                 430

Pro Arg Ile Ala Ala Thr Met Glu Asn Ala Gln Lys Gly Glu Ile Met
            435                 440                 445

Pro Asn Ile Pro Gln Met Ser Ala Phe Trp Tyr Ala Val Arg Thr Ala

```
                450                 455                 460
Val Ile Asn Ala Ala Ser Gly Arg Gln Thr Val Asp Glu Ala Leu Lys
465                 470                 475                 480

Asp Ala Gln Thr Asn Ser Ser Ser
                485

<210> SEQ ID NO 54
<211> LENGTH: 417
<212> TYPE: PRT
<213> ORGANISM: Artificial sequence
<220> FEATURE:
<223> OTHER INFORMATION: RrgATag-MBP

<400> SEQUENCE: 54

Met Gly Ser Ser His His His His His Ser Ser Gly Leu Val Pro
1               5                   10                  15

Arg Gly Ser His Met Gly Asp Ile Pro Ala Thr Tyr Glu Phe Thr Asn
                20                  25                  30

Asp Lys His Tyr Ile Thr Asn Glu Pro Gly Ser Gly Glu Ser Gly Lys
            35                  40                  45

Ile Glu Glu Gly Lys Leu Val Ile Trp Ile Asn Gly Asp Lys Gly Tyr
50                  55                  60

Asn Gly Leu Ala Glu Val Gly Lys Lys Phe Glu Lys Asp Thr Gly Ile
65                  70                  75                  80

Lys Val Thr Val Glu His Pro Asp Lys Leu Glu Glu Lys Phe Pro Gln
                85                  90                  95

Val Ala Ala Thr Gly Asp Gly Pro Asp Ile Ile Phe Trp Ala His Asp
            100                 105                 110

Arg Phe Gly Gly Tyr Ala Gln Ser Gly Leu Leu Ala Glu Ile Thr Pro
        115                 120                 125

Asp Lys Ala Phe Gln Asp Lys Leu Tyr Pro Phe Thr Trp Asp Ala Val
130                 135                 140

Arg Tyr Asn Gly Lys Leu Ile Ala Tyr Pro Ile Ala Val Glu Ala Leu
145                 150                 155                 160

Ser Leu Ile Tyr Asn Lys Asp Leu Leu Pro Asn Pro Pro Lys Thr Trp
                165                 170                 175

Glu Glu Ile Pro Ala Leu Asp Lys Glu Leu Lys Ala Lys Gly Lys Ser
            180                 185                 190

Ala Leu Met Phe Asn Leu Gln Glu Pro Tyr Phe Thr Trp Pro Leu Ile
        195                 200                 205

Ala Ala Asp Gly Gly Tyr Ala Phe Lys Tyr Glu Asn Gly Lys Tyr Asp
210                 215                 220

Ile Lys Asp Val Gly Val Asp Asn Ala Gly Ala Lys Ala Gly Leu Thr
225                 230                 235                 240

Phe Leu Val Asp Leu Ile Lys Asn Lys His Met Asn Ala Asp Thr Asp
                245                 250                 255

Tyr Ser Ile Ala Glu Ala Ala Phe Asn Lys Gly Glu Thr Ala Met Thr
            260                 265                 270

Ile Asn Gly Pro Trp Ala Trp Ser Asn Ile Asp Thr Ser Lys Val Asn
        275                 280                 285

Tyr Gly Val Thr Val Leu Pro Thr Phe Lys Gly Gln Pro Ser Lys Pro
290                 295                 300

Phe Val Gly Val Leu Ser Ala Gly Ile Asn Ala Ala Ser Pro Asn Lys
305                 310                 315                 320

Glu Leu Ala Lys Glu Phe Leu Glu Asn Tyr Leu Leu Thr Asp Glu Gly
```

```
                    325                 330                 335
Leu Glu Ala Val Asn Lys Asp Lys Pro Leu Gly Ala Val Ala Leu Lys
                340                 345                 350

Ser Tyr Glu Glu Leu Ala Lys Asp Pro Arg Ile Ala Ala Thr Met
            355                 360                 365

Glu Asn Ala Gln Lys Gly Glu Ile Met Pro Asn Ile Pro Gln Met Ser
        370                 375                 380

Ala Phe Trp Tyr Ala Val Arg Thr Ala Val Ile Asn Ala Ala Ser Gly
385                 390                 395                 400

Arg Gln Thr Val Asp Glu Ala Leu Lys Asp Ala Gln Thr Asn Ser Ser
                405                 410                 415

Ser

<210> SEQ ID NO 55
<211> LENGTH: 501
<212> TYPE: PRT
<213> ORGANISM: Artificial sequence
<220> FEATURE:
<223> OTHER INFORMATION: RrgACatcher-MBP

<400> SEQUENCE: 55

Met Gly Ser Ser His His His His His His Ser Ser Gly Leu Val Pro
1               5                   10                  15

Arg Gly Ser His Met Lys Leu Gly Asp Ile Glu Phe Ile Lys Val Asn
                20                  25                  30

Lys Asn Asp Lys Lys Pro Leu Arg Gly Ala Val Phe Ser Leu Gln Lys
            35                  40                  45

Gln His Pro Asp Tyr Pro Asp Ile Tyr Gly Ala Ile Asp Gln Asn Gly
        50                  55                  60

Thr Tyr Gln Asn Val Arg Thr Gly Glu Asp Gly Lys Leu Thr Phe Lys
65                  70                  75                  80

Asn Leu Ser Asp Gly Lys Tyr Arg Leu Phe Glu Asn Ser Glu Pro Ala
                85                  90                  95

Gly Tyr Lys Pro Val Gln Asn Lys Pro Ile Val Ala Phe Gln Ile Val
            100                 105                 110

Asn Gly Glu Val Arg Asp Val Thr Ser Ile Val Pro Gln Gly Ser Gly
        115                 120                 125

Glu Ser Gly Lys Ile Glu Gly Lys Leu Val Ile Trp Ile Asn Gly
            130                 135                 140

Asp Lys Gly Tyr Asn Gly Leu Ala Glu Val Gly Lys Lys Phe Glu Lys
145                 150                 155                 160

Asp Thr Gly Ile Lys Val Thr Val Glu His Pro Asp Lys Leu Glu Glu
                165                 170                 175

Lys Phe Pro Gln Val Ala Ala Thr Gly Asp Gly Pro Asp Ile Ile Phe
            180                 185                 190

Trp Ala His Asp Arg Phe Gly Gly Tyr Ala Gln Ser Gly Leu Leu Ala
        195                 200                 205

Glu Ile Thr Pro Asp Lys Ala Phe Gln Asp Lys Leu Tyr Pro Phe Thr
    210                 215                 220

Trp Asp Ala Val Arg Tyr Asn Gly Lys Leu Ile Ala Tyr Pro Ile Ala
225                 230                 235                 240

Val Glu Ala Leu Ser Leu Ile Tyr Asn Lys Asp Leu Leu Pro Asn Pro
                245                 250                 255

Pro Lys Thr Trp Glu Glu Ile Pro Ala Leu Asp Lys Glu Leu Lys Ala
            260                 265                 270
```

```
Lys Gly Lys Ser Ala Leu Met Phe Asn Leu Gln Glu Pro Tyr Phe Thr
            275                 280                 285

Trp Pro Leu Ile Ala Ala Asp Gly Gly Tyr Ala Phe Lys Tyr Glu Asn
290                 295                 300

Gly Lys Tyr Asp Ile Lys Asp Val Gly Val Asp Asn Ala Gly Ala Lys
305                 310                 315                 320

Ala Gly Leu Thr Phe Leu Val Asp Leu Ile Lys Asn Lys His Met Asn
            325                 330                 335

Ala Asp Thr Asp Tyr Ser Ile Ala Glu Ala Ala Phe Asn Lys Gly Glu
            340                 345                 350

Thr Ala Met Thr Ile Asn Gly Pro Trp Ala Trp Ser Asn Ile Asp Thr
            355                 360                 365

Ser Lys Val Asn Tyr Gly Val Thr Val Leu Pro Thr Phe Lys Gly Gln
            370                 375                 380

Pro Ser Lys Pro Phe Val Gly Val Leu Ser Ala Gly Ile Asn Ala Ala
385                 390                 395                 400

Ser Pro Asn Lys Glu Leu Ala Lys Glu Phe Leu Glu Asn Tyr Leu Leu
                405                 410                 415

Thr Asp Glu Gly Leu Glu Ala Val Asn Lys Asp Lys Pro Leu Gly Ala
            420                 425                 430

Val Ala Leu Lys Ser Tyr Glu Glu Leu Ala Lys Asp Pro Arg Ile
            435                 440                 445

Ala Ala Thr Met Glu Asn Ala Gln Lys Gly Glu Ile Met Pro Asn Ile
            450                 455                 460

Pro Gln Met Ser Ala Phe Trp Tyr Ala Val Arg Thr Ala Val Ile Asn
465                 470                 475                 480

Ala Ala Ser Gly Arg Gln Thr Val Asp Glu Ala Leu Lys Asp Ala Gln
                485                 490                 495

Thr Asn Ser Ser Ser
            500

<210> SEQ ID NO 56
<211> LENGTH: 256
<212> TYPE: PRT
<213> ORGANISM: Artificial sequence
<220> FEATURE:
<223> OTHER INFORMATION: SpyCatcher-SnoopCatcher

<400> SEQUENCE: 56

Met Ser Tyr Tyr His His His His His His Asp Tyr Asp Ser Ala Thr
1               5                   10                  15

His Ile Lys Phe Ser Lys Arg Asp Glu Asp Gly Lys Glu Leu Ala Gly
            20                  25                  30

Ala Thr Met Glu Leu Arg Asp Ser Ser Gly Lys Thr Ile Ser Thr Trp
        35                  40                  45

Ile Ser Asp Gly Gln Val Lys Asp Phe Tyr Leu Tyr Pro Gly Lys Tyr
    50                  55                  60

Thr Phe Val Glu Thr Ala Ala Pro Asp Gly Tyr Glu Val Ala Thr Ala
65                  70                  75                  80

Ile Thr Phe Thr Val Asn Glu Gln Gly Gln Val Thr Val Asn Gly Lys
                85                  90                  95

Ala Thr Lys Gly Asp Ala His Ile Gly Ser Pro Ala Asn Leu Lys Ala
            100                 105                 110

Leu Glu Ala Gln Lys Gln Lys Glu Gln Arg Gln Ala Ala Glu Glu Leu
        115                 120                 125
```

```
Ala Asn Ala Lys Lys Leu Lys Glu Gln Leu Glu Lys Gly Ser His Met
        130                 135                 140

Lys Pro Leu Arg Gly Ala Val Phe Ser Leu Gln Lys Gln His Pro Asp
145                 150                 155                 160

Tyr Pro Asp Ile Tyr Gly Ala Ile Asp Gln Asn Gly Thr Tyr Gln Asn
                165                 170                 175

Val Arg Thr Gly Glu Asp Gly Lys Leu Thr Phe Lys Asn Leu Ser Asp
                180                 185                 190

Gly Lys Tyr Arg Leu Phe Glu Asn Ser Glu Pro Ala Gly Tyr Lys Pro
                195                 200                 205

Val Gln Asn Lys Pro Ile Val Ala Phe Gln Ile Val Asn Gly Glu Val
                210                 215                 220

Arg Asp Val Thr Ser Ile Val Pro Gln Asp Ile Pro Ala Thr Tyr Glu
225                 230                 235                 240

Phe Thr Asn Gly Lys His Tyr Ile Thr Asn Glu Pro Ile Pro Pro Lys
                245                 250                 255
```

<210> SEQ ID NO 57
<211> LENGTH: 256
<212> TYPE: PRT
<213> ORGANISM: Artificial sequence
<220> FEATURE:
<223> OTHER INFORMATION: SnoopCatcher-SpyCatcher

<400> SEQUENCE: 57

```
Met Ser Tyr Tyr His His His His His His Lys Pro Leu Arg Gly Ala
1               5                   10                  15

Val Phe Ser Leu Gln Lys Gln His Pro Asp Tyr Pro Asp Ile Tyr Gly
                20                  25                  30

Ala Ile Asp Gln Asn Gly Thr Tyr Gln Asn Val Arg Thr Gly Glu Asp
                35                  40                  45

Gly Lys Leu Thr Phe Lys Asn Leu Ser Asp Gly Lys Tyr Arg Leu Phe
        50                  55                  60

Glu Asn Ser Glu Pro Ala Gly Tyr Lys Pro Val Gln Asn Lys Pro Ile
65                  70                  75                  80

Val Ala Phe Gln Ile Val Asn Gly Glu Val Arg Asp Val Thr Ser Ile
                85                  90                  95

Val Pro Gln Asp Ile Pro Ala Thr Tyr Glu Phe Thr Asn Gly Lys His
                100                 105                 110

Tyr Ile Thr Asn Glu Pro Ile Pro Pro Lys Gly Ser Pro Ala Asn Leu
                115                 120                 125

Lys Ala Leu Glu Ala Gln Lys Gln Lys Glu Gln Arg Gln Ala Ala Glu
        130                 135                 140

Glu Leu Ala Asn Ala Lys Lys Leu Lys Glu Gln Leu Glu Lys Gly Ser
145                 150                 155                 160

His Met Asp Tyr Asp Ser Ala Thr His Ile Lys Phe Ser Lys Arg Asp
                165                 170                 175

Glu Asp Gly Lys Glu Leu Ala Gly Ala Thr Met Glu Leu Arg Asp Ser
                180                 185                 190

Ser Gly Lys Thr Ile Ser Thr Trp Ile Ser Asp Gly Gln Val Lys Asp
        195                 200                 205

Phe Tyr Leu Tyr Pro Gly Lys Tyr Thr Phe Val Glu Thr Ala Ala Pro
        210                 215                 220

Asp Gly Tyr Glu Val Ala Thr Ala Ile Thr Phe Thr Val Asn Glu Gln
225                 230                 235                 240
```

Gly Gln Val Thr Val Asn Gly Lys Ala Thr Lys Gly Asp Ala His Ile
            245                 250                 255

<210> SEQ ID NO 58
<211> LENGTH: 86
<212> TYPE: PRT
<213> ORGANISM: Artificial sequence
<220> FEATURE:
<223> OTHER INFORMATION: SpyTag-SnoopTag

<400> SEQUENCE: 58

Met Gly Ser Ser His His His His His His Ser Ser Gly Leu Val Pro
1               5                   10                  15

Arg Gly Ser His Met Ala His Ile Val Met Val Asp Ala Tyr Lys Pro
            20                  25                  30

Thr Lys Gly Ser Pro Ala Asn Leu Lys Ala Leu Glu Ala Gln Lys Gln
        35                  40                  45

Lys Glu Gln Arg Gln Ala Ala Glu Glu Leu Ala Asn Ala Lys Lys Leu
50                  55                  60

Lys Glu Gln Leu Glu Lys Gly Ser His Met Lys Leu Gly Asp Ile Glu
65                  70                  75                  80

Phe Ile Lys Val Asn Lys
                85

<210> SEQ ID NO 59
<211> LENGTH: 86
<212> TYPE: PRT
<213> ORGANISM: Artificial sequence
<220> FEATURE:
<223> OTHER INFORMATION: SnoopTag-SpyTag

<400> SEQUENCE: 59

Met Gly Ser Ser His His His His His His Ser Ser Gly Leu Val Pro
1               5                   10                  15

Arg Gly Ser His Met Lys Leu Gly Asp Ile Glu Phe Ile Lys Val Asn
            20                  25                  30

Lys Gly Ser Pro Ala Asn Leu Lys Ala Leu Glu Ala Gln Lys Gln Lys
        35                  40                  45

Glu Gln Arg Gln Ala Ala Glu Glu Leu Ala Asn Ala Lys Lys Leu Lys
    50                  55                  60

Glu Gln Leu Glu Lys Gly Ser His Met Ala His Ile Val Met Val Asp
65                  70                  75                  80

Ala Tyr Lys Pro Thr Lys
                85

<210> SEQ ID NO 60
<211> LENGTH: 1230
<212> TYPE: DNA
<213> ORGANISM: Artificial sequence
<220> FEATURE:
<223> OTHER INFORMATION: SnoopTag-MBP

<400> SEQUENCE: 60
atgggcagca gccatcatca tcatcatcac agcagcggcc tggtgccgcg cggcagccat      60
atgggaaaac tgggcgatat tgaatttatt aaagtgaaca aaggtagtgg tgaaagtggt     120
aaaatcgaag aaggtaaaac tggtaatctg gattaacggcg ataaaggcta taacggtctc     180
gctgaagtcg gtaagaaatt cgagaaagat accggaatta agtcaccgt tgagcatccg      240 gataaactgg aagagaaatt cccacaggtt gcggcaactg gcgatggccc tgacattatc     300

```
ttctgggcac acgaccgctt tggtggctac gctcaatctg gcctgttggc tgaaatcacc      360
ccggacaaag cgttccagga caagctgtat ccgtttacct gggatgccgt acgttacaac      420
ggcaagctga ttgcttaccc gatcgctgtt gaagcgttat cgctgattta acaaagat       480 ctgctgccga acccgccaaa aacctgggaa gagatcccgg cgctggataa agaactgaaa      540
gcgaaaggta agagcgcgct gatgttcaac ctgcaagaac cgtacttcac ctggccgctg      600
attgctgctg acggggtta tgcgttcaag tatgaaaacg gcaagtacga cattaaagac       660
gtgggcgtgg ataacgctgg cgcgaaagcg ggtctgacct tcctggttga cctgattaaa      720
aacaaacaca tgaatgcaga caccgattac tccatcgcag aagctgcctt taataaaggc      780
gaaacagcga tgaccatcaa cggcccgtgg gcatggtcca acatcgacac cagcaaagtg      840
aattatggtg taacggtact gccgaccttc aagggtcaac catccaaacc gttcgttggc      900
gtgctgagcg caggtattaa cgccgccagt ccgaacaaag agctggcaaa agagttcctc      960
gaaaactatc tgctgactga tgaaggtctg gaagcggtta taaagacaa accgctgggt       1020 gccgtagcgc tgaagtctta cgaggaagag ttggcgaaag atccacgtat gccgccact       1080 atggaaaacg cccagaaagg tgaaatcatg ccgaacatcc cgcagatgtc cgctttctgg      1140
tatgccgtgc gtactgcggt gatcaacgcc gccagcggtc gtcagactgt cgatgaagcc      1200
ctgaaagacg cgcagactaa ttcgagctcg                                      1230

<210> SEQ ID NO 61
<211> LENGTH: 1527
<212> TYPE: DNA
<213> ORGANISM: Artificial sequence
<220> FEATURE:
<223> OTHER INFORMATION: SnoopCatcher-MBP

<400> SEQUENCE: 61
atgggcagca gccatcatca tcatcatcac agcagcggcc tggtgccgcg cggcagccat       60
atgaagccgc tgcgtggtgc cgtgtttagc ctgcagaaac agcatcccga ctatcccgat      120
atctatggcg cgattgatca gaatgggacc tatcaaaatg tgcgtaccgg cgaagatggt      180
aaactgacct ttaagaatct gagcgatggc aaatatcgcc tgtttgaaaa tagcgaaccc      240
gctggctata accggtgca gaataagccg attgtggcgt ttcagattgt gaatggcgaa      300
gtgcgtgatg tgaccagcat tgtgccgcag atattccgg ctacatatga atttaccaac      360
ggtaaacatt atatcaccaa tgaaccgata ccgccgaaag gtagtggtga agtggtaaa      420 atcgaagaag gtaaactggt aatctggatt aacggcgata aaggctataa cggtctcgct      480
gaagtcggta gaaattcga gaaagatacc ggaattaaag tcaccgttga gcatccggat      540
aaactggaag agaaattccc acaggttgcg gcaactggcg atggccctga cattatcttc      600
tgggcacacg accgctttgg tggctacgct caatctggcc tgttggctga atcaccccg       660 gacaaagcgt tccaggacaa gctgtatccg tttacctggg atgccgtacg ttacaacggc      720
aagctgattg cttacccgat cgctgttgaa gcgttatcgc tgatttataa caaagatctg      780
ctgccgaacc cgccaaaaac ctgggaagag atcccggcgc tggataaaga actgaaagcg      840
aaaggtaaga gcgcgctgat gttcaacctg caagaaccgt acttcacctg gccgctgatt      900
gctgctgacg ggggttatgc gttcaagtat gaaaacggca agtacgacat taaagacgtg      960
ggcgtggata cgctggcgc gaaagcgggt ctgaccttcc tggttgacct gattaaaaac      1020
aaacacatga atgcagacac cgattactcc atcgcagaag ctgcctttaa taaaggcgaa      1080
```

```
acagcgatga ccatcaacgg cccgtgggca tggtccaaca tcgacaccag caaagtgaat    1140
tatggtgtaa cggtactgcc gaccttcaag ggtcaaccat ccaaaccgtt cgttggcgtg    1200
ctgagcgcag gtattaacgc cgccagtccg aacaaagagc tggcaaaaga gttcctcgaa    1260
aactatctgc tgactgatga aggtctggaa gcggttaata agacaaacc gctgggtgcc     1320 gtagcgctga agtcttacga ggaagagttg gcgaaagatc cacgtattgc cgccactatg    1380
gaaaacgccc agaaaggtga aatcatgccg aacatcccgc agatgtccgc tttctggtat    1440
gccgtgcgta ctgcggtgat caacgccgcc agcggtcgtc agactgtcga tgaagccctg    1500
aaagacgcgc agactaattc gagctcg                                       1527
```

<210> SEQ ID NO 62
<211> LENGTH: 1233
<212> TYPE: DNA
<213> ORGANISM: Artificial sequence
<220> FEATURE:
<223> OTHER INFORMATION: PsCsTag-MBP

<400> SEQUENCE: 62

```
atgggcagca gccatcatca tcatcatcac agcagcggcc tggtgccgcg cggcagccat     60
atgggaggca acaaactgac cgtgaccgat caggcggcgc cgagcggtag tggtgaaagt    120
ggtaaaatcg aagaaggtaa actggtaatc tggattaacg gcgataaagg ctataacggt    180
ctcgctgaag tcgtaagaa attcgagaaa gataccggga ttaaagtcac cgttgagcat    240
ccggataaac tggaagagaa attcccacag gttgcggcaa ctggcgatgg ccctgacatt    300
atcttctggg cacacgaccg ctttggtggc tacgctcaat ctggcctgtt ggctgaaatc    360
accccggaca aagcgttcca ggacaagctg tatccgttta cctgggatgc cgtacgttac    420
aacggcaagc tgattgctta cccgatcgct gttgaagcgt tatcgctgat ttataacaaa    480
gatctgctgc cgaacccgcc aaaaacctgg gaagagatcc cggcgctgga taagaactg    540 aaagcgaaag gtaagagcgc gctgatgttc aacctgcaag aaccgtactt cacctggccg    600
ctgattgctg ctgacggggg ttatgcgttc aagtatgaaa acggcaagta cgacattaaa    660
gacgtgggcg tggataacgc tggcgcgaaa gcgggtctga ccttcctggt tgacctgatt    720
aaaaacaaac acatgaatgc agacaccgat tactccatcg cagaagctgc ctttaataaa    780
ggcgaaacag cgatgaccat caacggcccg tgggcatggt ccaacatcga caccagcaaa    840
gtgaattatg gtgtaacggt actgccgacc ttcaagggtc aaccatccaa accgttcgtt    900
ggcgtgctga gcgcaggtat taacgccgcc agtccgaaca aagagctggc aaaagagttc    960
ctcgaaaact atctgctgac tgatgaaggt ctggaagcgg ttaataaaga caaaccgctg    1020
ggtgccgtag cgctgaagtc ttacgaggaa gagttggcga aagatccacg tattgccgcc    1080
actatggaaa acgcccagaa aggtgaaatc atgccgaaca tcccgcagat gtccgctttc    1140
tggtatgccg tgcgtactgc ggtgatcaac gccgccagcg gtcgtcagac tgtcgatgaa    1200
gccctgaaag acgcgcagac taattcgagc tcg                                 1233
```

<210> SEQ ID NO 63
<211> LENGTH: 1464
<212> TYPE: DNA
<213> ORGANISM: Artificial sequence
<220> FEATURE:
<223> OTHER INFORMATION: PsCsCatcher-MBP

<400> SEQUENCE: 63

```
atgggcagca gccatcatca tcatcatcac agcagcggcc tggtgccgcg cggcagccat     60
```

```
atggaacagg atgtggtgtt tagcaaagtg aatgtggctg gcgaggaaat tgcgggagcg      120
aaaattcagt tgaaagacgc gcagggccag gtggtgcata gctggaccag caaagcgggc      180
caaagcgaaa ccgtgaagct gaaagccggc acctatacct tcatgaggc gagcgcaccg       240 accggctatc tggcggtgac cgatattacc tttgaagtgg atgtgcaggg caaagttaca      300
gtgaaagatg cgaatggcaa tggtgtgaaa gcggatggta gtggtaaag tggtaaaatc      360 gaagaaggta aactggtaat ctggattaac ggcgataaag ctataacgg tctcgctgaa       420 gtcggtaaga aattcgagaa agataccgga attaaagtca ccgttgagca tccggataaa      480
ctggaagaga aattcccaca ggttgcggca actggcgatg ccctgacat tatcttctgg       540 gcacacgacc gctttggtgg ctacgctcaa tctggcctgt tggctgaaat caccccggac      600
aaagcgttcc aggacaagct gtatccgttt acctgggatg ccgtacgtta acggcaag       660 ctgattgctt acccgatcgc tgttgaagcg ttatcgctga tttataacaa agatctgctg      720
ccgaacccgc caaaaacctg gaagagatc ccggcgctgg ataaagaact gaaagcgaaa       780
ggtaagagcg cgctgatgtt caacctgcaa gaaccgtact tcacctggcc gctgattgct      840
gctgacgggg ttatgcgtt caagtatgaa acggcaagt acgacattaa agacgtgggc       900
gtggataacg ctggcgcgaa agcgggtctg accttcctgg ttgacctgat aaaaacaaa      960 cacatgaatg cagacaccga ttactccatc gcagaagctg cctttaataa aggcgaaaca      1020
gcgatgacca tcaacggccc gtgggcatgg tccaacatcg acaccagcaa agtgaattat      1080
ggtgtaacgg tactgccgac cttcaagggt caaccatcca accgttcgt tggcgtgctg       1140 agcgcaggta ttaacgccgc cagtccgaac aaagagctgg caaaagagtt cctcgaaaac      1200
tatctgctga ctgatgaagg tctggaagcg gttaataaag acaaaccgct gggtgccgta      1260
gcgctgaagt cttacgagga agagttggcg aaagatccac gtattccgc cactatggaa      1320 aacgcccaga aggtgaaat catgccgaac atcccgcaga tgtccgcttt ctggtatgcc      1380
gtgcgtactg cggtgatcaa cgccgccagc ggtcgtcaga ctgtcgatga agccctgaaa      1440
gacgcgcaga ctaattcgag ctcg                                            1464
```

<210> SEQ ID NO 64
<211> LENGTH: 1251
<212> TYPE: DNA
<213> ORGANISM: Artificial sequence
<220> FEATURE:
<223> OTHER INFORMATION: RrgATag-MBP

<400> SEQUENCE: 64

```
atgggcagca gccatcatca tcatcatcac agcagcggcc tggtgccgcg cggcagccat       60
atgggagata ttccggctac atatgaattt accaacgata acattatat caccaatgaa      120 ccgggtagtg gtgaaagtgg taaaatcgaa gaaggtaaac tggtaatctg gattaacggc      180
gataaaggct ataacggtct cgctgaagtc ggtaagaaat tcgagaaaga taccggaatt      240
aaagtcaccg ttgagcatcc ggataaactg gaagagaaat tcccacaggt tgcggcaact      300
ggcgatggcc ctgacattat cttctgggca cacgaccgct ttggtggcta cgctcaatct      360
ggcctgttgg ctgaaatcac cccggacaaa gcgttccagg acaagctgta tccgtttacc      420
tgggatgccg tacgttacaa cggcaagctg attgcttacc cgatcgctgt tgaagcgtta      480
tcgctgattt ataacaaaga tctgctgccg aacccgccaa aaacctggga agagatcccg      540
gcgctggata agaactgaa agcgaaaggt aagagcgcgc tgatgttcaa cctgcaagaa      600
```

| | |
|---|---|
| ccgtacttca cctggccgct gattgctgct gacgggggtt atgcgttcaa gtatgaaaac | 660 |
| ggcaagtacg acattaaaga cgtgggcgtg gataacgctg cgcgaaagc gggtctgacc | 720 |
| ttcctggttg acctgattaa aaacaaacac atgaatgcag acaccgatta ctccatcgca | 780 |
| gaagctgcct ttaataaagg cgaaacagcg atgaccatca acggcccgtg gcatggtcc | 840 |
| aacatcgaca ccagcaaagt gaattatggt gtaacggtac tgccgacctt caagggtcaa | 900 |
| ccatccaaac cgttcgttgg cgtgctgagc gcaggtatta cgccgccag tccgaacaaa | 960 |
| gagctggcaa aagagttcct cgaaaactat ctgctgactg atgaaggtct ggaagcggtt | 1020 |
| aataaagaca aaccgctggg tgccgtagcg ctgaagtctt acgaggaaga gttggcgaaa | 1080 |
| gatccacgta ttgccgccac tatggaaaac gcccagaaag gtgaaatcat gccgaacatc | 1140 |
| ccgcagatgt ccgctttctg gtatgccgtg cgtactgcgg tgatcaacgc cgccagcggt | 1200 |
| cgtcagactg tcgatgaagc cctgaaagac gcgcagacta attcgagctc g | 1251 |

<210> SEQ ID NO 65
<211> LENGTH: 1503
<212> TYPE: DNA
<213> ORGANISM: Artificial sequence
<220> FEATURE:
<223> OTHER INFORMATION: RrgACatcherMBP

<400> SEQUENCE: 65

| | |
|---|---|
| atgggcagca gccatcatca tcatcatcac agcagcggcc tggtgccgcg cggcagccat | 60 |
| atgaaactgg gcgatattga atttattaaa gtgaacaaaa acgataaaaa gccgctgcgt | 120 |
| ggtgccgtgt ttagcctgca gaaacagcat cccgactatc cgatatcta tggcgcgatt | 180 |
| gatcagaatg ggacctatca aaatgtgcgt accggcgaag atggtaaaact gacctttaag | 240 |
| aatctgagcg atggcaaata tcgcctgttt gaaaatagcg aacccgctgg ctataaaccg | 300 |
| gtgcagaata agccgattgt ggcgtttcag attgtgaatg gcgaagtgcg tgatgtgacc | 360 |
| agcattgtgc cgcagggtag tggtaaagt ggtaaaatcg aagaaggtaa actggtaatc | 420 |
| tggattaacg gcgataaagg ctataacggt ctcgctgaag tcggtaagaa attcgagaaa | 480 |
| gataccggaa ttaaagtcac cgttgagcat ccggataaac tggaagagaa attcccacag | 540 |
| gttgcggcaa ctggcgatgg ccctgacatt atcttctggg cacacgaccg ctttggtggc | 600 |
| tacgctcaat ctggcctgtt ggctgaaatc accccggaca aagcgttcca ggacaagctg | 660 |
| tatccgttta cctgggatgc cgtacgttac aacggcaagc tgattgctta cccgatcgct | 720 |
| gttgaagcgt tatcgctgat ttataacaaa gatctgctgc cgaacccgcc aaaaacctgg | 780 |
| gaagagatcc cggcgctgga taaagaactg aaagcgaaag taagagcgc gctgatgttc | 840 |
| aacctgcaag aaccgtactt cacctggccg ctgattgctg ctgacggggg ttatgcgttc | 900 |
| aagtatgaaa acggcaagta cgacattaaa gacgtgggcg tggataacgc tggcgcgaaa | 960 |
| gcgggtctga ccttcctggt tgacctgatt aaaaacaaac acatgaatgc agacaccgat | 1020 |
| tactccatcg cagaagctgc ctttaataaa ggcgaaacag cgatgaccat caacggcccg | 1080 |
| tggcatggt ccaacatcga caccagcaaa gtgaattatg gtgtaacggt actgccgacc | 1140 |
| ttcaagggtc aaccatccaa accgttcgtt ggcgtgctga cgcaggtat taacgccgcc | 1200 |
| agtccgaaca aagagctggc aaaagagttc ctcgaaaact atctgctgac tgatgaaggt | 1260 |
| ctggaagcgg ttaataaaga caaaccgctg ggtgccgtag cgctgaagtc ttacgaggaa | 1320 |
| gagttggcga aagatccacg tattgccgcc actatggaaa acgcccagaa aggtgaaatc | 1380 |
| atgccgaaca tcccgcagat gtccgctttc tggtatgccg tgcgtactgc ggtgatcaac | 1440 |

```
gccgccagcg gtcgtcagac tgtcgatgaa gccctgaaag acgcgcagac taattcgagc    1500
tcg                                                                  1503

<210> SEQ ID NO 66
<211> LENGTH: 768
<212> TYPE: DNA
<213> ORGANISM: Artificial sequence
<220> FEATURE:
<223> OTHER INFORMATION: SpyCatcher-SnoopCatcher

<400> SEQUENCE: 66
atgtcgtact accatcacca tcaccatcac gattacgata tgctaccca tattaaattc      60 tcaaaacgtg atgaggacgg caaagagtta gctggtgcaa ctatggagtt gcgtgattca    120
tctggtaaaa ctattagtac atggatttca gatggacaag tgaaagattt ctacctgtat    180
ccaggaaaat atacatttgt cgaaaccgca gcaccagacg ttatgaggt agcaactgct     240 attacccttta cagttaatga gcaaggtcag gttactgtaa atggcaaagc aactaaaggt   300
gacgctcata ttggatcccc cgccaacctg aaggccctgg aggcccagaa gcagaaggag    360
cagagacagg ccgccgagga gctggccaac gccaagaagc tgaaggagca gctggagaag    420
ggatcccata tgaagccgct gcgtggtgcc gtgtttagcc tgcagaaaca gcatcccgac    480
tatcccgata tctatggcgc gattgatcag aatgggacct atcaaaatgt gcgtaccggc    540
gaagatggta aactgacctt taagaatctg agcgatggca atatcgcct gtttgaaaat     600 agcgaacccg ctggctataa accggtgcag aataagccga ttgtggcgtt tcagattgtg    660
aatggcgaag tgcgtgatgt gaccagcatt gtgccgcagg atattccggc tacatatgaa    720
tttaccaacg gtaaacatta tcaccaat gaaccgatac cgccgaaa                   768

<210> SEQ ID NO 67
<211> LENGTH: 768
<212> TYPE: DNA
<213> ORGANISM: Artificial sequence
<220> FEATURE:
<223> OTHER INFORMATION: SnoopCatcher-SpyCatcher

<400> SEQUENCE: 67
atgtcgtact accatcacca tcaccatcac aagccgctgc gtggtgccgt gtttagcctg     60
cagaaacagc atcccgacta tcccgatatc tatggcgcga ttgatcagaa tgggacctat    120
caaaatgtgc gtaccggcga agatggtaaa ctgaccttta agaatctgag cgatggcaaa    180
tatcgcctgt ttgaaaatag cgaacccgct ggctataaac cggtgcagaa taagccgatt    240
gtggcgtttc agattgtgaa tggcgaagtg cgtgatgtga ccagcattgt gccgcaggat    300
attccggcta catatgaatt taccaacggt aaacattata tcaccaatga accgataccg    360
ccgaaaggat cccccgccaa cctgaaggcc ctggaggccc agaagcagaa ggagcagaga    420
caggccgccg aggagctggc caacgccaag aagctgaagg agcagctgga aagggatcc    480 catatggatt acgatagtgc tacccatatt aaattctcaa acgtgatga ggacggcaaa    540 gagttagctg gtgcaactat ggagttgcgt gattcatctg gtaaaactat tagtacatgg    600
atttcagatg gacaagtgaa agatttctac ctgtatccag gaaaatatac atttgtcgaa    660
accgcagcac cagacggtta tgaggtagca actgctatta cctttacagt taatgagcaa    720
ggtcaggtta ctgtaaatgg caaagcaact aaaggtgacg ctcatatt               768

<210> SEQ ID NO 68
```

```
<211> LENGTH: 258
<212> TYPE: DNA
<213> ORGANISM: Artificial sequence
<220> FEATURE:
<223> OTHER INFORMATION: SpyTag-SnoopTag

<400> SEQUENCE: 68
atgggcagca gccatcatca tcatcatcac agcagcggcc tggtgccgcg cggcagccat    60
atggcccaca tcgtgatggt ggacgcctac aagccgacga agggatcccc cgccaacctg   120
aaggccctgg aggcccagaa gcagaaggag cagagacagg ccgccgagga gctggccaac   180
gccaagaagc tgaaggagca gctggagaag ggatcccata tgaaactggg cgatattgaa   240
tttattaaag tgaacaaa                                                  258

<210> SEQ ID NO 69
<211> LENGTH: 258
<212> TYPE: DNA
<213> ORGANISM: Artificial sequence
<220> FEATURE:
<223> OTHER INFORMATION: SnoopTag-SpyTag

<400> SEQUENCE: 69
atgggcagca gccatcatca tcatcatcac agcagcggcc tggtgccgcg cggcagccat    60
atgaaactgg gcgatattga atttattaaa gtgaacaaag atcccccgc caacctgaag    120 gccctggagg cccagaagca gaaggagcag agacaggccg ccgaggagct ggccaacgcc   180
aagaagctga aggagcagct ggagaaggga tcccatatgg cccacatcgt gatggtggac   240
gcctacaagc cgacgaag                                                  258

<210> SEQ ID NO 70
<211> LENGTH: 366
<212> TYPE: PRT
<213> ORGANISM: Artificial sequence
<220> FEATURE:
<223> OTHER INFORMATION: MBPx

<400> SEQUENCE: 70

Lys Ile Glu Glu Gly Lys Leu Val Ile Trp Ile Asn Gly Asp Lys Gly
 1               5                  10                  15

Tyr Asn Gly Leu Ala Glu Val Gly Lys Lys Phe Glu Lys Asp Thr Gly
                20                  25                  30

Ile Lys Val Thr Val Glu His Pro Asp Lys Leu Glu Glu Lys Phe Pro
            35                  40                  45

Gln Val Ala Ala Thr Gly Asp Gly Pro Asp Ile Ile Phe Trp Ala His
        50                  55                  60

Asp Arg Phe Gly Gly Tyr Ala Gln Ser Gly Leu Leu Ala Glu Ile Thr
65                  70                  75                  80

Pro Asp Lys Ala Phe Gln Asp Lys Leu Tyr Pro Phe Thr Trp Asp Ala
                85                  90                  95

Val Arg Tyr Asn Gly Lys Leu Ile Ala Tyr Pro Ile Ala Val Glu Ala
            100                 105                 110

Leu Ser Leu Ile Tyr Asn Lys Asp Leu Leu Pro Asn Pro Pro Lys Thr
        115                 120                 125

Trp Glu Glu Ile Pro Ala Leu Asp Lys Glu Leu Lys Ala Lys Gly Lys
    130                 135                 140

Ser Ala Leu Met Phe Asn Leu Gln Glu Pro Tyr Phe Thr Trp Pro Leu
145                 150                 155                 160

Ile Ala Ala Asp Gly Gly Tyr Ala Phe Lys Tyr Gly Asp Ile Lys Asp
```

```
                165                 170                 175
Val Gly Val Asp Asn Ala Gly Ala Lys Ala Gly Leu Thr Phe Leu Val
            180                 185                 190
Asp Leu Ile Lys Asn Lys His Met Asn Ala Asp Thr Asp Tyr Ser Ile
            195                 200                 205
Ala Glu Ala Ala Phe Asn Lys Gly Glu Thr Ala Met Thr Ile Asn Gly
            210                 215                 220
Pro Trp Ala Trp Ser Asn Ile Asp Thr Ser Lys Val Asn Tyr Gly Val
225                 230                 235                 240
Thr Val Leu Pro Thr Phe Lys Gly Gln Pro Ser Lys Pro Phe Val Gly
            245                 250                 255
Val Leu Ser Ala Gly Ile Asn Ala Ala Ser Pro Asn Lys Glu Leu Ala
            260                 265                 270
Lys Glu Phe Leu Glu Asn Tyr Leu Leu Thr Asp Glu Gly Leu Glu Ala
            275                 280                 285
Val Asn Lys Asp Lys Pro Leu Gly Ala Val Ala Leu Lys Ser Tyr Glu
            290                 295                 300
Glu Glu Leu Val Lys Asp Pro Arg Val Ala Ala Thr Met Glu Asn Ala
305                 310                 315                 320
Gln Lys Gly Glu Ile Met Pro Asn Ile Pro Gln Met Ser Ala Phe Trp
            325                 330                 335
Tyr Ala Val Arg Thr Ala Val Ile Asn Ala Ala Ser Gly Arg Gln Thr
            340                 345                 350
Val Asp Glu Ala Leu Lys Asp Ala Gln Thr Asn Ser Ser Ser
            355                 360                 365

<210> SEQ ID NO 71
<211> LENGTH: 1098
<212> TYPE: DNA
<213> ORGANISM: Artificial sequence
<220> FEATURE:
<223> OTHER INFORMATION: MBPx

<400> SEQUENCE: 71
aaaatcgaag aaggtaaaact ggtaatctgg attaacggcg ataaaggcta taacggtctc    60
gctgaagtcg gtaagaaatt cgagaaagat accggaatta aagtcaccgt tgagcatccg   120
gataaactgg aagagaaatt cccacaggtt gcggcaactg gcgatggccc tgacattatc   180
ttctgggcac acgaccgctt tggtggctac gctcaatctg gcctgttggc tgaaatcacc   240
ccggacaaag cgttccagga caagctgtat ccgtttacct gggatgccgt acgttacaac   300
ggcaagctga ttgcttaccc gatcgctgtt gaagcgttat cgctgattta acaaagat    360 ctgctgccga acccgccaaa aacctgggaa gagatcccgg cgctggataa agaactgaaa   420
gcgaaaggta gagcgcgct gatgttcaac ctgcaagaac cgtacttcac ctggccgctg   480
attgctgctg acgggggtta tgcgttcaag tatggcgaca ttaaagacgt gggcgtggat   540
aacgctggcg cgaaagcggg tctgaccttc ctggttgacc tgattaaaaa caaacacatg   600
aatgcagaca ccgattactc catcgcagaa gctgccttta taaaggcga acagcgatg   660 accatcaacg gcccgtgggc atggtccaac atcgacacca gcaaagtgaa ttatggtgta   720
acggtactgc cgaccttcaa gggtcaacca tccaaaccgt tcgttggcgt gctgagcgca   780
ggtattaacg ccgccagtcc gaacaaagag ctggcaaaag agttcctcga aaactatctg   840
ctgactgatg aaggtctgga agcggttaat aaagacaaac gctgggtgc cgtagcgctg   900 aagtcttacg aggaagagtt ggtgaaagat ccacgtgtgg ccgccactat ggaaaacgcc   960
```

```
cagaaaggtg aaatcatgcc gaacatcccg cagatgtccg ctttctggta tgccgtgcgt    1020
actgcggtga tcaacgccgc cagcggtcgt cagactgtcg atgaagccct gaaagacgcg    1080
cagacgaatt ctagttcc                                                  1098
```

<210> SEQ ID NO 72
<211> LENGTH: 137
<212> TYPE: PRT
<213> ORGANISM: Artificial sequence
<220> FEATURE:
<223> OTHER INFORMATION: SnoopTag-AffiHER2-SpyTag

<400> SEQUENCE: 72

```
Met Gly Ser Ser His His His His His His Ser Ser Gly Leu Val Pro
1               5                   10                  15

Arg Gly Ser His Met Gly Lys Leu Gly Asp Ile Glu Phe Ile Lys Val
            20                  25                  30

Asn Lys Gly Ser Gly Glu Ser Gly Ser Gly Ala Ser Met Thr Gly Gly
        35                  40                  45

Gln Gln Met Gly Arg Asp Pro Gly Val Asp Asn Lys Phe Asn Lys Glu
    50                  55                  60

Met Arg Asn Ala Tyr Trp Glu Ile Ala Leu Leu Pro Asn Leu Asn Asn
65                  70                  75                  80

Gln Gln Lys Arg Ala Phe Ile Arg Ser Leu Tyr Asp Asp Pro Ser Gln
                85                  90                  95

Ser Ala Asn Leu Leu Ala Glu Ala Lys Lys Leu Asn Asp Ala Gln Ala
            100                 105                 110

Pro Lys Gly Leu Glu Gly Ser Gly Glu Gly Ser Gly Ala His Ile Val
        115                 120                 125

Met Val Asp Ala Tyr Lys Pro Thr Lys
    130                 135
```

<210> SEQ ID NO 73
<211> LENGTH: 40
<212> TYPE: DNA
<213> ORGANISM: Artificial sequence
<220> FEATURE:
<223> OTHER INFORMATION: Primer

<400> SEQUENCE: 73

```
gtgccgcagg atattccggc tacatatgaa tttaccaacg                           40
```

<210> SEQ ID NO 74
<211> LENGTH: 47
<212> TYPE: DNA
<213> ORGANISM: Artificial sequence
<220> FEATURE:
<223> OTHER INFORMATION: Primer

<400> SEQUENCE: 74

```
gctacatatg aatttaccaa cggtaaacat tatatcacca atgaacc                   47
```

<210> SEQ ID NO 75
<211> LENGTH: 31
<212> TYPE: DNA
<213> ORGANISM: Artificial sequence
<220> FEATURE:
<223> OTHER INFORMATION: Primer

<400> SEQUENCE: 75

```
acattatatc accgctgaac cgataccgcc g                                    31
```

<210> SEQ ID NO 76
<211> LENGTH: 31
<212> TYPE: DNA
<213> ORGANISM: Artificial sequence
<220> FEATURE:
<223> OTHER INFORMATION: Primer

<400> SEQUENCE: 76
ggtagtggtg aaagtggtaa atcgaagaa g                              31

<210> SEQ ID NO 77
<211> LENGTH: 76
<212> TYPE: DNA
<213> ORGANISM: Artificial sequence
<220> FEATURE:
<223> OTHER INFORMATION: Primer

<400> SEQUENCE: 77
aaactgggcg atattgaatt tattaaagtg aacaaaaacg ataaaggtag tggtgaaagt    60
ggtaaaatcg aagaag                                              76

<210> SEQ ID NO 78
<211> LENGTH: 20
<212> TYPE: DNA
<213> ORGANISM: Artificial sequence
<220> FEATURE:
<223> OTHER INFORMATION: Primer

<400> SEQUENCE: 78
tcccatatgg ctgccgcgcg                                          20

<210> SEQ ID NO 79
<211> LENGTH: 65
<212> TYPE: DNA
<213> ORGANISM: Artificial sequence
<220> FEATURE:
<223> OTHER INFORMATION: Primer

<400> SEQUENCE: 79
tttatcgttt ttgttcactt taataaattc aatatcgccc agttttccca tatggctgcc    60
gcgcg                                                          65

<210> SEQ ID NO 80
<211> LENGTH: 46
<212> TYPE: DNA
<213> ORGANISM: Artificial sequence
<220> FEATURE:
<223> OTHER INFORMATION: Primer

<400> SEQUENCE: 80
gaatttatta aagtgaacaa aggtagtggt gaaagtggta aaatcg              46

<210> SEQ ID NO 81
<211> LENGTH: 39
<212> TYPE: DNA
<213> ORGANISM: Artificial sequence
<220> FEATURE:
<223> OTHER INFORMATION: Primer

<400> SEQUENCE: 81
gggcgatatt gaatttattg cagtgaacaa aggtagtgg                     39

<210> SEQ ID NO 82

<210> SEQ ID NO 82
<211> LENGTH: 57
<212> TYPE: DNA
<213> ORGANISM: Artificial sequence
<220> FEATURE:
<223> OTHER INFORMATION: Primer

<400> SEQUENCE: 82
gttcgggcgg tagtggtgcc atggttgata ccttatcagg tttatcaagt gagcaag        57

<210> SEQ ID NO 83
<211> LENGTH: 54
<212> TYPE: DNA
<213> ORGANISM: Artificial sequence
<220> FEATURE:
<223> OTHER INFORMATION: Primer

<400> SEQUENCE: 83
tactaagctt ctattaaata tgagcgtcac ctttagttgc tttgccattt acag           54

<210> SEQ ID NO 84
<211> LENGTH: 37
<212> TYPE: DNA
<213> ORGANISM: Artificial sequence
<220> FEATURE:
<223> OTHER INFORMATION: Primer

<400> SEQUENCE: 84
atctcatatg ggcagcagcc atcatcatca tcatcac                              37

<210> SEQ ID NO 85
<211> LENGTH: 52
<212> TYPE: DNA
<213> ORGANISM: Artificial sequence
<220> FEATURE:
<223> OTHER INFORMATION: Primer

<400> SEQUENCE: 85
gtatcaacca tggcaccact accgcccgaa cccgagctcg aattagtctg cg             52

<210> SEQ ID NO 86
<211> LENGTH: 57
<212> TYPE: DNA
<213> ORGANISM: Artificial sequence
<220> FEATURE:
<223> OTHER INFORMATION: Primer

<400> SEQUENCE: 86
gtcttacgag gaagagttgg tgaaagatcc acgtgtggcc gccactatgg aaaacgc        57

<210> SEQ ID NO 87
<211> LENGTH: 41
<212> TYPE: DNA
<213> ORGANISM: Artificial sequence
<220> FEATURE:
<223> OTHER INFORMATION: Primer

<400> SEQUENCE: 87
gggttatgcg ttcaagtatg gcgacattaa agacgtgggc g                         41

<210> SEQ ID NO 88
<211> LENGTH: 47
<212> TYPE: DNA
<213> ORGANISM: Artificial sequence
<220> FEATURE:
<223> OTHER INFORMATION: Primer

<400> SEQUENCE: 88

```
caccatcacc atcacgatta cgatagtgct acccatatta aattctc                    47
```

<210> SEQ ID NO 89
<211> LENGTH: 54
<212> TYPE: DNA
<213> ORGANISM: Artificial sequence
<220> FEATURE:
<223> OTHER INFORMATION: Primer

<400> SEQUENCE: 89

```
ggcggatccg gaggtggatc cggaaagata gaggagggta aactggtaat ctgg          54
```

<210> SEQ ID NO 90
<211> LENGTH: 25
<212> TYPE: DNA
<213> ORGANISM: Artificial sequence
<220> FEATURE:
<223> OTHER INFORMATION: Primer

<400> SEQUENCE: 90

```
cctatagtga gtcgtattaa tttcg                                           25
```

<210> SEQ ID NO 91
<211> LENGTH: 25
<212> TYPE: DNA
<213> ORGANISM: Artificial sequence
<220> FEATURE:
<223> OTHER INFORMATION: Primer

<400> SEQUENCE: 91

```
cgaaattaat acgactcact atagg                                           25
```

<210> SEQ ID NO 92
<211> LENGTH: 55
<212> TYPE: DNA
<213> ORGANISM: Artificial sequence
<220> FEATURE:
<223> OTHER INFORMATION: Primer

<400> SEQUENCE: 92

```
tccggatcca cctccggatc cgccggaact agaattcgtc tgcgcgtctt tcagg         55
```

<210> SEQ ID NO 93
<211> LENGTH: 34
<212> TYPE: PRT
<213> ORGANISM: Artificial sequence
<220> FEATURE:
<223> OTHER INFORMATION: Helical linker

<400> SEQUENCE: 93

Pro Ala Asn Leu Lys Ala Leu Glu Ala Gln Lys Gln Lys Glu Gln Arg
1               5                   10                  15

Gln Ala Ala Glu Glu Leu Ala Asn Ala Lys Lys Leu Lys Glu Gln Leu
            20                  25                  30

Glu Lys

<210> SEQ ID NO 94
<211> LENGTH: 43
<212> TYPE: DNA
<213> ORGANISM: Artificial sequence
<220> FEATURE:
<223> OTHER INFORMATION: Primer

<400> SEQUENCE: 94
ctttaagaag gagatataca tatgtcgtac taccatcacc atc                43

<210> SEQ ID NO 95
<211> LENGTH: 40
<212> TYPE: DNA
<213> ORGANISM: Artificial sequence
<220> FEATURE:
<223> OTHER INFORMATION: Primer

<400> SEQUENCE: 95
ccgctgcttc cggatccaat atgagcgtca cctttagttg                    40

<210> SEQ ID NO 96
<211> LENGTH: 58
<212> TYPE: DNA
<213> ORGANISM: Artificial sequence
<220> FEATURE:
<223> OTHER INFORMATION: Primer

<400> SEQUENCE: 96
catattggat ccggaagcag cggcctggtg ccgcgcggat cccatatgaa gccgctgc    58

<210> SEQ ID NO 97
<211> LENGTH: 45
<212> TYPE: DNA
<213> ORGANISM: Artificial sequence
<220> FEATURE:
<223> OTHER INFORMATION: Primer

<400> SEQUENCE: 97
gtggtggtgg tggtgctcga gttattattt cggcggtatc ggttc              45

<210> SEQ ID NO 98
<211> LENGTH: 90
<212> TYPE: DNA
<213> ORGANISM: Artificial sequence
<220> FEATURE:
<223> OTHER INFORMATION: Primer

<400> SEQUENCE: 98
ctaaaggtga cgctcatatt ggatcccccg ccaacctgaa ggccctggag gcccagaagc    60
agaaggagca gagacaggcc gccgaggagc                               90

<210> SEQ ID NO 99
<211> LENGTH: 89
<212> TYPE: DNA
<213> ORGANISM: Artificial sequence
<220> FEATURE:
<223> OTHER INFORMATION: Primer

<400> SEQUENCE: 99
cacggcacca cgcagcggct tcatatggga tcccttctcc agctgctcct tcagcttctt    60
ggcgttggcc agctcctcgg cggcctgtc                                89

<210> SEQ ID NO 100
<211> LENGTH: 47
<212> TYPE: DNA
<213> ORGANISM: Artificial sequence
<220> FEATURE:
<223> OTHER INFORMATION: Primer

<400> SEQUENCE: 100
caccatcacc atcacgatta cgatagtgct acccatatta aattctc             47

```
<210> SEQ ID NO 101
<211> LENGTH: 50
<212> TYPE: DNA
<213> ORGANISM: Artificial sequence
<220> FEATURE:
<223> OTHER INFORMATION: Primer

<400> SEQUENCE: 101
gtgaacaaag gcagtggtga gtcgggatcc ggagctagca tgactggtgg         50

<210> SEQ ID NO 102
<211> LENGTH: 51
<212> TYPE: DNA
<213> ORGANISM: Artificial sequence
<220> FEATURE:
<223> OTHER INFORMATION: Primer

<400> SEQUENCE: 102
catcacgatg tgggcaccgg aaccttcccc ggatccctcg aggcctttcg g        51

<210> SEQ ID NO 103
<211> LENGTH: 71
<212> TYPE: DNA
<213> ORGANISM: Artificial sequence
<220> FEATURE:
<223> OTHER INFORMATION: Primer

<400> SEQUENCE: 103
ctacccaacc taaacggggt acaagtaaag gctttcatag actcgctaag ggatgaccca    60
agccaaagcg c                                                         71

<210> SEQ ID NO 104
<211> LENGTH: 81
<212> TYPE: DNA
<213> ORGANISM: Artificial sequence
<220> FEATURE:
<223> OTHER INFORMATION: Primer

<400> SEQUENCE: 104
gttgaatatc tcccaagtag cccaccctag ctccttgttg aacttgttgt ctacttcttt    60
gttgaatttg ttgtccacgc c                                              81

<210> SEQ ID NO 105
<211> LENGTH: 30
<212> TYPE: DNA
<213> ORGANISM: Artificial sequence
<220> FEATURE:
<223> OTHER INFORMATION: Primer

<400> SEQUENCE: 105
gattacgaca tcccaacgac cgaaaacctg                                     30

<210> SEQ ID NO 106
<211> LENGTH: 77
<212> TYPE: DNA
<213> ORGANISM: Artificial sequence
<220> FEATURE:
<223> OTHER INFORMATION: Primer

<400> SEQUENCE: 106
gcctgaacga tatttttgaa gcgcagaaaa ttgaatggca tgaaggcgat tacgacatcc    60
caacgaccga aaacctg                                                   77

<210> SEQ ID NO 107
```

```
<211> LENGTH: 33
<212> TYPE: DNA
<213> ORGANISM: Artificial sequence
<220> FEATURE:
<223> OTHER INFORMATION: Primer

<400> SEQUENCE: 107
gtgatggtga tggtgatggt agtacgacat atg                                33

<210> SEQ ID NO 108
<211> LENGTH: 80
<212> TYPE: DNA
<213> ORGANISM: Artificial sequence
<220> FEATURE:
<223> OTHER INFORMATION: Primer

<400> SEQUENCE: 108
tgccattcaa ttttctgcgc ttcaaaaata tcgttcaggc cgctgccgtg atggtgatgg   60
tgatggtagt acgacatatg                                               80

<210> SEQ ID NO 109
<211> LENGTH: 23
<212> TYPE: PRT
<213> ORGANISM: Artificial sequence
<220> FEATURE:
<223> OTHER INFORMATION: RrgATag2

<400> SEQUENCE: 109

Asp Ile Pro Ala Thr Tyr Glu Phe Thr Asn Gly Lys His Tyr Ile Thr
1               5                   10                  15

Asn Glu Pro Ile Pro Pro Lys
            20

<210> SEQ ID NO 110
<211> LENGTH: 69
<212> TYPE: DNA
<213> ORGANISM: Artificial Sequence
<220> FEATURE:
<223> OTHER INFORMATION: RrgATag2

<400> SEQUENCE: 110
gatattccgg ctacatatga atttaccaac ggtaaacatt atatcaccaa tgaaccgata   60
ccgccgaaa                                                           69

<210> SEQ ID NO 111
<211> LENGTH: 19
<212> TYPE: PRT
<213> ORGANISM: Artificial Sequence
<220> FEATURE:
<223> OTHER INFORMATION: RrgATag2.0

<400> SEQUENCE: 111

Asp Ile Pro Ala Thr Tyr Glu Phe Thr Asn Gly Lys His Tyr Ile Thr
1               5                   10                  15

Asn Glu Pro

<210> SEQ ID NO 112
<211> LENGTH: 57
<212> TYPE: DNA
<213> ORGANISM: Artificial Sequence
<220> FEATURE:
<223> OTHER INFORMATION: RrgATag2.0

<400> SEQUENCE: 112
```

```
gatattccgg ctacatatga atttaccaac ggtaaacatt atatcaccaa tgaaccg      57
```

<210> SEQ ID NO 113
<211> LENGTH: 18
<212> TYPE: PRT
<213> ORGANISM: Artificial Sequence
<220> FEATURE:
<223> OTHER INFORMATION: RrgATag2.1

<400> SEQUENCE: 113

Asp Ile Pro Ala Thr Tyr Glu Phe Thr Asn Gly Lys His Tyr Ile Thr
1               5                   10                  15

Asn Glu

<210> SEQ ID NO 114
<211> LENGTH: 54
<212> TYPE: DNA
<213> ORGANISM: Artificial Sequence
<220> FEATURE:
<223> OTHER INFORMATION: RrgATag2.1

<400> SEQUENCE: 114

```
gatattccgg ctacatatga atttaccaac ggtaaacatt atatcaccaa tgaa         54
```

<210> SEQ ID NO 115
<211> LENGTH: 17
<212> TYPE: PRT
<213> ORGANISM: Artificial Sequence
<220> FEATURE:
<223> OTHER INFORMATION: RrgATag2.2

<400> SEQUENCE: 115

Asp Ile Pro Ala Thr Tyr Glu Phe Thr Asn Gly Lys His Tyr Ile Thr
1               5                   10                  15

Asn

<210> SEQ ID NO 116
<211> LENGTH: 51
<212> TYPE: DNA
<213> ORGANISM: Artificial Sequence
<220> FEATURE:
<223> OTHER INFORMATION: RrgATag2.2

<400> SEQUENCE: 116

```
gatattccgg ctacatatga atttaccaac ggtaaacatt atatcaccaa t            51
```

<210> SEQ ID NO 117
<211> LENGTH: 16
<212> TYPE: PRT
<213> ORGANISM: Artificial Sequence
<220> FEATURE:
<223> OTHER INFORMATION: RrgATag2.3

<400> SEQUENCE: 117

Ala Thr Tyr Glu Phe Thr Asn Gly Lys His Tyr Ile Thr Asn Glu Pro
1               5                   10                  15

<210> SEQ ID NO 118
<211> LENGTH: 48
<212> TYPE: DNA
<213> ORGANISM: Artificial Sequence
<220> FEATURE:
<223> OTHER INFORMATION: RrgATag2.3

<400> SEQUENCE: 118
gctacatatg aatttaccaa cggtaaacat tatatcacca atgaaccg 48

<210> SEQ ID NO 119
<211> LENGTH: 8
<212> TYPE: PRT
<213> ORGANISM: Artificial Sequence
<220> FEATURE:
<223> OTHER INFORMATION: RrgATag2.4

<400> SEQUENCE: 119

Lys His Tyr Ile Thr Asn Glu Pro
1               5

<210> SEQ ID NO 120
<211> LENGTH: 24
<212> TYPE: DNA
<213> ORGANISM: Artificial Sequence
<220> FEATURE:
<223> OTHER INFORMATION: RrgATag2.4

<400> SEQUENCE: 120
aaacattata tcaccaatga accg 24

<210> SEQ ID NO 121
<211> LENGTH: 9
<212> TYPE: PRT
<213> ORGANISM: Artificial Sequence
<220> FEATURE:
<223> OTHER INFORMATION: RrgATag2.5

<400> SEQUENCE: 121

Gly Lys His Tyr Ile Thr Asn Glu Pro
1               5

<210> SEQ ID NO 122
<211> LENGTH: 27
<212> TYPE: DNA
<213> ORGANISM: Artificial Sequence
<220> FEATURE:
<223> OTHER INFORMATION: RrgATag2.5

<400> SEQUENCE: 122
ggtaaacatt atatcaccaa tgaaccg 27

<210> SEQ ID NO 123
<211> LENGTH: 10
<212> TYPE: PRT
<213> ORGANISM: Artificial Sequence
<220> FEATURE:
<223> OTHER INFORMATION: RrgATag2.6

<400> SEQUENCE: 123

Asn Gly Lys His Tyr Ile Thr Asn Glu Pro
1               5                   10

<210> SEQ ID NO 124
<211> LENGTH: 30
<212> TYPE: DNA
<213> ORGANISM: Artificial Sequence
<220> FEATURE:
<223> OTHER INFORMATION: RrgATag2.6

<400> SEQUENCE: 124
aacggtaaac attatatcac caatgaaccg 30

<210> SEQ ID NO 125

```
<211> LENGTH: 23
<212> TYPE: PRT
<213> ORGANISM: Artificial Sequence
<220> FEATURE:
<223> OTHER INFORMATION: RrgATag2.7

<400> SEQUENCE: 125

Ile Val Pro Gln Asp Ile Pro Ala Thr Tyr Glu Phe Thr Asn Gly Lys
1               5                   10                  15

His Tyr Ile Thr Asn Glu Pro
            20

<210> SEQ ID NO 126
<211> LENGTH: 69
<212> TYPE: DNA
<213> ORGANISM: Artificial Sequence
<220> FEATURE:
<223> OTHER INFORMATION: RrgATag2.7

<400> SEQUENCE: 126
attgtaccgc aggatattcc ggctacatat gaatttacca acggtaaaca ttatatcacc      60
aatgaaccg                                                             69
```

METHODS AND PRODUCTS FOR FUSION PROTEIN SYNTHESIS

CROSS-REFERENCE

This application is a section 371 U.S. National phase of PCT/GB2016/051640, filed Jun. 3, 2016 which claims priority from GB 1509782.7, filed Jun. 5, 2015, which is incorporated by reference in its entirety.

FIELD OF INVENTION

The present invention relates to the synthesis (i.e. production, generation or assembly) of a fusion protein (i.e. a polymer comprising two or more covalently linked proteins, as defined below) and in particular to the modular (e.g. step-wise) synthesis of a fusion protein using orthogonal pairs of peptide linkers which react to form isopeptide bonds. The invention concerns the provision of a new method for synthesizing fusion proteins, particularly solid-phase synthesis. The method can advantageously be used in the production of a variety of products comprising fusion proteins, e.g. fusion protein arrays. The present invention also provides peptide linkers and the use of orthogonal pairs of said linkers in the synthesis of fusion proteins. Recombinant proteins comprising said linkers, nucleic acid molecules encoding said proteins and linkers, vectors comprising said nucleic acid molecules and host cells comprising said vectors and nucleic acid molecules are also provided. A kit comprising said recombinant polypeptides and/or nucleic acid molecules/vectors is also provided. Fusion proteins obtained by the method of the invention and products, e.g. arrays and libraries, comprising said fusions proteins are also contemplated.

BACKGROUND OF THE INVENTION

Biological events usually depend on the cooperative activity of multiple proteins and the precise arrangement of proteins in complexes influences and determines their function. Thus, the ability to arrange individual proteins in a complex in a controlled manner represents a useful tool in characterising protein functions. Moreover, the conjugation of multiple proteins to form a so-called "fusion protein" can result in molecules with useful characteristics. For instance, clustering a single kind of protein often greatly enhances biological signals, e.g. the repeating antigen structures on vaccines. Clustering proteins with different activities can also result in complexes with improved activities, e.g. substrate channelling by enzymes.

However, clustering different kinds of proteins into precise artificial "fusion proteins" has encountered numerous problems. For instance, individual proteins or protein domains can be joined genetically into one long open reading frame, but errors in protein synthesis and misfolding soon become limiting. Alternative methods have focussed on expressing proteins or protein domains individually and then linking these "modules" or "units" together. For instance, methods have focussed on modifying proteins to contain well characterised interaction partners, such as biotin/avidin, thereby enabling proteins to form complexes through non-covalent interactions. Other methods have relied on reactive groups within the proteins, particularly cysteine residues, to link proteins through covalent bonds, i.e. disulfide bridges. However, even the best non-covalent linkages or reversible covalent linkages allow the rearrangement of fusion proteins. Accordingly, existing methods are limited, insofar as they commonly result in undefined mixtures of fusion proteins that are difficult to separate and/or fusion proteins that are not stable across a variety of environments, e.g. in reducing conditions.

Important features of a system for synthesizing fusion proteins include molecularly-defined connections between the individual proteins (i.e. modules, domains or units) within said fusion protein, independence from any template, and simple expression of each protein (i.e. module, domain or unit). It is also highly desirable to have a near quantitative yield for each reaction to minimize the inadvertent synthesis of heterogeneous products after just a few steps, which is a common consequence of incomplete chains within the mixture. It is also preferable for individual modules to be modified with relatively small peptide tags rather than large protein fusion domains, for minimal disruption to the function of each module within the fusion protein. However, no existing fusion protein synthesis method has been able to fulfil these criteria.

Thus, there is a need and desire for an improved method for synthesizing fusion proteins and it has now been found that peptide linkers that form isopeptide bonds to generate irreversible covalent linkages can be used in a modular (e.g. step-wise), and high-yielding, method for synthesizing a fusion protein.

SUMMARY OF THE INVENTION

Isopeptide bonds are amide bonds formed between carboxyl/carboxamide and amino groups, where at least one of the carboxyl or amino groups is outside of the protein main-chain (the backbone of the protein). Such bonds are chemically irreversible under biological conditions and they are resistant to most proteases. In fact, isopeptide bonds between proteins have been determined to be the strongest measured protein interaction.

Isopeptide bond formation can be enzyme catalyzed, for example by transglutaminase enzymes. Isopeptide bonds are commonly found in natural environments to improve the strength and/or stability of a protein complex, e.g. the stabilization of extracellular matrix structures or reinforcement of blood clots.

Isopeptide bonds may also form spontaneously as has been identified in HK97 bacteriophage capsid formation and Gram-positive bacterial pili. Spontaneous isopeptide bond formation has been proposed to occur after protein folding, through nucleophilic attack of the ε-amino group from a lysine on the Cγ group of an asparagine or aspartate, promoted by a nearby glutamate or aspartate.

Proteins that are capable of spontaneous isopeptide bond formation have been advantageously used to develop peptide tag/binding partner pairs which covalently bind to each other and which hence provide irreversible interactions (see e.g. WO2011/098772 herein incorporated by reference). In this respect, proteins which are capable of spontaneous isopeptide bond formation may be expressed as separate fragments, to give a peptide tag and a binding partner for the peptide tag, where the two fragments are capable of covalently reconstituting by isopeptide bond formation. The isopeptide bond formed by the peptide tag and binding partner pairs is stable under conditions where non-covalent interactions would rapidly dissociate, e.g. over long periods of time (e.g. weeks), at high temperature (to at least 95° C.), at high force, or with harsh chemical treatment (e.g. pH 2-11, organic solvent, detergents or denaturants).

In brief, a peptide tag/binding partner pair may be derived from any protein capable of spontaneously forming an isopeptide bond (an isopeptide protein), wherein the domains of the protein are expressed separately to produce a peptide tag that comprises one of the residues involved in the isopeptide bond (e.g. a lysine) and a peptide binding partner that comprises the other residue involved in the isopeptide bond (e.g. an asparagine or aspartate). In some instances, one of the peptide tag or binding partner comprises one or more other residues required to form the isopeptide bond (e.g. a glutamate). However, it has been found that it is possible to express the domains comprising the residues involved in isopeptide bond formation separately, i.e. as three separate peptides (domains, modules or units). In this respect, the peptide tag comprises one of the residues involved in the isopeptide bond (e.g. a lysine), the peptide binding partner that comprises the other residue involved in the isopeptide bond (e.g. an asparagine or aspartate) and a third peptide comprises the one or more other residues involved in isopeptide bond formation (e.g. a glutamate). Mixing all three peptides results in the formation of an isopeptide bond between the two peptides comprising the residues that react to form the isopeptide bond, i.e. the peptide tag and binding partner. Thus, the third peptide mediates the conjugation of the peptide tag and binding partner but does not form of the part resultant structure, i.e. the third peptide is not covalently linked to the peptide tag or binding partner. As such, the third peptide may be viewed as a protein ligase or peptide ligase. This is particularly useful as it minimises the size of the peptide tag and binding partner that need to be fused to the protein of interest, thereby reducing the possibility of unwanted interactions caused by the addition of the peptide tag or binding partner, e.g. misfolding.

As discussed in more detail below, various proteins which are capable of spontaneously forming one or more isopeptide bonds (a so-called "isopeptide protein") have been identified and may be modified to produce a peptide tag/binding partner pair and optionally a peptide ligase, as discussed above. Further proteins that are capable of spontaneously forming one or more isopeptide bonds may be identified by comparing their structures with those of proteins which are known to spontaneously form one or more isopeptide bonds. Particularly, other proteins which may spontaneously form an isopeptide bond may be identified by comparing their crystal structures with those from known isopeptide proteins e.g. the major pilin protein Spy0128, and in particular comparing the Lys-Asn/Asp-Glu/Asp residues often involved in the formation of an isopeptide protein. Additionally, other isopeptide proteins may be identified by screening for structural homologues of known isopeptide proteins using the Protein Data Bank using standard database searching tools. The SPASM server may be used to target the 3D structural template of Lys-Asn/Asp-Glu/Asp of the isopeptide bond or isopeptide proteins may also be identified by sequence homology alone.

Notably, proteins which form isopeptide bonds may be designed de novo as described in WO2011/098772 (herein incorporated by reference). Rosetta can be used to design isopeptide proteins de novo. (See also Macromolecular modeling with rosetta, Das. R, Baker. D, Annu Rev Biochem, 2008, 77, 363-82). Additionally, the RASMOT-3D PRO server can be used to search the protein database for appropriate orientation of residues.

The present inventors have advantageously determined that such peptide tag/binding partner pairs may be used as peptide linkers to covalently join multiple proteins, i.e. to produce a fusion protein. In particular, the inventors have demonstrated that orthogonal (i.e. mutually unreactive or non-cognate) pairs of peptide tag/binding partner peptides find utility in the fusion (e.g. conjugation, linkage) of two or more proteins, i.e. the production (synthesis, construction, assembly) of fusion proteins. As demonstrated in detail in the Examples below, the methods and uses of the present invention provide a modular (e.g. step-wise) and high yielding approach to link proteins into chains based upon sequential isopeptide bond formation. In particular, the methods and uses described herein enable the controlled (i.e. specific, targeted) extension of protein chains without the generation of statistical mixtures. It is particularly advantageous over previous methods because it results in a fusion protein in which each protein unit (module, domain) is joined by an irreversible linkage, i.e. an isopeptide bond. Thus, as the linkage is not reliant on the reaction of cysteine residues, it is applicable to proteins that contain free cysteine residues and/or disulfide bonds. Furthermore, each protein unit to be added to the chain needs to be modified only with two small peptide tags, which can be incorporated at various positions within the protein, i.e. at the N-terminus, C-terminus or at an internal site on the protein. Thus, each protein unit of the fusion protein may be completely genetically encoded, i.e. the method is not reliant on the use of unnatural (i.e. non-standard) amino acids or the post-translational modification of amino acid residues. Thus, the present invention provides a simple and scalable method for the synthesis of fusion proteins which is highly specific and does not require purification of intermediates.

DESCRIPTION OF THE DRAWINGS

The invention will now be described in more detail in the following non-limiting Example below with reference to the following drawings.

a graph depicting the TMAO-dependence of the isopeptide bond formation between SnoopTag-MBP and SnoopCatcher.

Figure 7:
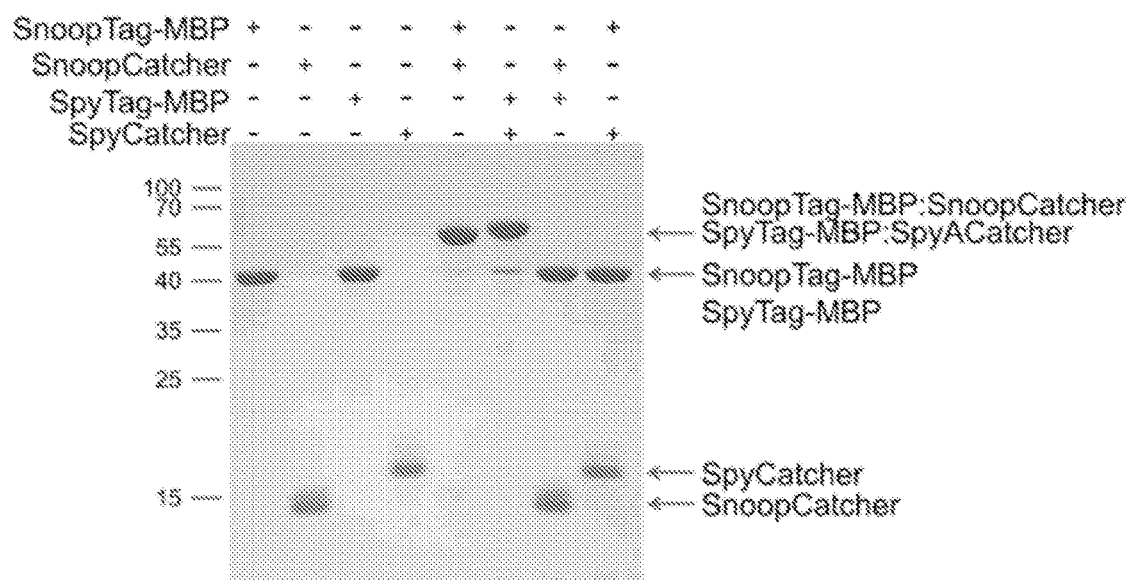

FIG. 7 shows a picture of an SDS-PAGE gel with Coomassie staining characterising SnoopTag/SnoopCatcher and SpyTag/SpyCatcher orthogonal reactivity.

Figure 8:
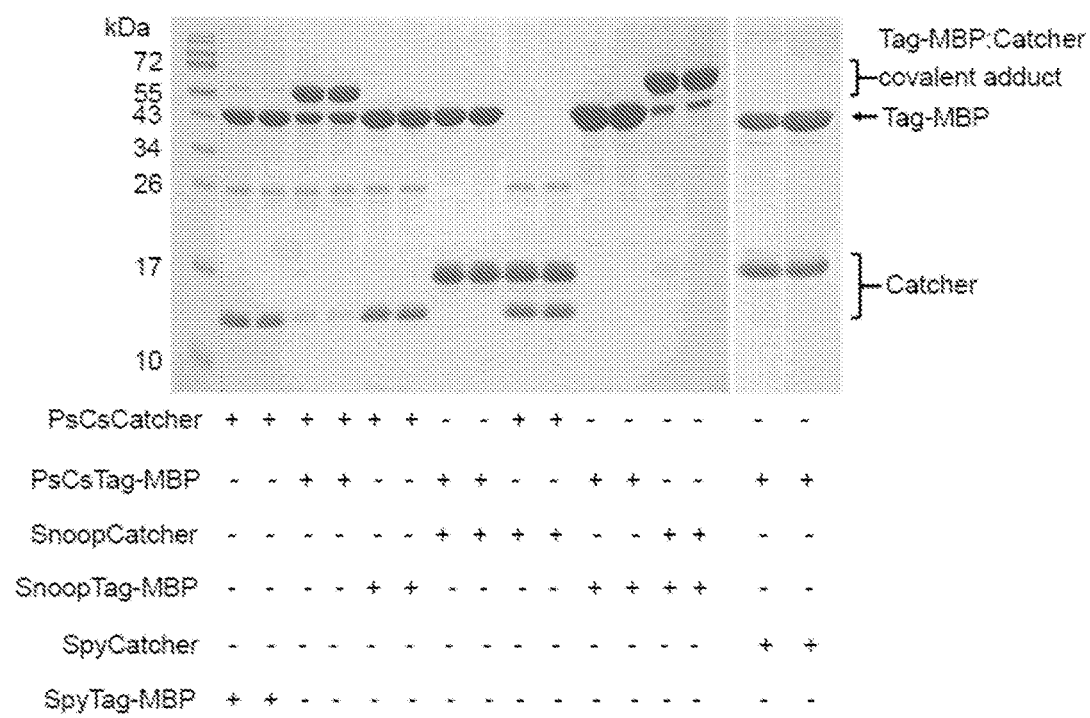
Figure 8:
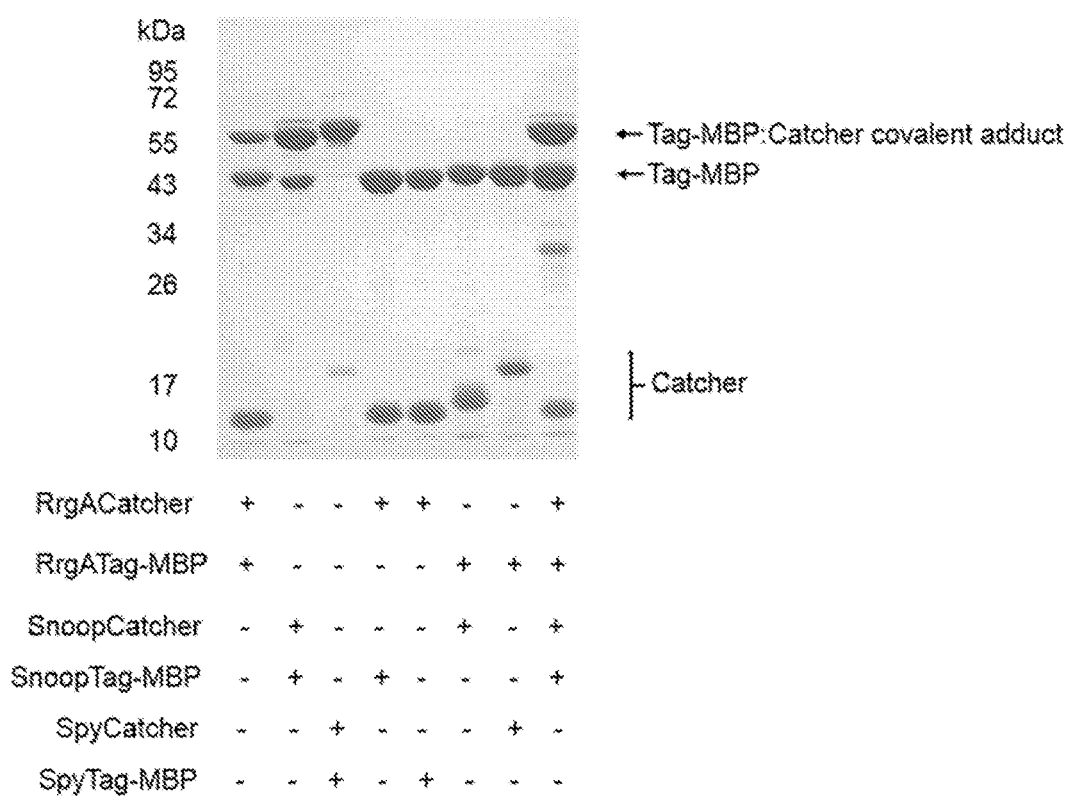

FIG. 8 shows (A) a picture of an SDS-PAGE gel with Coomassie staining characterising PsCsTag/PsCsCatcher, SnoopTag/SnoopCatcher and SpyTag/SpyCatcher orthogonal reactivity; and (B) a picture of an SDS-PAGE gel with Coomassie staining characterising RrgATag/RrgACatcher, SnoopTag/SnoopCatcher and SpyTag/SpyCatcher orthogonal reactivity.

Figure 9:
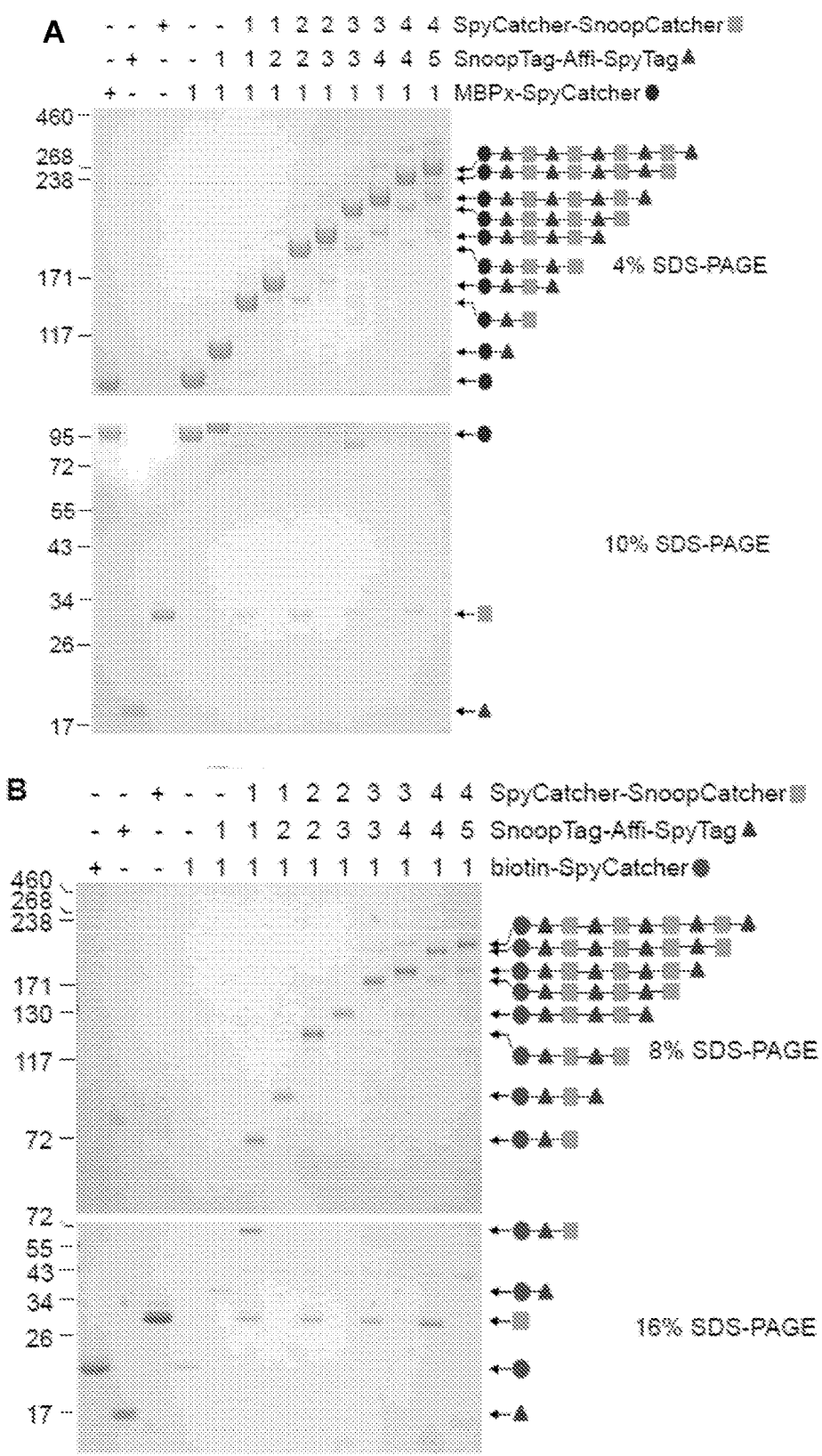

FIG. 9 shows (A) a picture of an SDS-PAGE gel with Coomassie staining analysing solid-phase fusion protein synthesis. Lanes 1-3 show MBPx-SpyCatcher, SnoopTag-Affi-SpyTag and SpyCatcher-SnoopCatcher in isolation. MBPx-SpyCatcher was bound to the amylose resin and stepwise reaction with SnoopTag-Affibody-SpyTag and SpyCatcher-SnoopCatcher was carried out. After each stage, one aliquot of sample was eluted from the resin with maltose (lanes 4-13). Samples were analysed without any further purification; and (B) a picture of an SDS-PAGE gel with Coomassie staining analysing solid-phase fusion protein synthesis. Lanes 1-3 show biotin-SpyCatcher, SnoopTag-Affi-SpyTag and SpyCatcher-SnoopCatcher in isolation. Biotin-SpyCatcher was bound to the streptavidin agarose and stepwise reaction with SnoopTag-Affibody-SpyTag and SpyCatcher-SnoopCatcher was carried out After each stage, one aliquot of sample was eluted from the agarose with biotin (lanes 4-13). Samples were analysed without any further purification.

Figure 10:
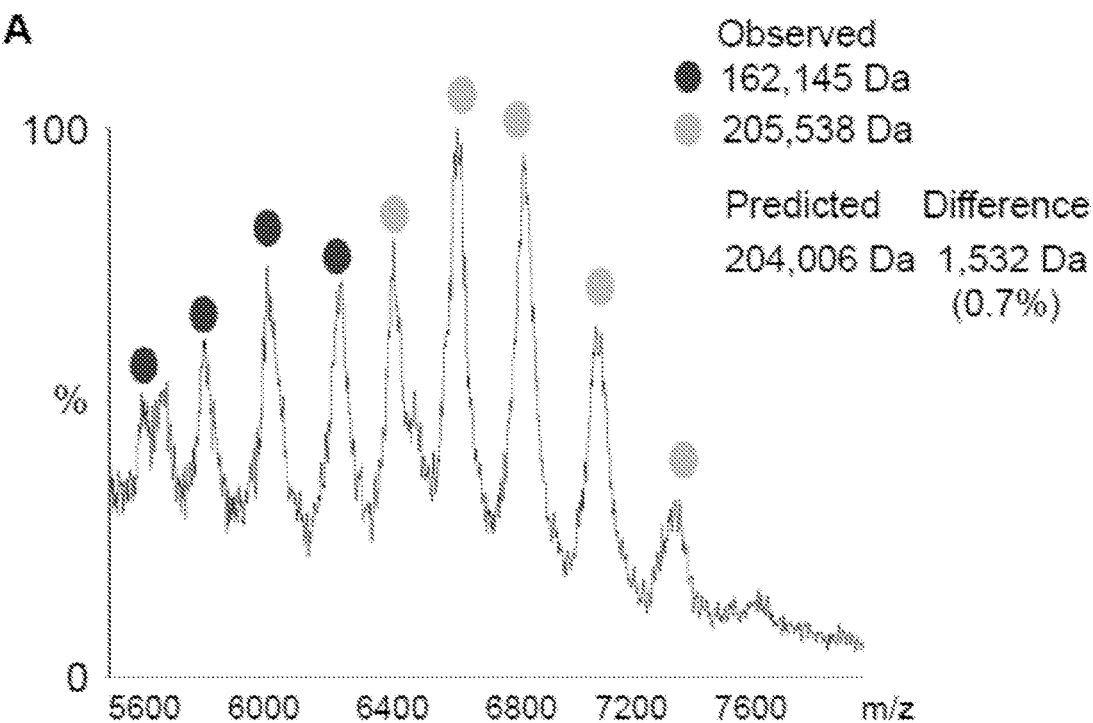
Figure 10:
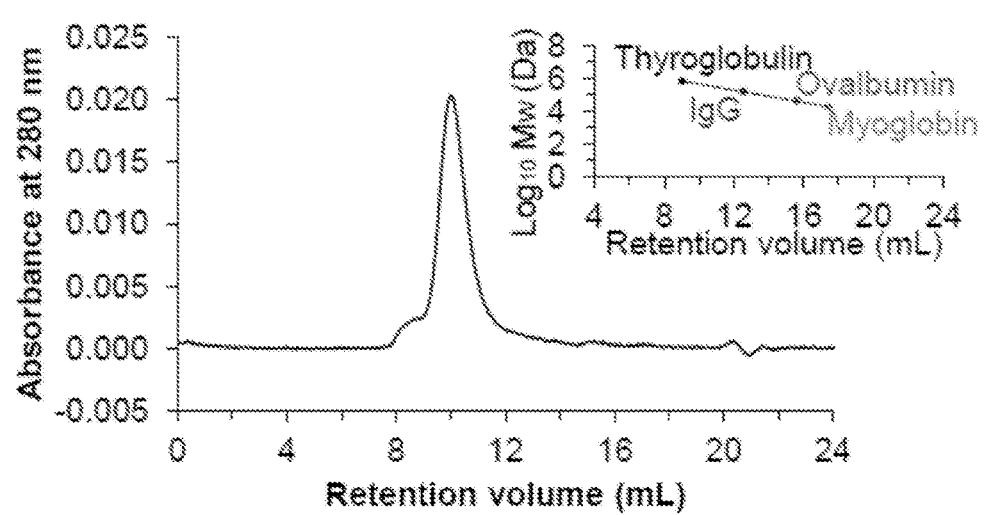

FIG. 10 shows (A) a graph depicting electrospray ionization mass spectrometry to test identity of the decamer fusion protein, biotin-SpyCatcher:(SnoopTag-Affi-SpyTag:SpyCatcher-SnoopCatcher)$_4$:SnoopTag-Affi-SpyTag and (B) a graph depicting size-exclusion chromatography analysis of the decamer fusion protein, MBPx-SpyCatcher(SnoopTag-Affi-SpyTag:SpyCatcher-SnoopCatcher)$_4$:SnoopTag-Affi-SpyTag. The inset shows the molecular weight standards.

Figure 11:
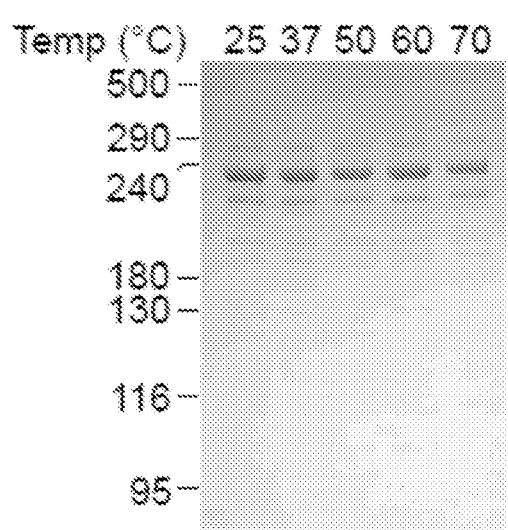
Figure 11:
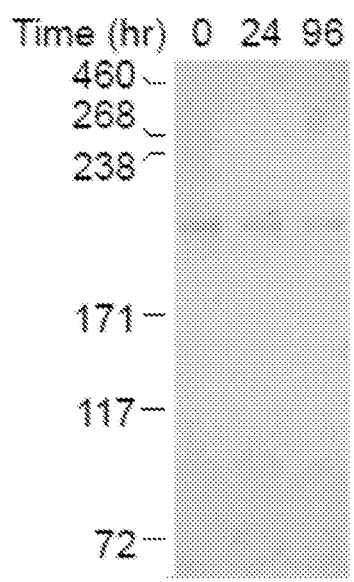

FIG. 11 shows (A) a picture of an SDS-PAGE gel with Coomassie staining analysing the thermostability of the decamer fusion protein, MBPx-SpyCatcher. (SnoopTag-Affi-SpyTag:SpyCatcher-SnoopCatcher)$_4$:SnoopTag-Affi-SpyTag; and (B) a picture of an SDS-PAGE gel with Coomassie staining analysing the time-dependent stability of the decamer fusion protein, biotin-SpyCatcher:(SnoopTag-Affi-SpyTag:SpyCatcher-SnoopCatcher)$_4$:SnoopTag-Affi-SpyTag.

Figure 12:
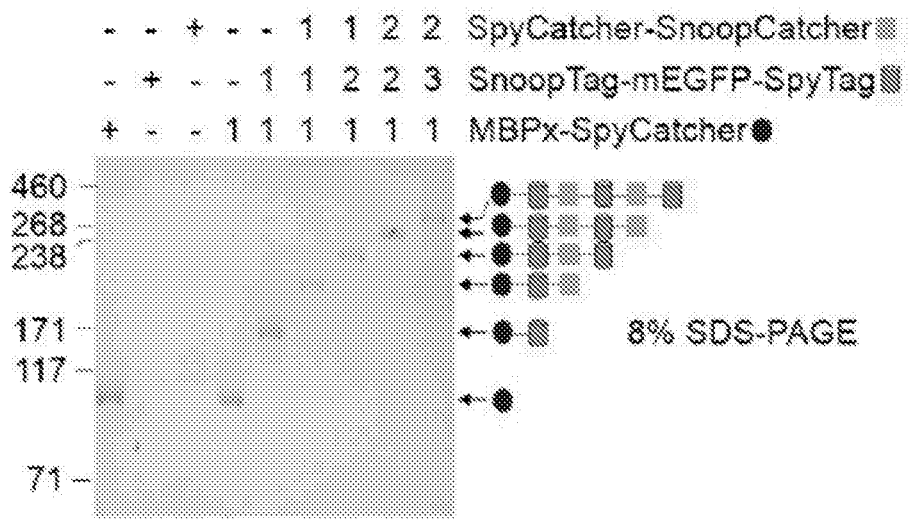
Figure 12:
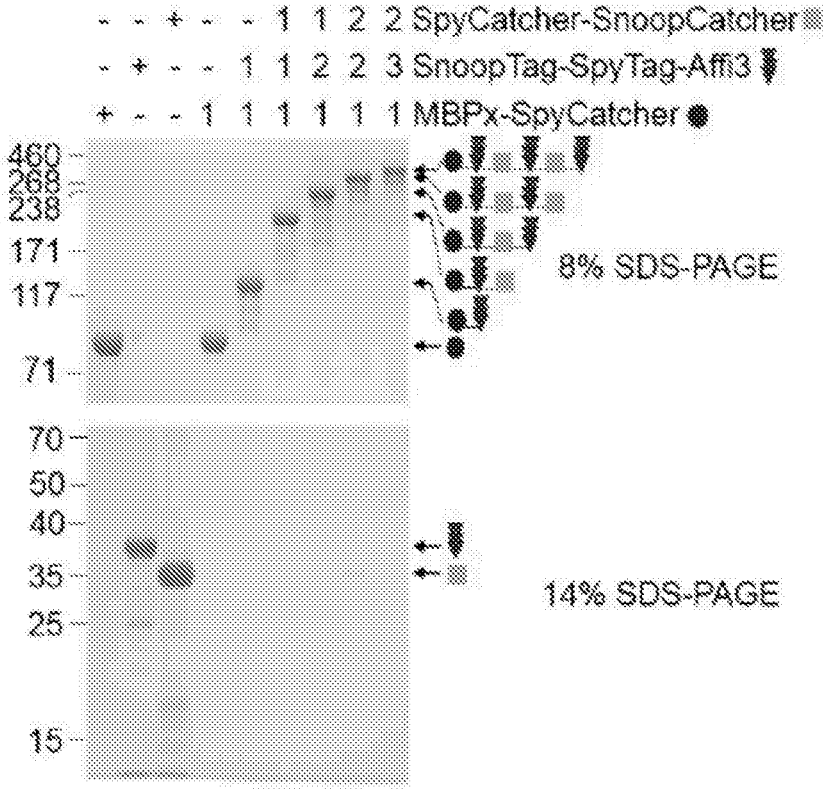

FIG. 12 shows (A) a picture of an SDS-PAGE gel with Coomassie staining analysing solid-phase fusion protein synthesis. Lanes 1-3 show MBPx-SpyCatcher, SnoopTag-mEGFP-SpyTag and SpyCatcher-SnoopCatcher in isolation. MBPx-SpyCatcher was bound to the amylose resin and stepwise reaction with SnoopTag-mEGFP-SpyTag and SpyCatcher-SnoopCatcher was carried out. After each stage, one aliquot of sample was eluted from the resin with maltose (lanes 4-9). Samples were analysed without any further purification; and (B) a picture of an SDS-PAGE gel with Coomassie staining analysing solid-phase fusion protein synthesis. Lanes 1-3 show MBPx-SpyCatcher, SnoopTag-SpyTag-Affi3 and SpyCatcher-SnoopCatcher in isolation. The stepwise reaction was carried out and analysed as in (A).

Figure 13:
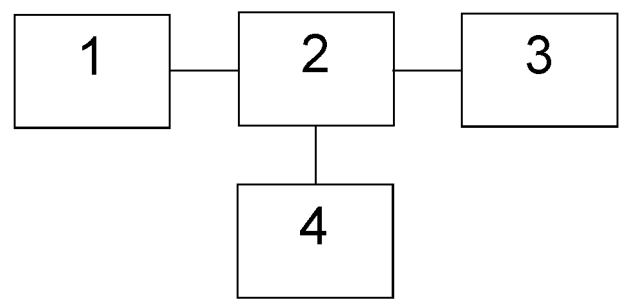
Figure 13:
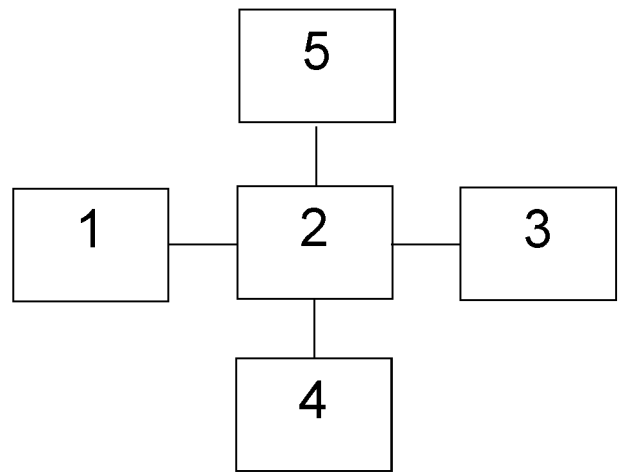

FIG. 13 shows a cartoon of two simple branched fusion protein structures that can be obtained using the methods of the invention.

Figure 14:
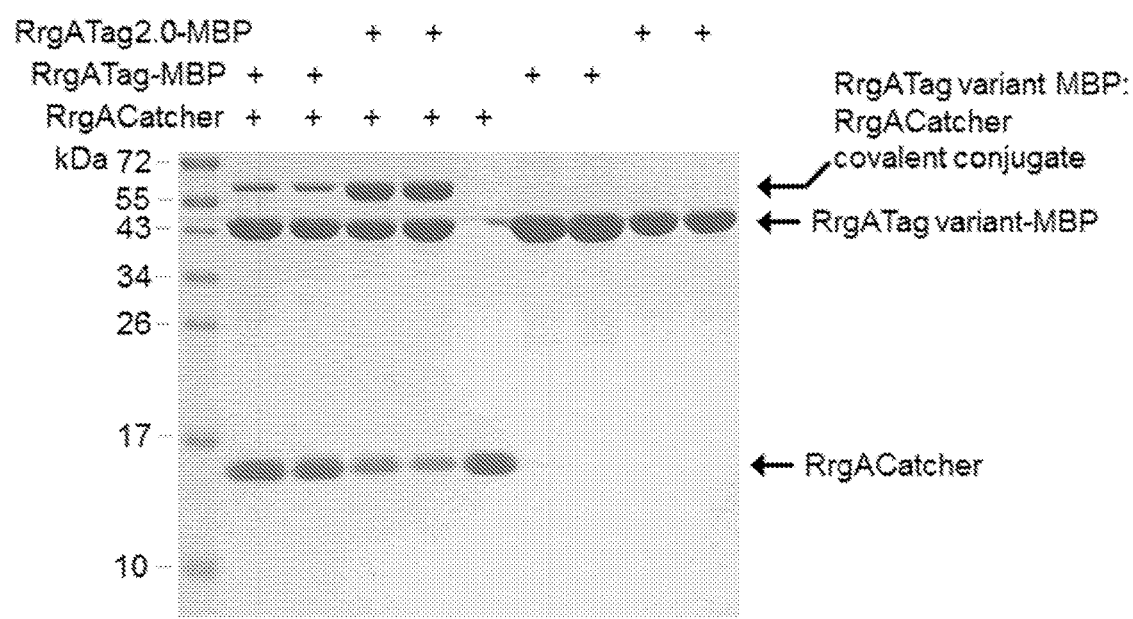

FIG. 14 shows a picture of an SDS-PAGE gel with Coomassie staining comparing the activity of a mutated RrgATag (RrgATag2.0, SEQ ID NO: 111) fused to MBP reacted with RrgACatcher with the unmutated RrgATag (SEQ ID NO: 9) fused to MBP reacted with RrgACatcher.

Figure 15:
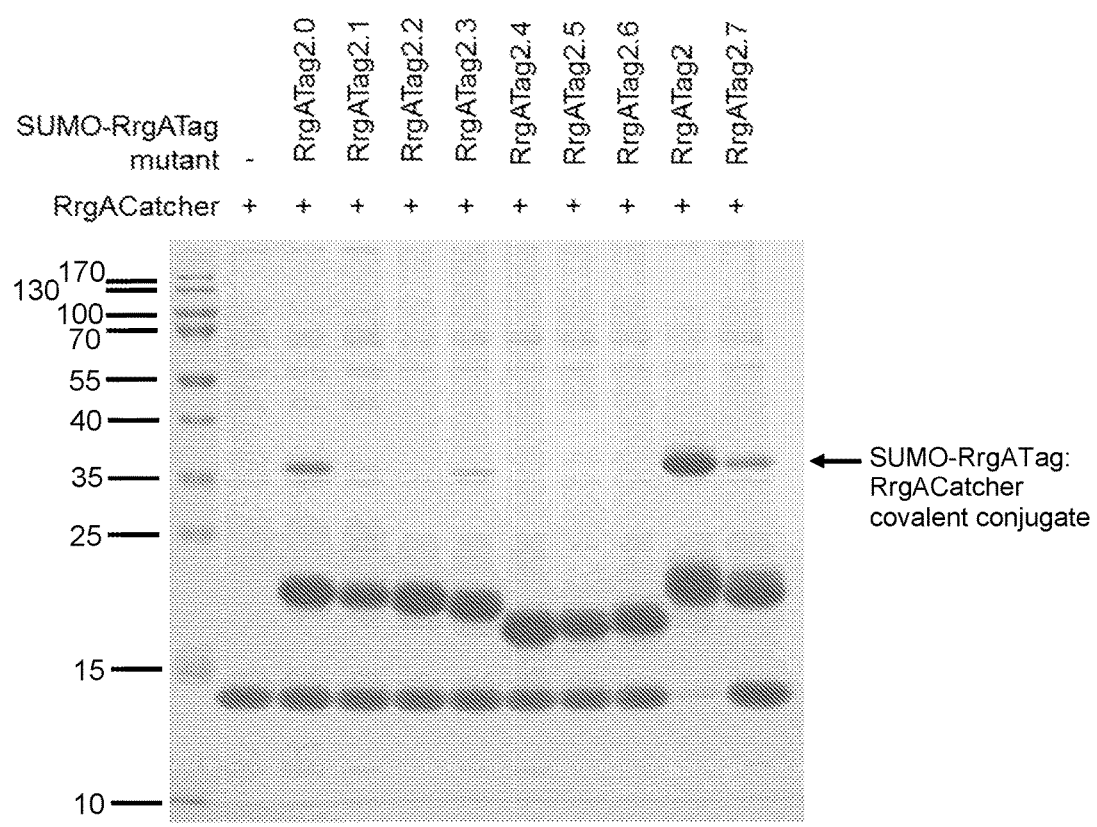

FIG. 15 shows a picture of an SDS-PAGE gel with Coomassie staining characterising various RrgATag peptide linker mutants (fused to SUMO) reacted with RrgACatcher.

Figure 16:
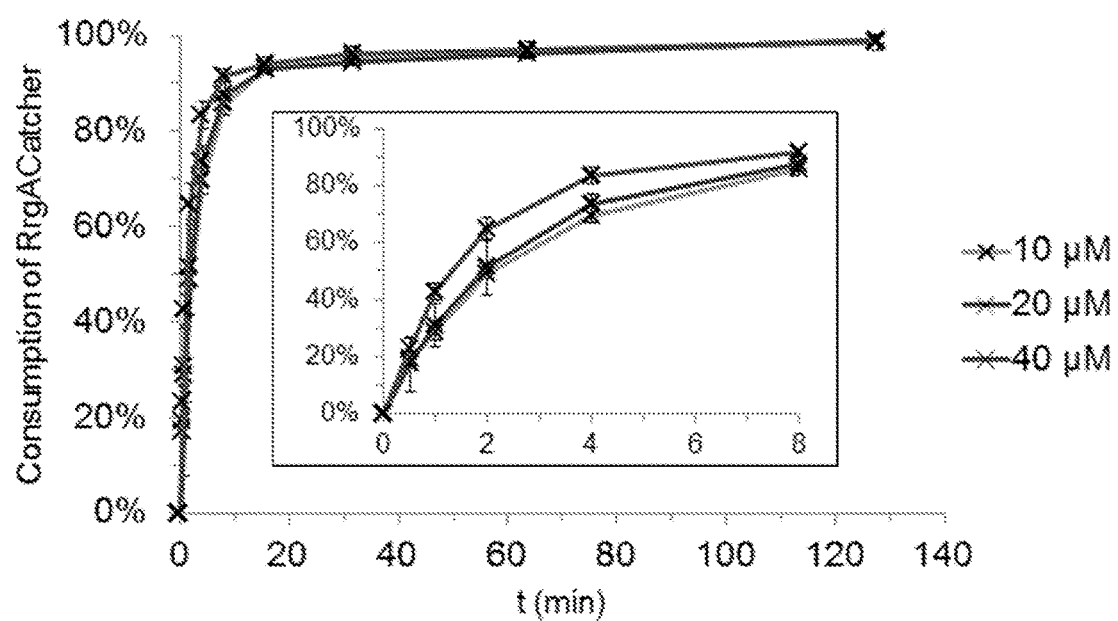

FIG. 16 shows graphs depicting the time-course of RrgATag2 reaction with 1:1, 2:1 or 4:1 ratio of RrgATag2 to RrgACatcher. The inset graph shows the reaction over the first 8 minutes of the reaction.

Figure 17:
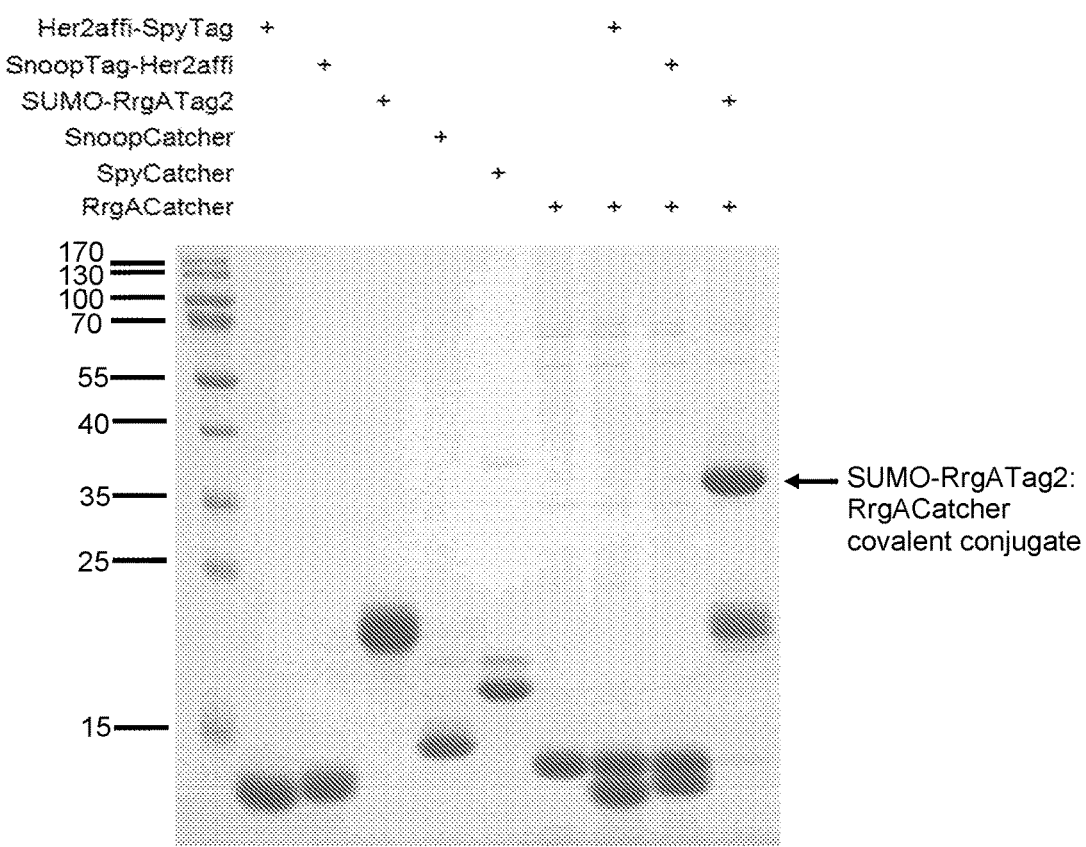

FIG. 17 shows a picture of an SDS-PAGE gel with Coomassie staining characterising RrgACatcher reactivity with SnoopTag, SnoopCatcher, SpyTag, SpyCatcher and RrgATag2.

Figure 18:
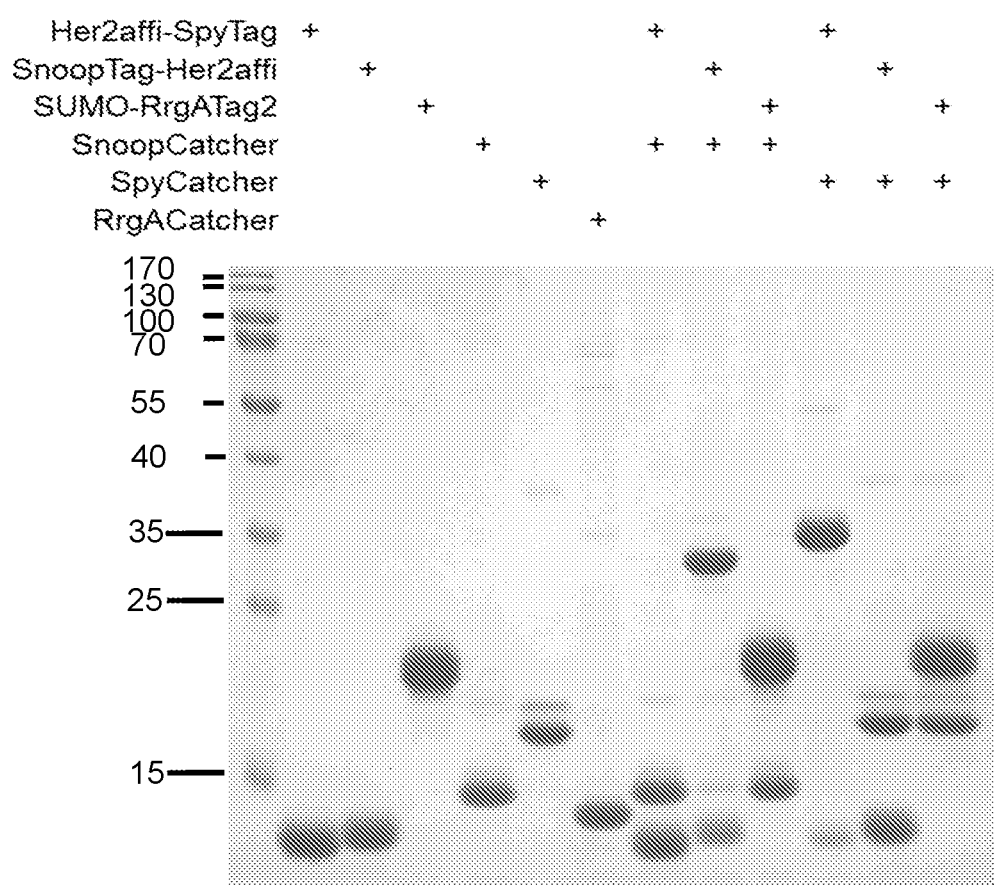

FIG. 18 shows a picture of an SDS-PAGE gel with Coomassie staining characterising RrgATag2/RrgACatcher, SnoopTag/SnoopCatcher and SpyTag/SpyCatcher orthogonal reactivity.

DETAILED DESCRIPTION OF THE INVENTION

Figure 1:
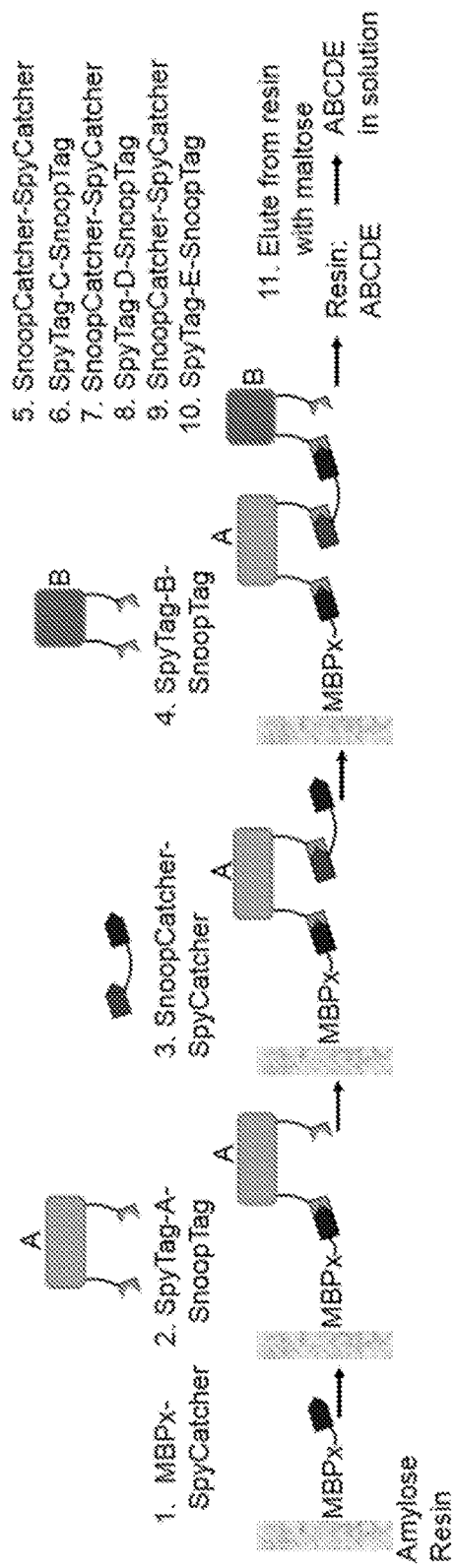
FIG. 1 shows a schematic of a representative example of solid phase synthesis of a fusion protein using two orthogonal pairs of peptide linkers, SnoopTag/Snoop Catcher and SpyTag/SpyCatcher.

A representative example of the method of the invention is set out in FIG. 1, which shows a solid-phase embodiment of the invention. However, this is in no way intended to be limiting on the scope of the invention and various other permutations would be apparent to the skilled person from the description below and are intended to be encompassed by the present invention as defined in the appended claims.

FIG. 1 shows two pairs of peptide linkers, termed SpyTag/SpyCatcher and SnoopTag/Snoop Catcher, wherein each pair, i.e. each "Tag" and "Catcher", react specifically and spontaneously to form an isopeptide bond thereby linking the "Tag" peptide to the "Catcher" peptide. In this respect, the pairs are orthogonal, meaning that they are mutually unreactive, i.e. SpyTag and SpyCatcher cannot react with either of SnoopCatcher or SnoopTag to form an isopeptide bond. As discussed below in more detail, in some embodiments, the "Tags" may be viewed as peptide tags and "Catcher" peptides may be viewed as binding partner proteins.

Thus, in step 1, a first protein, MBPx (a modified version of the maltose-binding protein, discussed below) is provided, wherein the protein has been modified to incorporate a peptide linker, SpyCatcher (i.e. the first part of a first pair of peptides linkers), e.g. via recombinant expression of a nucleic acid molecule encoding the MBPx polypeptide and the SpyCatcher peptide linker in a single open reading frame. In this representative example, the MBPx protein is used as a purification or immobilization tag that allows the extending fusion protein to be immobilized on a solid phase (an amylose resin). However, it will be evident from the discussion below that this is not an essential feature of the invention. For instance, the method may be heterogeneous (i.e. solid phase) or homogeneous (i.e. in solution) and, if heterogeneous, any suitable purification/immobilization tag may be used, i.e. it is not essential that the tag is a protein or peptide tag.

In step 2, the first protein (MBPx-SpyCatcher) is contacted with a second protein (A) which has been modified to incorporate two peptide linkers. One peptide linker is the second part of the first pair of linkers (SpyTag), the first part forming a domain of the first protein (SpyCatcher). The other peptide linker is the first part of a second pair of peptide linkers (SnoopTag); as discussed above, the second pair of linkers does not react with the first pair of linkers. Thus, on contacting the first and second proteins together, the first pair of linkers react (e.g. spontaneously) to form a specific isopeptide bond between the SpyCatcher and SpyTag peptide linkers, thereby linking the first protein (MBPx-SpyCatcher) and second protein (SpyTag-A-SnoopTag) together to form a fusion protein.

In step 3, the fusion protein (MBPx-SpyCatcher-SpyTag-A-SnoopTag) is contacted with a further protein comprising two peptide linkers, SnoopCatcher and SpyCatcher. Thus, one peptide linker (SnoopCatcher) is the second part of the second pair of peptide linkers and the other peptide linker (SpyCatcher) is from the first pair of peptide linkers. These peptide linkers may be connected via a spacer e.g. a peptide spacer, or a protein which is to be incorporated into the final fusion protein. On contacting the fusion protein (MBPx-SpyCatcher-SpyTag-A-SnoopTag) with the further protein (SnoopCatcher-SpyCatcher), the second pair of linkers react (e.g. spontaneously) to form an isopeptide bond, thereby extending the fusion protein. Alternatively viewed, the addition of the SnoopCatcher-SpyCatcher protein may be viewed as functionalising or activating the fusion protein for further extension, i.e. by adding a reactive group (a reactive peptide linker) to the fusion protein.

In step 4, the extended fusion protein from step 3 (MBPx-SpyCatcher-SpyTag-A-SnoopTag-SnoopCatcher-SpyCatcher) is contacted with a further protein (B), which incorporates two peptide linkers akin to the A protein (SpyTag-B-SnoopTag). Again, an isopeptide bond is formed between the peptide linkers that are capable of reacting together, i.e. the first pair, SpyCatcher and SpyTag, to further extend the fusion protein.

It will be evident that this process may be repeated until all of the protein units of the desired fusion protein have been linked together. The fusion protein may be simply eluted from the solid phase, e.g. with maltose, and used without further purification. It should be noted that the terminal protein of the fusion protein needs to be modified to incorporate only a single peptide linker, which can react with a free peptide linker in a protein, e.g. the penultimate protein unit, of the fusion protein. As discussed in the Examples, the inventor has demonstrated synthesis of a fusion protein containing 10 protein units, which has been validated by gel electrophoresis and mass spectrometry.

Whilst not wishing to be bound by theory, it is thought that the precise orientation of the amino acid residues in the peptide linker pairs, e.g. SnoopTag/SnoopCatcher, SpyTag/SpyCatcher etc., promotes nucleophilic attack and formation of an irreversible isopeptide bond between the peptide linkers. As mentioned above, Lysine reacts with either Aspartate or Asparagine in each of these pairs. The SpyTag peptide has a reactive Aspartate and so it cannot react with the reactive Asparagine of SnoopCatcher. The SnoopTag peptide has a reactive Lysine and so it cannot react with the reactive Lysine of SpyCatcher. Therefore these two peptide linker pairs are orthogonal and it will be evident that any orthogonal pairs of peptide linkers could be used in the method of the invention to generate fusion proteins. In this respect, it is the orthogonal, mutually unreactive, properties of the peptide linker pairs that enables the generation of robust and programmable fusion proteins. In particular, if the growing fusion protein chain is attached to a solid-phase, the reacting module (i.e. the next protein to be linked to the fusion protein) can be added in large excess, thereby driving reaction to completion. This means that unreacted building blocks simply may be washed away, so separation (i.e. separation of the growing fusion protein from unreacted components) is unnecessary at each step. Thus, elongating one step at a time allows chain growth using a small number of orthogonal connections. Hence, the method developed by the present inventor is superior to previously described protein-coupling methods, particularly in terms of the stability of the fusion protein product and the simplicity of the individual reaction steps.

Thus, at its broadest, the invention may be viewed as the use of at least two orthogonal pairs of peptide linkers for the production of a fusion protein, wherein each pair of peptide linkers reacts to form an isopeptide bond.

In particular, the peptide linkers of each peptide linker pair react with each other to form an isopeptide bond. As mentioned above, each peptide linker forms a part (e.g. domain) of a protein that will form a unit (e.g. domain or module) of the fusion protein. In other words, the proteins to be linked together may be modified to incorporate at least one peptide linker (e.g. two, three, four peptide linkers etc.), wherein each pair of peptide linkers used in the production of a fusion protein is orthogonal to at least one other pair of peptide linkers used in the production of said fusion protein.

Thus, in some embodiments, the orthogonal pairs of peptide linkers are used in the production of a fusion protein containing at least two protein units (e.g. domains or modules). For instance, in the representative embodiment shown in FIG. 1, the protein used to conjugate protein A with protein B may be viewed as a linker unit, i.e. the linker unit (linker protein) functions only to conjugate protein A with protein B. Thus, the fusion protein may be viewed as containing or comprising at least two functional proteins, i.e. proteins with functions other than as a linker. In other embodiments, the fusion protein may be viewed as containing or comprising at least three proteins (i.e. irrespective of their function).

In further embodiments, the fusion protein may be viewed as containing or comprising at least three functional proteins. For instance, with reference to the representative embodiment shown in FIG. 1, if the linker protein used to conjugate protein A with protein B contains a protein (e.g. a functional protein) in addition to the peptide linkers, it may be viewed as a protein unit (domain or module) of the fusion protein. Thus, the fusion protein may be viewed as containing or comprising at least three functional proteins, i.e. proteins with functions other than, or in addition to, a linker.

Alternatively viewed, the invention provides a method of producing (e.g. generating, synthesizing, assembling etc.) a fusion protein, said method comprising:

a) contacting a first protein with a second protein under conditions that enable the formation of an isopeptide bond between said proteins, wherein said first protein and said second protein each comprise a peptide linker, wherein said peptide linkers are a pair of peptide linkers which react (with each other) to form an isopeptide bond that links said first protein to said second protein to form a linked protein; and b) contacting the linked protein from (a) with a third protein under conditions that enable the formation of an isopeptide bond between said third protein and said linked protein, wherein said third protein comprises a peptide linker which reacts with a further peptide linker in the linked protein from (a), and wherein said peptide linkers are a pair of peptide linkers that react (with each other) to form an isopeptide bond that links said third protein to said linked protein to form a fusion protein, wherein said pair of peptide linkers from/used in (a) are orthogonal to the pair of peptide linkers from/used in (b).

Viewed from yet another aspect, the invention provides a method of producing (e.g. generating, synthesizing, assembling etc.) a fusion protein, said method comprising:

a) providing a first protein comprising a first peptide linker;

b) contacting said first protein with a second protein, wherein said second protein comprises a second peptide linker and a third peptide linker, under conditions that enable said first peptide linker and said second peptide linker to form an isopeptide bond, thereby linking said first and second proteins; and c) contacting said linked first and second proteins with a third protein, wherein said third protein comprises a fourth peptide linker, under conditions that enable said third peptide linker and said fourth peptide linker to form an isopeptide bond, thereby linking said second and third proteins to produce a fusion protein, wherein said first and second peptide linkers are a pair of peptide linkers that are orthogonal to the pair of peptide linkers consisting of said third and fourth peptide linkers.

As noted above, in some embodiments, the second protein may function as a linker between the first and third proteins. Accordingly, the fusion protein may be view as comprising two "functional" proteins, i.e. proteins that have functions other than to link two protein units (modules, domains etc.) together. Thus, in some embodiments, the second protein may be viewed as a linker protein, i.e. a protein containing at least two peptide linkers each from different orthogonal pairs of peptide linkers and optionally a spacer domain, e.g. a peptide spacer.

Thus, in some embodiments, the second protein may be viewed as a linker protein that functionalises or activates the first protein to enable said first protein to be linked with (conjugated to) said third protein. Similarly, where further proteins are added to the fusion protein (i.e. where the fusion protein is extended) a linker protein may be used to functionalise or activate one or more proteins in the fusion protein to enable said one or more proteins to be linked with said further proteins.

As discussed above, the use of orthogonal pairs of peptide linkers facilitates the production of fusion proteins containing a large number of protein units. Accordingly, additional proteins may be added to the fusion protein (i.e. the fusion protein may be extended (e.g. elongated, lengthened)) by contacting the fusion protein with further protein that comprises at least one peptide linker that is capable of forming an isopeptide bond with a peptide linker in a protein of the fusion protein. In this respect, the peptide linker in the new protein forms part of a pair of peptide linkers that is orthogonal to the pair of peptide linkers used to form the previous isopeptide bond in the fusion protein.

Thus, in some embodiments, the method further comprises a step of extending the fusion protein, wherein the new protein (i.e. additional or further protein) to be linked to the fusion protein comprises a peptide linker that forms part of a pair of peptide linkers that is orthogonal to the pair of peptide linkers used to form the previous isopeptide bond in the fusion protein, wherein the peptide linker in the new protein is capable of forming an isopeptide bond with a peptide linker in a protein of the fusion protein, said method comprising contacting said new protein with said fusion protein under conditions that enable said new protein (particularly the peptide linker in said new protein) to form an isopeptide bond with a peptide linker in the fusion protein.

Thus, in some embodiments, the third protein may be viewed as a "further" protein, e.g. an additional or new protein, to be added to the fusion protein. Hence, extending the fusion protein may be viewed as repeating step (c) in the method above, wherein the peptide linkers in the further protein are a pair of peptide linkers that are orthogonal to the pair of peptide linkers used to join the previous protein added to the fusion protein.

In some embodiments, the new protein (i.e. further or additional protein) to be added to the fusion protein comprises at least a second peptide linker (e.g. to allow further extension of the fusion protein chain). Accordingly, the second peptide linker (and any further peptide linkers in the new protein) is orthogonal to the pair of peptide linkers used to link (conjugate) the fusion protein and the new protein.

Thus, in still further embodiments, the method of producing said fusion protein may comprise a step of extending said fusion protein, wherein said third protein comprises a fifth peptide linker and said method comprises a step of contacting said fusion protein with a fourth protein, wherein said fourth protein comprises a sixth peptide linker, under conditions that enable said fifth peptide linker and said sixth peptide linker to form an isopeptide bond, thereby linking said third and fourth proteins to extend said fusion protein, wherein said fifth and sixth peptide linkers form a pair of peptide linkers that is orthogonal to the pair of peptide linkers consisting of said third and fourth peptide linkers.

As shown in the FIG. 1, it is possible to generate a fusion protein comprising multiple protein units (e.g. more than 3 protein units, e.g. 4, 5, 6, 7, 8, 9, 10 or more protein units, such as 12, 15, 20 or more protein units) using two orthogonal pairs of peptide linkers. Thus, in some embodiments the pair of peptide linkers consisting of the fifth and sixth peptide linkers is identical to the pair of peptide linkers consisting of the first and second peptide linkers.

Thus, in still a further embodiment, the fusion protein may be further extended, wherein said fourth protein comprises a seventh peptide linker and said method comprises a step of contacting said fusion protein with a fifth protein, wherein said fifth protein comprises an eighth peptide linker, under conditions that enable said seventh peptide linker and said eighth peptide linker to form an isopeptide bond, thereby linking said fourth and fifth proteins to extend said fusion protein, wherein said seventh and eighth peptide linkers form a pair of peptide linkers that is orthogonal to the pair of peptide linkers consisting of said fifth and sixth peptide linkers.

In some embodiments the pair of peptide linkers consisting of the seventh and eighth peptide linkers is identical to the pair of peptide linkers consisting of the third and fourth peptide linkers.

It will be evident that the fusion protein chain may be extended by repeating the steps described above, e.g. wherein the fifth protein comprises a ninth peptide linker and a sixth protein that comprises a tenth peptide linker and wherein said ninth and tenth peptide linkers form a pair of peptide linkers that is orthogonal to the pair of peptide linkers consisting of said seventh and eighth peptide linkers. In some embodiments, the pair of peptide linkers consisting of the ninth and tenth peptide linkers is identical to the pair of peptide linkers consisting of the first and third peptide linkers and/or said fifth and sixth peptide linkers.

Thus, in some embodiments, the at least two orthogonal pairs of peptide linkers may be used alternately to link (conjugate) proteins to form a fusion protein. Alternatively viewed, the new or further protein to be added to the fusion protein comprises at least one peptide linker that forms part of a pair of peptide linkers that is orthogonal to the pair of peptide linkers used to link the previously added protein in the fusion protein.

Whilst the invention may be worked successfully using two orthogonal pairs of peptide linkers, it will be evident that more than two orthogonal pairs of peptide linkers may be utilized in the methods and uses of the invention. Thus, in the context of the representative examples given above, in some embodiments the pair of peptide linkers consisting of the fifth and sixth peptide linkers is different, preferably orthogonal, to the pair of peptide linkers consisting of the first and second peptide linkers. As discussed below, the use of more than two pairs of orthogonal peptide linkers would enable the production of complex fusion protein structures, e.g. branched structures. Accordingly, as discussed in detail below, the inventor has developed several orthogonal pairs of peptide linkers, which form a further embodiment of the invention.

For instance, a fusion protein comprising three proteins, 1, 2 and 3 may be produced according to the method described above, wherein protein 1 comprises peptide linker A, protein 2 comprises peptide linkers A' and B and protein 3 comprises peptide linker B'. In this respect, peptide linkers A and A' (a pair of peptide linkers) react to form an isopeptide bond and peptide linkers B and B' (a pair of peptide linkers) react to form an isopeptide bond, wherein peptide linker pairs A/A' and B/B' are orthogonal (i.e. do not react with the other pair to form an isopeptide bond). Using a third orthogonal pair of peptide linkers would enable the production of a branched structure. For example, protein 2 may comprise a third peptide linker C and a fourth protein, 4, may comprise a peptide linker C', wherein C and C' (a pair of peptide linkers) react to form an isopeptide bond and wherein peptide linkers A/A', B/B' and C/C' are orthogonal. When the fusion protein 1-2-3 is contacted with protein 4 under conditions that enable C and C' to form an isopeptide bond, the resultant fusion protein will be branched, i.e. 1-2(-4)-3 (see FIG. 13, part A). Alternatively, a fusion protein 1-2-4 may be contacted with protein 3 under conditions that enable B and B' to form an isopeptide bond to produce the branched fusion protein, 1-2(-4)-3. The skilled person would understand that complex branching structures may be generated using three pairs of orthogonal peptide linkers and the complexity of the branching structures may be increased further by using additional orthogonal pairs of peptide linkers. In particular, the use of more than two orthogonal pairs of peptide linkers may advantageously be used to generate asymmetric branching structures.

Thus, in some embodiments, the method and uses of the invention utilise more than two orthogonal pairs of peptide linkers, e.g. 3, 4, 5, 6, 7, 8, 9 or 10 or more orthogonal pairs of peptide linkers.

Branching may also be achieved using two orthogonal pairs of peptide linkers. For instance, a branched fusion protein comprising five proteins, 1-5, may be produced by including additional peptide linkers in one of the proteins, e.g. protein 2 may comprise 4 peptide linkers from two orthogonal pairs of peptide linkers. In this representative embodiment, protein 1 comprises peptide linker A, protein 2 comprises peptide linker A' and three peptide linkers B. Proteins 3, 4 and 5 each comprises peptide linker B', wherein peptide linkers A and A' (a pair of peptide linkers) react to form an isopeptide bond and peptide linkers B and B' (a pair of peptide linkers) react to form an isopeptide bond, wherein peptide linker pairs A/A' and B/B' are orthogonal. Thus, contacting the fusion protein 1-2 with proteins 3-5 would result in a branched fusion protein in which proteins 3-5 are all joined to protein 2 independently of each other (see FIG. 13, part B). It will be evident that proteins 3-5 may be the same or different proteins. Moreover, one or more of proteins 3-5 may comprise additional peptide linkers from orthogonal pairs of peptide linkers to facilitate extension (e.g. the separate, independent extension) of each branch of the fusion protein.

Thus, in some embodiments the fusion protein may be branched. In other embodiments, the fusion protein may be linear. In some embodiments, e.g. where more than two orthogonal pairs of peptide linkers are used, the fusion protein may be comprised of asymmetric branches, i.e. the fusion protein may have an asymmetric structure. Thus, in some embodiments, the invention provides a method of producing a branched fusion protein. In some embodiments, the invention provides a method of producing a linear fusion protein.

The term "branched" refers to fusion proteins in which two or more protein units are linked (joined, conjugated) to the same internal protein unit (a non-terminal protein unit) of a fusion protein, independently of each other, i.e. via independently (separately) formed isopeptide bonds. An internal protein unit or a non-terminal protein unit may be defined as a protein that is linked (joined, conjugated) by an isopeptide bond to at least two other protein units in the fusion protein. A terminal protein unit may be defined as a protein that is linked (joined, conjugated) via an isopeptide bond only to one other protein unit in the fusion protein. Thus, in the representative examples discussed above and shown in FIG. 13, protein 2 is an internal protein unit or non-terminal protein unit because it is joined via isopeptide bonds to proteins 1 and 3, wherein the proteins 4 and 5 may be viewed as "branches" of the fusion protein. Proteins 1, 3, 4 and 5 may be viewed as terminal protein units. Thus, a branched fusion protein comprises more than two terminal protein units.

The term "linear" refers to fusion proteins in which all of the internal protein units are linked only to two other protein units in the fusion protein, thereby generating a linear chain of protein units. Thus, a linear fusion protein comprises only two terminal protein units.

In yet other embodiments, the fusion protein may be circular. For instance, taking the fusion protein above, 1-2-3, if protein 1 also contains a peptide linker C and protein 3 also contains a peptide linker C', proteins 1 and 3 may be linked by an isopeptide bond, thereby forming a circular protein. Thus, in some embodiments, a linear protein may be viewed as being circularisable, i.e. capable of forming a circular fusion protein. In this respect, as discussed below, one or more of the peptide linkers may be blocked or protected to prevent or delay its reaction. Thus, using the example above, if peptide linker C and/or C' is blocked, the fusion protein will be a linear fusion protein that is circularisable and may be circularised by unblocking C and/or C' to allow the peptide linkers to react to form an isopeptide bond.

Thus, in some embodiments, the invention provides a method of producing a circular or circularisable fusion protein.

Thus, the term "circular" generally refers to fusion proteins which do not contain any terminal protein units. However, it will be evident that it is possible to produce a "branched circular" fusion protein, which comprises a circular fusion protein in which one or more of the internal protein units is linked by an isopeptide bond to at least three other protein units in the fusion protein.

The term "orthogonal" as used herein refers to molecules that are mutually unreactive, e.g. molecules that are not capable of reacting with each other or react with a reduced efficiency as compared to corresponding molecules that are capable of reacting with each other. In the context of the peptide linkers of the invention, particularly pairs of peptide linkers, the term orthogonal refers to pairs of peptide linkers that are not capable of reacting with other pairs of peptide linkers to form an isopeptide bond or react with a reduced efficiency as compared to corresponding molecules, e.g. endogenous proteins that are capable of spontaneously forming isopeptide bonds or pairs of peptide linkers that are capable of reacting with each other efficiently to form an isopeptide bond. An inability to react may be viewed as 5% or less of the peptide linkers in a sample reacting to form isopeptide bonds, e.g. 4%, 3%, 2% or 1% or less. A reduced efficiency may be viewed as less than 5% efficiency, e.g. less than 4%, 3%, 2% or 1% efficiency, of a pair of orthogonal peptide linkers to react to form an isopeptide bond compared to the ability of each pair of peptide linkers to form an isopeptide bond. Conversely, a pair of peptide linkers that react efficiently to form an isopeptide bond may react with at least 95% efficiency, e.g. at least 96%, 97%, 98%, 99% or 100% efficiency, i.e. at least 95% of the peptide linkers of a pair of peptide linkers in a sample react to form an isopeptide bond under conditions that enable the formation of an isopeptide bond. For example, two pairs of peptide linkers, A/A' and B/B', may be viewed as orthogonal when A and A' cannot react with B and/or B' to form an isopeptide bond or when A and A' react with B and/or B' to form an isopeptide bond with less than 5% efficiency as compared to the isopeptide bond formation between A and A' and/or B and B'.

Alternatively viewed, two peptide linkers that react together efficiently to form an isopeptide bond under conditions that enable or facilitate isopeptide bond formation may be defined as a cognate pair of peptide linkers, wherein the term "cognate" refers to components that function together, i.e. to react together to form an isopeptide bond. Thus, two peptide linkers that react together efficiently to form an isopeptide bond under conditions that enable or facilitate isopeptide bond formation can also be referred to as being a "complementary" pair of peptide linkers. As such, orthogonal pairs of peptide linkers may be viewed as non-cognate pairs or non-complementary pairs. For instance, based on the representative examples described above, the peptide linker pair A/A' may be viewed as a cognate or complementary pair of peptide linkers, whereas A/A' and B/B' are non-cognate or non-complementary pairs insofar as A and A' cannot react efficiently with B and/or B' to form an isopeptide bond under conditions that enable or facilitate isopeptide bond formation.

The peptide linkers for use in the methods and uses of the invention may be derived from a protein capable of spontaneously forming an isopeptide bond. In particular, "a protein capable of spontaneously forming an isopeptide bond" (also referred to herein as "an isopeptide protein") is one which may form an isopeptide bond in the absence of enzymes or other substances and/or without chemical modification, within its protein chain, i.e. intramolecularly. The two reactive residues for forming the isopeptide bond are therefore comprised within a single protein chain. Thus, proteins which only form isopeptide bonds intermolecularly, i.e. with other peptide or protein chains or units are not considered to be isopeptide proteins as used in the present invention. Particularly, the HK97 capsid subunits which have intermolecular isopeptide bonds are excluded.

The term "isopeptide bond" as used herein, refers to an amide bond between a carboxyl or carboxamide group and an amino group at least one of which is not derived from a protein main chain or alternatively viewed is not part of the protein backbone. An isopeptide bond may form within a single protein or may occur between two peptides or a peptide and a protein. Thus, an isopeptide bond may form intramolecularly within a single protein or intermolecularly i.e. between two peptide/protein molecules, e.g. between two peptide linkers. Typically, an isopeptide bond may occur between a lysine residue and an asparagine, aspartic acid, glutamine, or glutamic acid residue or the terminal carboxyl group of the protein or peptide chain or may occur between the alpha-amino terminus of the protein or peptide chain and an asparagine, aspartic acid, glutamine or glutamic acid. Each residue of the pair involved in the isopeptide bond is referred to herein as a reactive residue. In preferred embodiments of the invention, an isopeptide bond may form between a lysine residue and an asparagine residue or between a lysine residue and an aspartic acid residue. Particularly, isopeptide bonds can occur between the side chain amine of lysine and carboxamide group of asparagine or carboxyl group of an aspartate.

Distances between residues involved in an isopeptide bond are measured from particular C atoms within the residue. Thus, when lysine is involved in the isopeptide bond, the distance is measured from the C-epsilon atom of the lysine; when the aspartic acid is involved in the isopeptide bond, the distance is measured from the C-gamma atom of the aspartic acid; when asparagine is involved in the isopeptide bond, the distance is measured from the C-gamma atom of the asparagine and when glutamic acid is involved in the isopeptide bond, the distance is measured from the C-delta atom of glutamic acid. These atoms (from which distances are calculated) of the reactive residues involved in the isopeptide bond are referred to herein as "relevant atoms".

Typically, in order for an isopeptide bond to form, the reactive residues e.g. the reactive lysine and asparagine/aspartate residues (and particularly the relevant atoms thereof; for lysine the C-epsilon atom and for asparagine/aspartate the C-gamma atom) should be positioned in close proximity to one another in space, e.g. in the isopeptide protein from which they are derived. Thus, particularly, the reactive residues e.g. the lysine and asparagine/aspartate (and particularly the relevant atoms thereof) are within 4 Angstrom of each other in the folded protein (from which they are derived) and may be within 3.8, 3.6, 3.4, 3.2, 3.0, 2.8, 2.6, 2.4, 2.2, 2.0, 1.8 or 1.6 Angstrom of each other. Particularly, the reactive residues (and more particularly their relevant atoms) may be within 1.81, 2.63 or 2.60 Angstrom of each other in the isopeptide protein from which they are derived.

Generally isopeptide proteins from which the peptide linkers of the invention may be derived may comprise a glutamic acid or aspartic acid residue in close proximity to the two other reactive amino acid residues e.g. to lysine and asparagine/aspartate, which are involved in the formation of the isopeptide bond. Particularly, the C-delta atom of the glutamic acid or the C-gamma atom of the aspartic acid residue may be within 5.5 Angstrom from a reactive asparagine/aspartate residue, e.g. from the C-gamma atom of a reactive asparagine/aspartate residue, involved in the isopeptide bond, in the folded protein structure. For example, the glutamic acid (e.g. the C-delta atom thereof) may be within 5.4, 5.2, 5.0, 4.8, 4.6, 4.4, 4.2, 4.0, 3.8, 3.6, 3.4, 3.2 or 3.0 Angstrom from the reactive asparagine/aspartate residue e.g. the C-gamma atom thereof in the isopeptide bond. Particularly, the glutamic acid residue, e.g. the C-delta atom, thereof may be 4.99, 3.84 or 3.73 Angstrom from the asparagine/aspartate residue e.g. the C-gamma atom thereof.

Further, the glutamic acid residue, e.g. the C-delta atom thereof, may be within 6.5 Angstrom of a reactive lysine residue, e.g. the C-epsilon atom thereof, involved in the isopeptide bond, for example within 6.3, 6.1, 5.9, 5.7, 5.5, 5.3, 5.1, 4.9, 4.7, 4.5, 4.3 or 4.1 Angstrom. Particularly, the glutamic acid residue, e.g. the C-delta atom thereof, may be 6.07, 4.80 or 4.42 Angstrom from a reactive lysine, e.g. the C-epsilon atom thereof.

The glutamic acid residue (or aspartic acid residue) may help induce the formation of the isopeptide bond as discussed previously.

As discussed above, the peptide linkers for use in the methods and uses of the invention may be obtained by splitting the reactive domains of an isopeptide protein into two or three domains. Thus, each pair of peptide linkers consists of a peptide comprising a lysine residue and a peptide comprising an aspartate or asparagine residue, wherein said residues (i.e. lysine and aspartate or lysine and asparagine) are involved in the formation of an isopeptide bond (i.e. react to form an isopeptide bond), thereby joining (conjugating) said peptide linkers.

In some preferred embodiments, the formation of the isopeptide bond between said peptide linkers is spontaneous. Accordingly, one of the peptide linkers comprises a glutamic acid or aspartic acid residue that facilitates, e.g. induces or catalyzes the formation of the isopeptide bond between the lysine and asparagine or aspartate residues in the peptide linkers. In some embodiments, the glutamic acid or aspartic acid residue fulfils one or more of the proximity criteria set out above.

Thus, in embodiments where the formation of the isopeptide bond between said peptide linkers is spontaneous, one of the peptide linkers may be viewed as a peptide tag and the other peptide linker (i.e. the linker comprising the glutamic acid or aspartic acid residue that facilitates, e.g. induces or catalyzes, the formation of the isopeptide bond) may be viewed as a peptide binding partner, i.e. the binding partner for the peptide tag as defined further below.

The term "spontaneous" as used herein refers to a bond, e.g. an isopeptide or covalent bond which can form in a protein or between peptides or proteins (e.g. between 2 peptides or a peptide and a protein, i.e. the peptide linkers of the invention) without any other agent (e.g. an enzyme catalyst) being present and/or without chemical modification of the protein or peptide, e.g. without native chemical ligation or chemical coupling using 1-ethyl-3-(3-dimethylaminopropyl) carbodiimide (EDC). Thus, native chemical ligation to modify a peptide or protein to have a C-terminal thioester is not carried out.

Thus, a spontaneous isopeptide bond can form when a protein is isolated on its own or a covalent or isopeptide bond can form between two peptides or a peptide and a protein (i.e. peptide linkers of the invention) when in isolation or without chemical modification. A spontaneous isopeptide or covalent bond may therefore form of its own accord in the absence of enzymes or other exogenous substances or without chemical modification. Particularly however, a spontaneous isopeptide or covalent bond may require the presence of a glutamic acid or an aspartic acid residue in the protein or in one of the peptides/proteins (i.e. in one of the peptide linkers) involved in the bond to allow formation of the bond in a proximity-induced manner.

A spontaneous isopeptide or covalent bond may form almost immediately after the production of a protein or after contact between two or more proteins comprising peptide linkers of the invention, e.g. peptide tag and binding partner, e.g. within 1, 2, 3, 4, 5, 10, 15, 20, 25 or 30 minutes, or within 1, 2, 4, 8, 12, 16, 20 or 24 hours. The bond may form under a range of conditions, such as in phosphate-buffered saline (PBS) or Tris-buffered saline (TBS) at pH 4.0-9.0, e.g. 5.0, 5.5, 6.5, 7.0, 7.5, 8.0 or 8.5, and at 0-40° C., e.g. 1, 2, 3, 4, 5, 10, 12, 15, 18, 20, 22 or 25° C. The skilled person would readily be able to determine other suitable conditions.

Thus, in some embodiments, contacting proteins comprising peptide linkers as defined herein "under conditions that enable the formation of an isopeptide bond" includes contacting said proteins in buffered conditions, e.g. in a buffered solution or on a solid phase (e.g. column) that has been equilibrated with a buffer, such as PBS or TBS. The step of contacting may be at any suitable pH, such as pH 4.0-9.0, e.g. 4.5-8.5, 5.0-8.0, 5.5-7.5, such as about pH 6.2, 6.4, 6.6, 6.8, 7.0, 7.2, 7.4, 7.6, 7.8 or 8.0. Additionally or alternatively, the step of contacting may be at any suitable temperature, such as about 0-40° C., e.g. about 1-39, 2-38, 3-37, 4-36, 5-35, 6-34, 7-33, 8-32, 9-31 or 10-30° C., e.g. about 10, 12, 15, 18, 20, 22 or 25° C. The skilled person would understand that the conditions may need to be adapted depending on the characteristics of the peptide linkers used in the method of the invention and would readily be able to determine which conditions are suitable.

In some embodiments, contacting proteins comprising peptide linkers as defined herein "under conditions that enable the formation of an isopeptide bond" includes contacting said proteins in the presence of a chemical chaperone, e.g. a molecule that enhances or improves the reactivity of the peptide linkers. In some embodiments, the chemical chaperone is TMAO (trimethylamine N-oxide). In some embodiments, the chemical chaperone, e.g. TMAO, is present in the reaction at a concentration of at least about 0.2M, e.g. at least 0.3, 0.4, 0.5, 1.0, 1.5, 2.0 or 2.5M, e.g. about 0.2-3.0M, 0.5-2.0M, 1.0-1.5M.

In some embodiments, the formation of the isopeptide bond between said peptide linkers is not spontaneous, i.e. the formation of the isopeptide bond is induced or catalyzed by a component that is added to the reaction. The component that induces or catalyzes the formation of the isopeptide bond may be a peptide, e.g. a polypeptide such as an enzyme, such as a transglutaminase. In a preferred embodiment, the component that induces or catalyzes the formation of the isopeptide bond may be a peptide derived from an isopeptide protein, i.e. a domain or fragment of an isopeptide protein comprising a glutamic acid or aspartic acid residue that facilitates, e.g. induces or catalyzes the formation of the isopeptide bond between the lysine and asparagine or aspartate residues in the peptide linkers. A peptide that facilitates, e.g. induces or catalyzes the formation of the isopeptide bond between the lysine and asparagine or aspartate residues in the peptide linkers may be viewed as a protein ligase or peptide ligase, insofar as it is capable of inducing, specifically, the formation of an isopeptide bond between two peptide linkers.

Thus, in embodiments where the formation of the isopeptide bond between said peptide linkers is not spontaneous, i.e. wherein a component (e.g. peptide, e.g. peptide ligase) that induces the formation of an isopeptide bond between the peptide linkers is provided separately, both of the peptide linkers may be viewed as peptide tags, as defined below. Accordingly, the peptide that induces the formation of an isopeptide bond between the peptide linkers (peptide tags) may be viewed as a peptide ligase or peptide linker pair binding partner.

Thus, in some embodiments, the invention further comprises a step of contacting proteins to be linked with a component (e.g. peptide) capable of inducing the formation of an isopeptide bond between said peptide linkers under conditions that enable the formation of an isopeptide bond between said proteins. In some embodiments, the component capable of inducing the formation of an isopeptide bond between said peptide linkers is a peptide comprising a glutamic acid or aspartic acid residue that induces the formation of the isopeptide bond between the lysine and asparagine or aspartate residues in the peptide linkers in said proteins.

The component (e.g. peptide) capable of inducing the formation of an isopeptide bond between said peptide linkers may be added to the reaction before, after or contemporaneously with when the proteins to be joined together are contacted with each other. In some embodiments, the component (e.g. peptide) capable of inducing the formation of an isopeptide bond between said peptide linkers may be added to the reaction after the proteins to be joined together are contacted with each other.

The use of a component (e.g. peptide) capable of inducing the formation of an isopeptide bond between said peptide linkers is particularly advantageous because it allows the proteins units of the fusion protein to be joined (conjugated) without the presence of large intervening peptide domains. Alternatively viewed, the use of a component (e.g. peptide) capable of inducing the formation of an isopeptide bond between said peptide linkers facilitates the use of small peptide linkers (e.g. peptide tags), i.e. the minimum peptide sequence of each peptide linker in an cognate peptide linker pair capable of forming an isopeptide bond between said peptide linkers.

In some embodiments, the pair of cognate peptide linkers and the peptide capable of inducing the formation of an isopeptide bond between said peptide linkers are derived from the same isopeptide protein.

Proteins capable of spontaneously forming an isopeptide bond may be capable of forming at least one such bond and may comprise more than one isopeptide bond, for example 2, 3, 4, 5, 6, 7, 8, 9, 10 or more. It may be possible to develop several different peptide linker pairs from an isopeptide protein, particularly if more than one spontaneously formed isopeptide bond is present within a protein. In some embodiments, different peptide linker pairs derived from the same isopeptide protein may be orthogonal. It is preferred in the present invention to develop each pair of peptide linkers from an isopeptide protein which comprises a single or only two isopeptide bonds.

Examples of known proteins capable of spontaneously forming one or more isopeptide bonds include Spy0128 (Kang et al, Science, 2007, 318(5856), 1625-8), Spy0125 (Pointon et al, J. Biol. Chem., 2010, 285(44), 33858-66) and FbaB (Oke et al, J. Struct Funct Genomics, 2010, 11(2), 167-80) from *Streptococcus pyogenes*, Cna of *Staphylococcus aureus* (Kang et al, Science, 2007, 318 (5856), 1625-8), the ACE19 protein of *Enterococcus faecalis* (Kang et al, Science, 2007, 318(5856), 1625-8), the BcpA pilin from *Bacillus cereus* (Budzik et al, PNAS USA, 2007, 106(47), 19992-7), the minor pilin GBS52 from *Streptococcus agalactiae* (Kang et al, Science, 2007, 318(5856), 1625-8), SpaA from *Corynebacterium diphtheriae* (Kang et al, PNAS USA, 2009, 106(40), 16967-71), SpaP from *Streptococcus mutans* (Nylander et al, Acta Crystallogr Sect F Struct Biol Cryst Commum., 2011, 67(Pt1), 23-6), RrgA (Izore et al, Structure, 2010, 18(1), 106-15), RrgB (El Mortaji et al, J. Biol. Chem., 2010, 285(16), 12405-15) and RrgC (El Mortaji et al, J. Biol. Chem., 2010, 285(16), 12405-15) from *Streptococcus pneumoniae*, SspB from *Streptococcus gordonii* (Forsgren et al, J Mol Biol, 2010, 397(3), 740-51). As discussed above, any of these proteins may be used to generate peptide linkers (particularly cognate peptide linker pairs) for use in the methods and uses of the present invention.

The arrangement or order of the peptide linkers in the proteins to be linked to form the fusion protein is not particularly important. For instance, the first protein of the desired fusion protein may comprise a peptide tag (A) and the second protein may comprise a peptide binding partner that is cognate for the peptide tag on the first protein (A') and a peptide binding partner that is cognate for the peptide tag on the third protein (B'). Alternatively, the first protein of the desired fusion protein may comprise a peptide binding partner (A') and the second protein may comprise a peptide tag that is cognate for the peptide binding partner on the first protein (A) and a peptide tag that is cognate for the peptide binding partner on the third protein (B). In this respect, it is sufficient that the pair of peptide linkers used to link two proteins (e.g. a first protein and second protein, a fusion protein with a further protein etc.) is orthogonal to the pair of peptide linkers used to extend the fusion protein. As discussed below, orthogonal peptide linkers may be achieved in a variety of ways.

Thus, in some preferred embodiments, the first pair of peptide linkers (A/A') comprises one peptide linker, A, (e.g. peptide tag) with a reactive lysine residue and a one peptide linker, A', (e.g. peptide binding partner) with a reactive aspartate or asparagine residue and the second pair of peptide linkers (B/B') comprises one peptide linker, B, (e.g. peptide tag) with a reactive aspartate or asparagine residue and one peptide linker, B', (e.g. peptide binding partner) with a reactive lysine residue. Using the example provided above, there is no suitable route for A to react with B' and no suitable route for B to react with A'. Accordingly, the peptide linker pairs are orthogonal to each other.

In further embodiments, the first pair of peptide linkers (A/A') comprises one peptide linker, A, (e.g. peptide tag) with a reactive lysine residue and a one peptide linker, A', (e.g. peptide binding partner) with a reactive aspartate or asparagine residue and the second pair of peptide linkers (B/B') comprises one peptide linker, B, (e.g. peptide tag) with a reactive lysine residue and a one peptide linker, B', (e.g. peptide binding partner) with a reactive aspartate or asparagine residue. Alternatively, the first pair of peptide linkers (A/A') comprises one peptide linker, A, (e.g. peptide tag) with a reactive aspartate or asparagine residue and a one peptide linker, A', (e.g. peptide binding partner) with a reactive lysine residue and the second pair of peptide linkers (B/B') comprises one peptide linker, B, (e.g. peptide tag) with a reactive aspartate or asparagine residue and a one peptide linker, B', (e.g. peptide binding partner) with a reactive lysine residue. In these embodiments, peptide linkers (peptide tags) A and B may be selected such that they have a substantial difference in size in at least one (e.g. two, three) "anchor" residues, so that the non-covalent docking of A and B' and B and A' (i.e. the interaction between A and B' and B and A') is inefficient, thereby ensuring there is minimal cross-reaction.

The term "anchor residues" refers to amino acid residues in a β-strand of a one of the peptide linkers in a cognate peptide linker pair (e.g. peptide binding partner) pointing toward the hydrophobic core of the peptide linker and accepting the reactive residue from the other peptide linker of the cognate peptide linker pair (e.g. peptide tag). A β-strand alternates between residues facing towards the solvent and residues facing towards the hydrophobic protein core and the residue orientation is defined from the structure of the domain forming a spontaneous isopeptide bond in the isopeptide protein from which the peptide linker is derived. This may be determined by any suitable method known in the art, e.g. X-ray crystallography, nuclear magnetic resonance or cryo-electron microscopy.

Small anchor residues include alanine and valine. Intermediate size anchor residues include leucine, isoleucine and methionine. Large anchor residues include phenylalanine and tryptophan. Thus, in some embodiments at least one small anchor residue may be replaced with an intermediate size or large anchor residue. In some embodiments at least one intermediate size anchor residue may be replaced with a small or large anchor residue. In still further embodiments, at least one large anchor residue may be replaced with an intermediate size or small anchor residue.

In some embodiments, orthogonal pairs of peptide linkers may be derived from different isopeptide proteins or different domains of the same isopeptide protein. In some embodiments, orthogonal pairs of peptide linkers are produced de novo.

Pairs of peptide linkers that are produced de novo should possess the two required reactive amino acid residues for the spontaneous formation of the isopeptide bond, preferably together with a glutamic acid or aspartic acid residue. Thus, as described above, one peptide linker comprises a reactive lysine residue and the other peptide linker comprises a reactive asparagine or aspartate residue. In a preferred embodiment, one of the peptide linkers also comprises a glutamic acid or aspartic acid residue that induces or facilitates the formation of an isopeptide bond between said peptide linkers. However, as noted above, a component (e.g. peptide, e.g. a peptide ligase) comprising a glutamic acid or aspartic acid residue that induces or facilitates the formation of an isopeptide bond between said peptide linkers may be provided separately.

It will be evident that neither peptide linker in a cognate peptide linker pair comprises both reactive residues involved in the formation of the isopeptide bond, i.e. each peptide linker in a cognate pair of peptide linkers comprises one reactive residue, i.e. a lysine residue or an aspartate/asparagine residue.

In embodiments where one of the peptide linkers comprises a glutamic acid or aspartic acid residue that induces or facilitates the formation of an isopeptide bond between said peptide linkers, typically said glutamic acid or aspartic acid residue is within 6.5 Angstrom of the residue in the linker involved in the isopeptide bond, e.g. within 6.0, 5.5, 5.0, 4.5, 4.0, 3.5 or 3.0 Angstrom. These distances particularly refer to the distances between the relevant atoms within each residue, i.e. the atoms involved in forming the isopeptide bond. When the two peptide linkers are brought into proximity with each other, e.g. when the first and second proteins are contacted together, the two reactive residues (and more particularly, their relevant atoms) involved in the bond should be within 4 Angstrom from each other in space, preferably 3.8, 3.6, 3.4, 3.2, 3.0, 2.8, 2.6, 2.4, 2.2, 2.0, 1.8 or 1.6 Angstrom.

The skilled person would immediately recognise that the pKa of residues involved in the isopeptide bond formation should also be considered when designing an isopeptide protein de novo. For example, it is preferred that the reactive lysine residue be deprotonated before reaction, which at neutral pH may require the lysine to be buried in the hydrophobic core.

Whilst it is preferred that orthogonal pairs of peptide linkers may be derived from different isopeptide proteins or different domains of the same isopeptide protein, it is possible to produce orthogonal pairs of peptide linkers from the same isopeptide protein, particularly from the same domains of an isopeptide protein. For instance, one peptide linker from a cognate pair of peptide linkers may be modified such that it does not react (or does not react efficiently) with the other peptide linker in the pair. The modification may be reversible, such that reversing or removing the modification that prevents the reaction between the peptide linkers reconstitutes the capacity of the peptide linker pair to react efficiently to form an isopeptide bond. Thus, by way of example, one of the peptide linkers of the cognate peptide linker pair A/A' may be modified, e.g. A is modified by the addition of a blocking group, to produce peptide linker B, wherein B cannot react efficiently with A' or A to form an isopeptide bond. Removal of the blocking group from B results in the peptide linker B', which is capable of reacting with A' to form an isopeptide bond.

The use of reversible or removal blocking groups is well known in the art. Thus, the addition of a blocking group to one peptide linker from a cognate pair of peptide linkers to produce an orthogonal pair of peptide linkers may be viewed as adding a protecting group to the peptide linker or caging the peptide linker. The blocking (e.g. protecting, masking or caging) group may be removed by any suitable means known in the art that reconstitutes the capacity of the peptide linker to react efficiently with the other peptide linker of the peptide linker pair to form an isopeptide bond. The removal of the blocking group (e.g. deprotecting, unmasking, uncaging) may be achieved via a chemical, enzymatic or light reaction, depending on the nature of the blocking group. Suitable examples of blocking groups include bulky moieties, such as proteins which may sterically impede reaction and may be removed by use of an enzyme, such as Tobacco Etch Virus protease (as reviewed in Bioorg Med Chem. 2012 Jan. 15; 20(2):571-82. doi: 10.1016/j.bmc.2011.07.048. Epub 2011 Jul. 30. Cleavable linkers in chemical biology. Leriche G, Chisholm L, Wagner A. trans-cyclooctene-caged lysine, (N-(((E)-cyclooct-2-en-1-yl)-oxy)carbonyl-L-lysine, which is chemically decaged by reaction with a tetrazine (Nat Chem Biol. 2014 December; 10(12):1003-5. doi: 10.1038/nchembio.1656. Epub 2014 Nov. 2. Diels-Alder reaction-triggered bioorthogonal protein decaging in living cells. Li J, Jia S, Chen P R) or lysine caged with o-nitrobenzyl or coumarin groups which are decaged by light of the appropriate wavelength, as well known in the art (see e.g. Chem Rev. 2013 Jan. 9; 113(1):119-91. doi: 10.1021/cr300177k. Epub 2012 Dec. 21. Photoremovable protecting groups in chemistry and biology: reaction mechanisms and efficacy. Klán, Šolomek T, Bochet C G, Blanc A, Givens R, Rublna M, Popik V, Kostikov A, Wirz J.)

The use of blocking groups need not be limited to the production of additional orthogonal pairs of peptide linkers. For instance, blocking groups may be particularly useful to control the extension of fusion proteins, e.g. in multiplex reactions. By way of example, multiple fusion proteins may be synthesised on a single solid phase substrate, e.g. to produce an array comprising a variety of different fusion proteins. The physical separation of each fusion protein on the solid phase would facilitate the selective unblocking of peptide linkers on the substrate, e.g. using light-reactive blocking groups akin to the generation of nucleic acid arrays. The selective unblocking of peptide linkers would enable the extension of a single fusion protein, or sets of fusions proteins (e.g. in a specific location on the solid phase), in one extension reaction and the extension of a different fusion protein, or set of fusion proteins, in subsequent reactions.

Thus, in some embodiments, one or more of the peptide linkers may comprise a blocking group, i.e. a reversible blocking group. In some embodiments, the blocking group may be removed by contacting the fusion protein with light, e.g. UV light, a chemical or an enzyme that removes the blocking group.

Thus, in some embodiments, the method of the invention may comprise a step of unblocking or removing a blocking group from a peptide linker in the fusion protein.

In a representative embodiment, the invention provides a method of producing (e.g. generating, synthesizing, assembling etc.) a fusion protein, said method comprising:

a) contacting a first protein with a second protein under conditions that enable the formation of an isopeptide bond between said proteins, wherein said first protein and said second protein each comprise a peptide linker, wherein said peptide linkers are a pair of peptide linkers which react (with each other) to form an isopeptide bond that links said first protein to said second protein to form a linked protein; and b) contacting the linked protein from (a) with a third protein under conditions that enable the formation of an isopeptide bond between said third protein and said linked protein, wherein said third protein comprises a peptide linker which reacts with a further peptide linker in the linked protein from (a), and wherein said peptide linkers are a pair of peptide linkers that react (with each other) to form an isopeptide bond that links said third protein to said linked protein to form a fusion protein, wherein said pair of peptide linkers from (a) are orthogonal to the pair of peptide linkers from (b)

and wherein the further peptide linker in the linked protein comprises a blocking group and the conditions that enable the formation of an isopeptide bond between said third protein and said linked protein include treating the linked protein to removing the blocking group.

In some embodiments the blocking group may be removed (the peptide linker may be unblocked) before the step of contacting the linked protein with said third protein. In some embodiments, the blocking group may be removed (the peptide linker may be unblocked) after or contemporaneously with the step of contacting the linked protein with said third protein.

The term "peptide linker" as used herein generally refers to a peptide, oligopeptide or polypeptide which may be designed or derived directly from an isopeptide protein, e.g. the peptide linker may be a fragment of an isopeptide protein or a modification thereof. There is no standard definition regarding the size boundaries between what is meant by peptide, oligopeptide and polypeptide, but typically a peptide may be viewed as comprising between 2-20 amino acids, and oligopeptide between 21-39 amino acids and a polypeptide may be viewed as comprising at least 40 amino acids. Thus, a peptide linker as defined herein may be viewed as comprising at least 6 amino acids, e.g. 6-300 amino acids.

In some embodiments, a peptide linker may be referred to as a peptide tag and may be between 6-50 amino acids in length, e.g. 7-45, 8-40, 9-35, 10-30, 11-25 amino acids in length, e.g. it may comprise or consist of 6, 7, 8, 9, 10, 11, 12, 13, 14, 15, 16, 17, 18, 19 or 20 amino acids. The peptide linker or tag specifically binds covalently via an isopeptide bond to a second peptide linker, wherein another peptide linker, which may be viewed as a peptide tag or a peptide binding partner, as defined below. Two peptide linkers (e.g. peptide tag and peptide tag or peptide tag and peptide binding partner) that react with each other (e.g. specifically and efficiently) to form an isopeptide bond may be defined as a pair of peptide linkers, particularly a cognate pair of peptide linkers.

Thus, as mentioned above, a peptide linker must comprise at least one amino acid residue, e.g. lysine or asparagine/aspartate, that is involved in the formation of an isopeptide bond. Accordingly, each peptide linker in a pair of peptide linkers must comprise a different, i.e. complementary, reactive amino acid residue that is involved in the formation of an isopeptide bond, i.e. one peptide linker comprises a lysine residue and the other peptide linker comprises an asparagine or aspartate residue.

In some embodiments, a pair of peptide linkers comprises two peptide tags. Typically, two peptide tags do not react spontaneously to form an isopeptide bond, i.e. they require the addition of a component (e.g. peptide, e.g. a peptide ligase) that induces or catalyzes the formation of the isopeptide bond between said peptide tags/linkers, as defined above.

In some embodiments, a peptide linker (i.e. one of the peptide linkers in a cognate pair of peptide linkers) may be referred to as a peptide binding partner, which may be defined as a peptide (particularly an oligopeptide or polypeptide) which is derived or designed from an isopeptide protein and which may covalently bind to a peptide tag via an isopeptide bond (preferably via a spontaneous reaction). In some embodiments, the peptide binding partner may be designed or derived from the same isopeptide protein as the peptide tag to which it binds covalently, i.e. its corresponding peptide tag or linker.

Generally, a peptide binding partner is larger than its corresponding peptide tag and comprises or consists of a larger fragment or portion of the isopeptide protein compared to the peptide tag. In particular, in addition to comprising a residue that is involved in the formation of the isopeptide bond (i.e. a lysine or asparagine/aspartate) the peptide binding partner comprises a glutamic acid or aspartic acid residue that facilitates or induces the formation of the isopeptide bond between the peptide linkers, e.g. the peptide tag and peptide binding partner.

Thus, a peptide binding partner may comprise a fragment of an isopeptide protein which overlaps with a fragment designed to constitute a peptide tag or may comprise a discrete and separate fragment of the isopeptide protein compared to that of the peptide tag. Thus, the sequence of the peptide binding partner may overlap with that of the designed peptide tag or the peptide tag and peptide binding partner may comprise or consist of two discrete fragments of the isopeptide protein. In some embodiments, the peptide tag may not be based on the sequence of the isopeptide protein, e.g. the peptide tag (peptide linker) may be designed de novo.

Whilst there is no particular limit on the size of a peptide binding partner, practically it is preferable to minimise the size of the peptide linkers for use in the methods and uses of the invention.

Thus, in some embodiments, the peptide linker (e.g. peptide binding partner) may be between 50-300 amino acids in length, e.g. 60-250, 70-225, 80-200 amino acids in length, e.g. it may comprise or consist of 60, 65, 70, 75, 80, 85, 90, 95, 100, 110, 120, 130, 140, 150, 160, 170, 180, 190 or 200 amino acids.

Accordingly, in some embodiments, a pair of peptide linkers comprises a peptide tag and a peptide binding partner, wherein said peptide linkers react spontaneously to form an isopeptide bond.

When the isopeptide bond formation between the peptide linkers is not spontaneous (e.g. when the peptide linkers are both peptide tags) the peptide that induces or catalyzes the formation of the isopeptide bond between said peptide tags/linkers may be viewed as a peptide (e.g. a peptide ligase) derived from an isopeptide protein or a peptide binding partner as defined above. In particular, the peptide comprises a glutamic acid or aspartic acid residue that facilitates or induces the formation of the isopeptide bond between the peptide linkers, but importantly the ligase does not contain an amino acid residue that reacts to form an isopeptide bond with either of the peptide linkers in the peptide linker pair. In some embodiments, the peptide ligase may be between 50-300 amino acids in length, e.g. 60-250, 70-225, 80-200 amino acids in length, e.g. it may comprise or consist of 60, 65, 70, 75, 80, 85, 90, 95, 100, 110, 120, 130, 140, 150, 160, 170, 180, 190 or 200 amino acids.

Thus, a peptide linker (e.g. peptide tag and/or peptide binding partner) therefore does not consist of the entire protein sequence of an isopeptide protein and is shorter in length. For instance, a peptide linker may comprise less than 5, 10, 20, 30, 40 or 50% of the number of amino acid residues present in the isopeptide protein.

Whilst a peptide linker or pair of peptide linkers can be based upon a sequence of an isopeptide protein (particularly one or more fragments thereof), it will be readily understood by the skilled person that the sequence of the peptide linker may differ from the sequence of the portion of the isopeptide protein from which it is derived. Thus, in some embodiments the peptide linker or pair of peptide linkers may comprise mutations or alterations as compared to the sequence of the isopeptide protein from which it is derived. As discussed below, some mutations may be introduced to the peptide linker sequence to improve the stability and/or function of the peptide linker, e.g. to improve the reaction rate of the spontaneous isopeptide bond formation between the peptide linkers.

Thus, in some embodiments, a peptide linker may comprise or consist of a fragment of an isopeptide protein, wherein the fragment fulfils the size criteria set forth above and comprises at least 70, 75, 80, 85, 90, 95, 96, 97, 98, 99 or 100% sequence identity to a comparable region of the isopeptide protein from which is was derived.

Moreover, as noted above, isopeptide proteins may be identified by searching for structural homologues of known isopeptide proteins, i.e. proteins with sequence similarity or identity to known isopeptide proteins. Such homologues may be viewed as functionally equivalent proteins and may find utility in the production of peptides linkers of the present invention.

In some embodiments, a pair of peptide linkers for use in the methods and uses of the invention may be derived from any suitable isopeptide protein. As mentioned above, various isopeptide proteins are known in the art. For instance, peptide linkers may be derived from the major pilin protein Spy0128, which has an amino acid sequence as set out in SEQ ID NO. 23 and is encoded by a nucleotide sequence as set out in SEQ ID NO. 24. Two isopeptide bonds are formed in the protein. One isopeptide bond is formed between lysine at position 179 in SEQ ID NO. 23 and asparagine at position 303 in SEQ ID NO. 23 (the reactive residues). The glutamic acid residue which induces the spontaneous isopeptide bond is found at position 258 in SEQ ID NO. 23. Thus, a pair of peptide linkers developed from an isopeptide protein set forth in SEQ ID NO: 23 will preferably comprise a peptide linker comprising a fragment of the protein comprising the reactive asparagine at position 303 and a peptide linker comprising a fragment of the protein comprising the reactive lysine at position 179. In some embodiments, one of the peptide linkers will comprise a fragment that also contains the glutamic acid residue at position 258. In some embodiments, a fragment of the protein comprising the glutamic acid residue at position 258 may be provided separately, i.e. as a peptide ligase as defined above.

Another isopeptide bond in the major pilin protein Spy0128 occurs between the lysine residue at position 36 of SEQ ID NO. 23 and the asparagine residue at position 168 of SEQ ID NO. 23. The glutamic acid residue which induces isopeptide formation is found at position 117 in SEQ ID NO. 23. Thus, a pair of peptide linkers developed from an isopeptide protein set forth in SEQ ID NO: 23 will preferably comprise a peptide linker comprising a fragment of the protein comprising the reactive lysine residue at position 36 and a peptide linker comprising a fragment of the protein comprising the reactive asparagine at position 168. In some embodiments, one of the peptide linkers will comprise a fragment that also contains the glutamic acid residue at position 117. In some embodiments, a fragment of the protein comprising the glutamic acid residue at position 117 may be provided separately, i.e. as a peptide ligase as defined above.

ACE19, a domain of an adhesin protein from *E. faecalis*, also spontaneously forms an isopeptide bond. ACE19 has an amino acid sequence as set forth in SEQ ID NO. 27 and is encoded by a nucleotide sequence as set forth in SEQ ID NO. 28.

The isopeptide bond occurs between a lysine residue at position 181 of SEQ ID NO. 27 and an asparagine residue at position 294 of SEQ ID NO. 27. The bond is induced by an aspartic acid residue at position 213 in SEQ ID NO. 27. Thus, a pair of peptide linkers developed from isopeptide protein set forth in SEQ ID NO: 27 will preferably comprise a peptide linker comprising a fragment of the protein comprising the reactive asparagine residue at position 294 and a peptide linker comprising a fragment of the protein comprising the reactive lysine residue at position 181. In some embodiments, one of the peptide linkers will comprise a fragment that also contains the aspartic acid residue at position 213. In some embodiments, a fragment of the protein comprising the aspartic acid residue at position 213 may be provided separately, i.e. as a peptide ligase as defined above.

The collagen binding domain from *S. aureus* which has an amino acid sequence set out in SEQ ID NO. 29, comprises one spontaneously formed isopeptide bond. The isopeptide bond occurs between lysine at position 176 of SEQ ID NO. 29 and asparagine at position 308 of SEQ ID NO. 29. The aspartic acid residue which induces the isopeptide bond is at position 209 of SEQ ID NO. 29. Thus, a pair of peptide linkers developed from the isopeptide protein set forth in SEQ ID NO: 29 will preferably comprise a peptide linker comprising a fragment of the protein comprising the reactive lysine at position 176 and a peptide linker comprising a fragment of the protein comprising the reactive asparagine at position 308. In some embodiments, one of the peptide linkers will comprise a fragment that also contains the aspartic acid residue at position 209. In some embodiments, a fragment of the protein comprising the aspartic acid residue at position 209 may be provided separately, i.e. as a peptide ligase as defined above.

FbaB from *Streptococcus pyogenes* comprises a domain, CnaB2, which has an amino acid sequence set out in SEQ ID NO. 25, is encoded by the nucleotide sequence set out in SEQ ID NO.26 and which comprises one spontaneously formed isopeptide bond. The isopeptide bond in the CnaB2 domain forms between a lysine at position 15 of SEQ ID NO. 25 and an aspartic acid residue at position 101 of SEQ ID NO. 25. The glutamic acid residue which induces the isopeptide bond is at position 61 of SEQ ID NO. 25. Thus, a pair of peptide linkers developed from the isopeptide protein set forth in SEQ ID NO: 25 will preferably comprise a peptide linker comprising a fragment of the protein comprising the reactive lysine at position 15 and a peptide linker comprising a fragment of the protein comprising the reactive aspartic acid at position 101. In some embodiments, one of the peptide linkers will comprise a fragment that also contains the glutamic acid residue at position 61. In some embodiments, a fragment of the protein comprising the glutamic acid residue at position 61 may be provided separately, i.e. as a peptide ligase as defined above (e.g. SEQ ID NO: 34).

The RrgA protein is an adhesion protein from *Streptococcus pneumoniae*, which has an amino acid sequence as set out in SEQ ID NO. 21 and is encoded by a nucleotide sequence as set out in SEQ ID NO. 22. An isopeptide bond is formed between lysine at position 742 in SEQ ID NO. 21 and asparagine at position 854 in SEQ ID NO. 21. The bond is induced by a glutamic acid residue at position 803 in SEQ ID NO. 21. Thus, a pair of peptide linkers developed from the isopeptide protein set forth in SEQ ID NO: 21 will preferably comprise a peptide linker comprising a fragment of the protein comprising the reactive asparagine at position 854 and a peptide linker comprising a fragment of the protein comprising the reactive lysine at position 742. In some embodiments, one of the peptide linkers will comprise a fragment that also contains the glutamic acid residue at position 803. In some embodiments, a fragment of the protein comprising the glutamic acid residue at position 803 may be provided separately, i.e. as a peptide ligase as defined above.

The PsCs protein is a fragment of the por secretion system C-terminal sorting domain protein from *Streptococcus intermedius*, which has an amino acid sequence as set out in SEQ ID NO. 31 and is encoded by a nucleotide sequence as set out in SEQ ID NO. 32. An isopeptide bond is formed between lysine at position 405 in SEQ ID NO. 31 and aspartate at position 496 in SEQ ID NO. 31. Thus, a pair of peptide linkers developed from the isopeptide protein set forth in SEQ ID NO: 31 will preferably comprise a peptide linker comprising a fragment of the protein comprising the reactive aspartate at position 496 and a peptide linker comprising a fragment of the protein comprising the reactive lysine at position 405.

Thus, in some embodiments, a pair of peptide linkers for use in the method of the invention may be derived from an isopeptide protein comprising an amino acid sequence as set forth in any one of SEQ ID NOs: 21, 23, 25, 27, 29 or 31 or a protein with at least 70% sequence identity to an amino acid sequence as set forth in any one of SEQ ID NOs: 21, 23, 25, 27, 29 or 31.

In some embodiments, said isopeptide protein sequence above is at least 75, 80, 85, 90, 95, 96, 97, 98, 99 or 100% identical to the sequence (SEQ ID NOs: 21, 23, 25, 27, 29 or 31) to which it is compared.

Preferably, peptide linkers derived from the isopeptide proteins defined above fulfil the size and sequence identity criteria described above.

Sequence identity may be determined by any suitable means known in the art, e.g. using the SWISS-PROT protein sequence databank using FASTA pep-cmp with a variable pamfactor, and gap creation penalty set at 12.0 and gap extension penalty set at 4.0, and a window of 2 amino acids. Other programs for determining amino acid sequence identity include the BestFit program of the Genetics Computer Group (GCG) Version 10 Software package from the University of Wisconsin. The program uses the local homology algorithm of Smith and Waterman with the default values: Gap creation penalty—8, Gap extension penalty=2, Average match=2.912, Average mismatch=−2.003.

Preferably said comparison is made over the full length of the sequence, but may be made over a smaller window of comparison, e.g. less than 200, 100 or 50 contiguous amino acids.

Preferably such sequence identity-related proteins are functionally equivalent to the polypeptides which are set forth in the recited SEQ ID NOs. As referred to herein, "functional equivalence" refers to homologues of the isopeptide proteins discussed above that may show some reduced efficacy in spontaneously forming isopeptide bonds relative to the parent molecule (i.e. the molecule with which it shows sequence homology), but preferably are as efficient or are more efficient.

In some embodiments, orthogonal pairs of peptide linkers may be derived from any two or more of the isopeptide proteins defined above. In preferred embodiments, a first pair of peptide linkers is derived from an isopeptide protein having an amino acid sequence as set forth in SEQ ID NO: 21 and a second, orthogonal, pair of peptide linkers is derived from an isopeptide protein having an amino acid sequence as set forth in SEQ ID NO: 25. As discussed below, in some embodiments, two orthogonal pairs of peptide linkers may be derived from the same isopeptide protein, e.g. SEQ ID NO: 21. Other orthogonal pairs of peptide linkers may be derived from isopeptide proteins having amino acid sequences as set forth in SEQ ID NOs: 21 and 23, 21 and 27, 21 and 29, 21 and 31, 25 and 27, 25 and 29 or 25 and 31. The skilled person readily would be able to determine whether any two pairs of peptide linkers are orthogonal based on the methods disclosed herein, particularly the Examples. For instance, various combinations of peptide linkers from different pairs of peptide linkers may be contacted, e.g. in solution, for a suitable period of time, e.g. 1-24 hours, under conditions that facilitate isopeptide bond formation, e.g. in PBS at pH 4-9, e.g. pH 7, at 1-40° C., e.g. 25° C. The sample may be analysed, e.g. by gel electrophoresis (e.g. SDS-PAGE), to determine whether any of the peptide linkers have reacted, i.e. by looking for conjugated peptides, see e.g. FIG. 7. Thus, orthogonal pairs of peptide linkers for use in the method of the invention may be derived from any suitable combination of isopeptide proteins.

The inventor has advantageously developed pairs of peptide linkers that find particular utility in the methods and uses of the invention. In this respect, the inventor has determined that peptide linker pairs may be derived from the RrgA protein as defined above. However, as described in detail in the Examples below, the inventor introduced mutations into the peptide linkers relative to the native RrgA sequence to improve the reactivity of the peptide linkers. Specifically, a glycine residue was replaced with a threonine residue to stabilize a β-strand and an aspartate residue was replaced with a glycine residue to stabilize a hairpin turn close to the reaction site.

Thus, the present invention provides a peptide linker comprising:

(i) an amino acid sequence as set forth in SEQ ID NO: 1 or a sequence with at least 70% sequence identity to an amino acid sequence as set forth in SEQ ID NO: 1, wherein said amino acid sequence comprises a lysine residue at position 9; or (ii) an amino acid sequence as set forth in SEQ ID NO: 2 or a sequence with at least 70% sequence identity to an amino acid sequence as set forth in SEQ ID NO: 2, wherein said amino acid sequence comprises a glutamate or aspartate residue at position 55, a threonine residue at position 94, a glycine residue at position 100 and an asparagine or aspartate residue at position 106.

In some embodiments, the peptide linker in (i) comprises an amino acid sequence as set forth in SEQ ID NO: 38 and/or the peptide linker in (ii) comprises an amino acid sequence as set forth in SEQ ID NO: 39.

In a further embodiment, the present invention provides a peptide linker comprising:

(i) an amino acid sequence as set forth in SEQ ID NO: 5 or a sequence with at least 70% sequence identity to an amino acid sequence as set forth in SEQ ID NO: 5, wherein said amino acid sequence comprises an aspartate or asparagine residue at position 8; or (ii) an amino acid sequence as set forth in SEQ ID NO: 6 or a sequence with at least 70% sequence identity to an amino acid sequence as set forth in SEQ ID NO: 6, wherein said amino acid sequence comprises a lysine residue at position 8.

In some embodiments, the peptide linker in (i) comprises an amino acid sequence as set forth in SEQ ID NO: 42 and/or the peptide linker in (ii) comprises an amino acid sequence as set forth in SEQ ID NO: 43.

In a still further embodiment, the present invention provides a peptide linker comprising:

(i) an amino acid sequence as set forth in SEQ ID NO: 9 or a sequence with at least 70% sequence identity to an amino acid sequence as set forth in SEQ ID NO: 9, wherein said amino acid sequence comprises an asparagine or aspartate residue at position 17; or (ii) an amino acid sequence as set forth in SEQ ID NO: 10 or a sequence with at least 70% sequence identity to an amino acid sequence as set forth in SEQ ID NO: 10, wherein said amino acid sequence comprises a lysine residue at position 9 and a glutamate or aspartate residue at position 70.

In some embodiments, the peptide linker in (i) comprises an amino acid sequence as set forth in SEQ ID NO: 109 or a sequence with at least 70% sequence identity to an amino acid sequence as set forth in SEQ ID NO: 109, wherein said amino acid sequence comprises an asparagine or aspartate residue at position 17, a glycine residue at position 11 and preferably an isoleucine residue at position 20, a proline residue at positions 21 and 22 and a lysine residue at position 23.

In some embodiments, the peptide linker in (i) comprises an amino acid sequence as set forth in SEQ ID NO: 46 and/or the peptide linker in (ii) comprises an amino acid sequence as set forth in SEQ ID NO: 47.

In some embodiments, said peptide linker sequence above is at least 75, 80, 85, 90, 95, 96, 97, 98, 99 or 100% identical to the sequence (SEQ ID NOs: 1, 2, 5, 6, 9, 10 or 109) to which it is compared.

In preferred embodiments, the peptide linker defined in each part (i) above is capable of spontaneously forming an isopeptide bond with a peptide linker comprising an amino acid sequence as defined in each respective part (ii) above. For instance, a peptide linker comprising an amino acid sequence as set forth in SEQ ID NO: 1 or variant thereof is capable of spontaneously forming an isopeptide bond with a peptide linker comprising an amino acid sequence as set forth in SEQ ID NO: 2 or a variant thereof. Similarly, peptides comprising SEQ ID NOs: 5 and 6 or variants thereof are capable of spontaneously forming an isopeptide bond with each other, and peptides comprising SEQ ID NOs: 9 and 10 or variants thereof (e.g. SEQ ID NO: 109) are capable of spontaneously forming an isopeptide bond with each other (e.g. SEQ ID NOs: 109 and 10).

Thus, the invention provides a pair of peptide linkers that can be used in the methods and uses of the invention comprising:

(1) peptide linkers comprising SEQ ID NOs: 1 and 2 or variants thereof as defined above, e.g. SEQ ID NOs: 38 and 39;

(2) peptide linkers comprising SEQ ID NOs: 5 and 6 or variants thereof as defined above, e.g. SEQ ID NOs: 42 and 43;

(3) peptide linkers comprising SEQ ID NOs: 9 and 10 or variants thereof as defined above, e.g. SEQ ID NOs: 46 and 47; or (4) peptide linkers comprising SEQ ID NOs: 109 and 10 or variants thereof as defined above.

Thus, each pair of peptide linkers defined above may be defined as a cognate peptide linker pair.

In some embodiments, each peptide linker pair defined above (i.e. each cognate peptide linker pair) may be viewed as being orthogonal (i.e. non-cognate) to the other peptide linker pairs, e.g. pair (1) is orthogonal to pair (2), (3) and/or pair (4), pair (2) is orthogonal to pair (1), (3) and/or pair (4), pair (3) is orthogonal to pair (1) and/or pair (2) and pair (4) is orthogonal to pair (1) and/or (2). In some embodiments, these orthogonal pairs represent preferred orthogonal (non-cognate) pairs of peptide (cognate) linkers for use in the methods and uses of the invention. Further preferred orthogonal pairs of peptide linkers are defined below.

As discussed above, the peptide linkers of the invention find particular utility in the synthesis of fusion proteins, wherein the peptide linkers are incorporated in (e.g. form domains of, or are linked to) a protein unit to be linked (conjugated) to another protein unit to form a fusion protein. Thus, in further embodiments, the invention provides a recombinant or synthetic polypeptide comprising polypeptide and a peptide linker as defined above.

It will be evident that the peptide linkers of the invention may find utility in other methods and uses, e.g. as peptide tags as described in WO2011/098772 (herein incorporated by reference).

Other peptide linkers that may be used in the methods and uses of the invention include:

(i) an amino acid sequence as set forth in SEQ ID NO: 13 or a sequence with at least 70% sequence identity to an amino acid sequence as set forth in SEQ ID NO: 13, wherein said amino acid sequence comprises an aspartate or asparagine residue at position 7; or (ii) an amino acid sequence as set forth in SEQ ID NO: 14 or a sequence with at least 70% sequence identity to an amino acid sequence as set forth in SEQ ID NO: 14, wherein said amino acid sequence comprises a glutamate or aspartate residue at position 56, and a lysine residue at position 10; or (iii) an amino acid sequence as set forth in SEQ ID NO: 33 or a sequence with at least 70% sequence identity to an amino acid sequence as set forth in SEQ ID NO: 33, wherein said amino acid sequence comprises a lysine residue at position 8; or (iv) an amino acid sequence as set forth in SEQ ID NO: 17 or a sequence with at least 70% sequence identity to an amino acid sequence as set forth in SEQ ID NO: 17, wherein said amino acid sequence comprises an aspartate or asparagine residue at position 11; or (v) an amino acid sequence as set forth in SEQ ID NO: 18 or a sequence with at least 70% sequence identity to an amino acid sequence as set forth in SEQ ID NO: 18, wherein said amino acid sequence comprises a glutamate or aspartate residue at position 241 and a lysine residue at position 162.

In some embodiments, said peptide linker sequence above is at least 75, 80, 85, 90, 95, 96, 97, 98, 99 or 100% identical to the sequence (SEQ ID NOs: 13, 14, 17, 18, or 33) to which it is compared.

Other peptide linker pairs that may be used in the methods and uses of the invention include:

(5) peptide linkers comprising SEQ ID NOs: 13 and 14 or variants thereof as defined above;

(6) peptide linkers comprising SEQ ID NOs: 13 and 33 or variants thereof as defined above; or (7) peptide linkers comprising SEQ ID NOs: 17 and 18 or variants thereof as defined above.

In some embodiments, where the cognate peptide linker pair comprises the pair defined in (6) above, the reaction also comprises a component that induces or catalyzes the formation of the isopeptide bond. For instance, the reaction comprises a peptide ligase, preferably wherein said peptide ligase comprises an amino acid sequence as set forth in SEQ ID NO: 34 or a sequence with at least 70% sequence identity to an amino acid sequence as set forth in SEQ ID NO: 34.

In some embodiments, said peptide ligase sequence above is at least 75, 80, 85, 90, 95, 96, 97, 98, 99 or 100% identical to the sequence (SEQ ID NO: 34) to which it is compared.

Whilst any orthogonal pairs of peptide linker pairs selected from (1)-(7) above may be used in the methods and uses of the invention, particularly preferred orthogonal pairs of peptide linkers include any one of the following pairs, which are defined above: (1) and (4), (1) and (5), (1) and (6), (1) and (3), (1) and (2), (2) and (4), (2) and (5), (2) and (6), (3) and (5), (3) and (6), (4) and (5) and (4) and (6).

The position of the peptide linker within a protein to be linked to another protein to form a fusion protein is not particularly important Thus, in some embodiments the peptide linker may be located at the N-terminus or C-terminus of the recombinant or synthetic polypeptide or a protein to be linked in the fusion protein. In some embodiments, the peptide linker may be located internally within the recombinant or synthetic polypeptide or a protein to be linked in the fusion protein. Thus, in some embodiments the peptide linker may be viewed as an N-terminal, C-terminal or internal domain of the recombinant or synthetic polypeptide or a protein to be linked in the fusion protein.

In some embodiments, it may be useful to include one or more spacers, e.g. a peptide spacer, between the protein to be joined in or to the fusion protein and the peptide linker. Thus, the protein and peptide linker may be linked directly to each other or they may be linked indirectly by means of one or more spacer sequences. Thus, a spacer sequence may interspace or separate two or more individual parts of the recombinant or synthetic polypeptide or a protein to be linked in the fusion protein. In some embodiments, a spacer may be N-terminal or C-terminal to the peptide linker. In some embodiments, spacers may be at both sides of the peptide linker.

The precise nature of the spacer sequence is not critical and it may be of variable length and/or sequence, for example it may have 1-40, more particularly 2-20, 1-15, 1-12, 1-10, 1-8, or 1-6 residues, e.g. 6, 7, 8, 9, 10 or more residues. By way of representative example the spacer sequence, if present, may have 1-15, 1-12, 1-10, 1-8 or 1-6 residues etc. The nature of the residues is not critical and they may for example be any amino acid, e.g. a neutral amino acid, or an aliphatic amino acid, or alternatively they may be hydrophobic, or polar or charged or structure-forming e.g. proline. In some preferred embodiments, the linker is a serine and/or glycine-rich sequence.

Exemplary spacer sequences thus include any single amino acid residue, e.g. S, G, L, V, P, R, H, M, A or E or a di-, tri- tetra- penta- or hexa-peptide composed of one or more of such residues. Representative and preferred spacer sequences comprise an amino acid sequence as set forth in SEQ ID NO: 36 or 37.

The recombinant or synthetic polypeptides of the invention may also comprise purification moieties or tags to facilitate their purification (e.g. prior to use in the methods and uses of the invention and/or during the extension of the fusion protein as discussed below). Any suitable purification moiety or tag may be incorporated into the polypeptide and such moieties are well known in the art. For instance, in some embodiments, the recombinant or synthetic peptide may comprise a peptide purification tag or moiety, e.g. a His-tag sequence. Such purification moieties or tags may be incorporated at any position within the polypeptide. In some preferred embodiments, the purification moiety is located at or towards (i.e. within 5, 10, 15, 20 amino acids of) the N- or C-terminus of the polypeptide.

Representative recombinant or synthetic polypeptides of the invention include polypeptides with an amino acid sequence as set forth in any one of SEQ ID NOs: 50-59 or a sequence with at least 70% sequence identity to an amino acid sequence as set forth in any one of SEQ ID NOs: 50-59, wherein said polypeptides comprise a peptide linker as defined above.

Preferably the recombinant or synthetic polypeptide fulfils the sequence identity requirements defined above, e.g. is at least 75, 80, 85, 90, 95, 96, 97, 98, 99 or 100% identical to the sequence to which it is compared.

As noted above, an advantage of the present invention arises from the fact that the peptide linkers incorporated in the proteins (e.g. the recombinant or synthetic polypeptides of the invention) to be joined together to form a fusion protein may be completely genetically encoded. Thus, in a further aspect, the invention provides a nucleic acid molecule encoding a peptide linker or polypeptide as defined above.

In some embodiments, the nucleic acid molecule encoding a peptide linker defined above comprises a nucleotide sequence as set forth in any one of SEQ ID NOs: 3, 4, 7, 8, 11, 12, 40, 41, 44, 45, 48, 49 or 110 or a nucleotide sequence with at least 70% sequence identity to a sequence as set forth in any one of SEQ ID NOs: 3, 4, 7, 8, 11, 12, 40, 41, 44, 45, 48, 49 or 110.

In some embodiments, the nucleic acid molecule encoding a recombinant or synthetic polypeptide defined above comprises a nucleotide sequence as set forth in any one of SEQ ID NOs: 60-69 or a nucleotide sequence with at least 70% sequence identity to a sequence as set forth in any one of SEQ ID NOs: 60-69.

Preferably, the nucleic acid molecule above is at least 75, 80, 85, 90, 95, 96, 97, 98, 99 or 100% identical to the sequence to which it is compared.

Nucleic acid sequence identity may be determined by, e.g. FASTA Search using GCG packages, with default values and a variable pamfactor, and gap creation penalty set at 12.0 and gap extension penalty set at 4.0 with a window of 6 nucleotides. Preferably said comparison is made over the full length of the sequence, but may be made over a smaller window of comparison, e.g. less than 600, 500, 400, 300, 200, 100 or 50 contiguous nucleotides.

The nucleic acid molecules of the invention may be made up of ribonucleotides and/or deoxyribonucleotides as well as synthetic nucleotide residues that are capable of participating in Watson-Crick type or analogous base pair interactions. Preferably, the nucleic acid molecule is DNA or RNA. The nucleic acid molecules described above may be operatively linked to an expression control sequence, or a recombinant DNA cloning vehicle or vector containing such a recombinant DNA molecule. This allows intracellular expression of the proteins for use in the methods and uses of the invention, e.g. the expression of the polypeptides of the invention, as a gene product, the expression of which is directed by the gene(s) introduced into cells of interest Gene expression is directed from a promoter active in the cells of interest and may be inserted in any form of linear or circular nucleic acid (e.g. DNA) vector for incorporation in the genome or for independent replication or transient transfection/expression. Suitable transformation or transfection techniques are well described in the literature. Alternatively, the naked nucleic acid (e.g. DNA) molecule may be introduced directly into the cell for the production of proteins and polypeptide of, and for use in, the invention. Alternatively the nucleic acid may be converted to mRNA by in vitro transcription and the relevant proteins may be generated by in vitro translation.

Appropriate expression vectors include appropriate control sequences such as for example translational (e.g. start and stop codons, ribosomal binding sites) and transcriptional control elements (e.g. promoter-operator regions, termination stop sequences) linked in matching reading frame with the nucleic acid molecules of the invention. Appropriate vectors may include plasmids and viruses (including both bacteriophage and eukaryotic viruses). Suitable viral vectors include baculovirus and also adenovirus, adeno-associated virus, herpes and vaccinia/pox viruses. Many other viral vectors are described in the art. Preferred vectors include bacterial and mammalian expression vectors pGEX-KG, pEF-neo and pEF-HA.

As noted above, the polypeptide of the invention may comprise additional sequences (e.g. peptide/protein tags to facilitate purification of the polypeptide) and thus the nucleic acid molecule may conveniently be fused with DNA encoding an additional peptide or polypeptide, e.g. His-tag, maltose-binding protein, to produce a fusion protein on expression.

Thus viewed from a further aspect, the present invention provides a vector, preferably an expression vector, comprising a nucleic acid molecule as defined above.

Other aspects of the invention include methods for preparing recombinant nucleic acid molecules according to the invention, comprising inserting nucleic acid molecule of the invention encoding the peptide linkers and/or polypeptides of the invention into vector nucleic acid.

Nucleic acid molecules of the invention, preferably contained in a vector, may be introduced into a cell by any appropriate means. Suitable transformation or transfection techniques are well described in the literature. A variety of techniques are known and may be used to introduce such vectors into prokaryotic or eukaryotic cells for expression. Preferred host cells for this purpose include insect cell lines, yeast, mammalian cell lines or E. coli, such as strain BL21/DE3. The invention also extends to transformed or transfected prokaryotic or eukaryotic host cells containing a nucleic acid molecule, particularly a vector as defined above.

Thus, in another aspect, there is provided a recombinant host cell containing a nucleic acid molecule and/or vector as described above.

By "recombinant" is meant that the nucleic acid molecule and/or vector has been introduced into the host cell. The host cell may or may not naturally contain an endogenous copy of the nucleic acid molecule, but it is recombinant in that an exogenous or further endogenous copy of the nucleic acid molecule and/or vector has been introduced.

A further aspect of the invention provides a method of preparing a peptide linker and/or polypeptide of the invention as hereinbefore defined, which comprises culturing a host cell containing a nucleic acid molecule as defined above, under conditions whereby said nucleic acid molecule encoding said peptide linker and/or polypeptide is expressed and recovering said molecule (peptide linker and/or polypeptide) thus produced. The expressed peptide linker and/or polypeptide forms a further aspect of the invention.

In some embodiments, the peptide linkers and/or polypeptides of the invention, or for use in the method and uses of the invention, may be generated synthetically, e.g. by ligation of amino acids or smaller synthetically generated peptides, or more conveniently by recombinant expression of a nucleic acid molecule encoding said polypeptide as described hereinbefore.

Nucleic acid molecules of the invention may be generated synthetically by any suitable means known in the art.

Thus, the peptide linker and/or polypeptide of the invention may be an isolated, purified, recombinant or synthesized peptide linker or polypeptide. As noted above, the term "polypeptide" is used herein interchangeably with the term "protein". As noted above, the term polypeptide or protein typically includes any amino acid sequence comprising at least 40 consecutive amino acid residues, e.g. at least 50, 60, 70, 80, 90, 100, 150 amino acids, such as 40-1000, 50-900, 60-800, 70-700, 80-600, 90-500, 100-400 amino acids.

Similarly, the nucleic acid molecules of the invention may be an isolated, purified, recombinant or synthesized nucleic acid molecule.

Thus, alternatively viewed, the peptide linkers, polypeptides and nucleic acid molecules of the invention preferably are non-native, i.e. non-naturally occurring, molecules.

Standard amino acid nomenclature is used herein. Thus, the full name of an amino acid residue may be used interchangeably with one letter code or three letter abbreviations. For instance, lysine may be substituted with K or Lys, isoleucine may be substituted with I or Ile, and so on. Moreover, the terms aspartate and aspartic acid, and glutamate and glutamic acid are used interchangeably herein and may be replaced with asp or D, or glu or E, respectively.

Whilst it is envisaged that the peptide linkers and polypeptides of, and for use in, the invention may be produced recombinantly, and this is a preferred embodiment of the invention, it will be evident that the peptide linkers of the invention may be conjugated to proteins to be joined in a fusion protein by other means. In other words, the peptide linker and protein may be produced separately by any suitable means, e.g. recombinantly, and subsequently conjugated (joined) to form a peptide linker-protein conjugate that can be used in the methods of the invention. For instance, the peptide linkers of the invention may be produced synthetically or recombinantly, as described above, and conjugated to a protein (to be linked in a fusion protein according to the method of the invention) via a non-peptide linker or spacer, e.g. a chemical linker or spacer.

Thus, in some embodiments, the peptide linker and protein to be incorporated into a fusion may be joined together either directly through a bond or indirectly through a linking group. Where linking groups are employed, such groups may be chosen to provide for covalent attachment of the peptide linker and protein component through the linking group. Linking groups of interest may vary widely depending on the nature of the protein component. The linking group, when present, is in many embodiments biologically inert.

A variety of linking groups are known to those of skill in the art and find use in the invention. In representative embodiments, the linking group is generally at least about 50 daltons, usually at least about 100 daltons and may be as large as 1000 daltons or larger, for example up to 1000000 daltons if the linking group contains a spacer, but generally will not exceed about 500 daltons and usually will not exceed about 300 daltons. Generally, such linkers will comprise a spacer group terminated at either end with a reactive functionality capable of covalently bonding to the peptide linker and protein component. Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject blocking reagent include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

In some embodiments, it may be useful to modify one or more residues in the peptide linker and/or protein to facilitate the conjugation of these molecules and/or to improve the stability of the peptide linker and/or protein. Thus, in some embodiments, the peptide linker, polypeptide or protein of, or for use in, the invention may comprise unnatural or non-standard amino acids.

In some embodiments, the peptide linker, polypeptide or protein of, or for use in, the invention may comprise one or more, e.g. at least 1, 2, 3, 4, 5 non-conventional amino acids, such as 10, 15, 20 or more non-conventional, i.e. amino acids which possess a side chain that is not coded for by the standard genetic code, termed herein "non-coded amino acids" (see e.g. Table 1). These may be selected from amino acids which are formed through metabolic processes such as ornithine or taurine, and/or artificially modified amino acids such as 9H-fluoren-9-ylmethoxycarbonyl (Fmoc), (tert)-(B) utyl (o)xy (c)arbonyl (Boc), 2,2,5,7,8-pentamethylchroman-6-sulphonyl (Pmc) protected amino acids, or amino acids having the benzyloxy-carbonyl (Z) group.

Examples of non-standard or structural analogue amino acids which may be used in the peptide linkers or polypeptides of, and for use in, the invention are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids. Examples of non-conventional, i.e. non-coded, amino acids are listed in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |

TABLE 1-continued

| Non-conventional amino acid | Code | Non-conventional amino acid | Code |
|---|---|---|---|
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpencillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | L-O-methyl serine | Omser |
| | | L-O-methyl homoserine | Omhse |

In some embodiments the method of the present invention may be performed heterogeneously (as described above), using a solid phase, for example, in which the growing fusion protein, preferably the first or second protein in the fusion protein chain may be immobilized on a solid phase, permitting the use of washing steps. Thus, in some embodiments, the method is a solid phase method (i.e. a heterogeneous method). Alternatively viewed, the method is performed on a solid phase or solid substrate. The use of solid phase assays offers advantages. For instance, washing steps can assist in the removal of excess, unreacted proteins and/or components that may interfere with subsequent rounds of reaction (i.e. the addition of further proteins to the fusion protein), e.g. peptide ligases, components involved in unblocking (uncaging, unmasking, deprotecting) peptide linkers etc.

Immobilization of the fusion protein on a solid phase may be achieved in various ways. The fusion protein may be immobilized, i.e. bound to the support, in any convenient way. In some embodiments, the first or second protein of the fusion protein is immobilized on a solid support. Thus, in some embodiments, the method may comprise a step of immobilizing the first protein on a solid support. In some embodiments, the method may comprise a step of immobilizing the linked protein, comprising the first and second protein, on a solid support.

Thus the manner or means of immobilization and the solid support may be selected, according to choice, from any number of immobilization means and solid supports as are widely known in the art and described in the literature. Thus, the fusion protein may be directly bound to the support, for example via a domain or moiety of at least one protein in the fusion protein (e.g. chemically cross-linked). In some embodiments, the fusion protein may be bound indirectly by means of a linker group, or by an intermediary binding group(s) (e.g. by means of a biotin-streptavidin interaction). Thus, the fusion protein may be covalently or non-covalently linked to the solid support. The linkage may be a reversible (e.g. cleavable) or irreversible linkage. Thus, in some embodiments, the linkage may be cleaved enzymatically, chemically or with light, e.g. the linkage may be a light-sensitive linkage.

Thus, in some embodiments, a protein to be included in the fusion protein may be provided with means for immobilization (e.g. an affinity binding partner, e.g. biotin or a hapten, capable of binding to its binding partner, i.e. a cognate binding partner, e.g. streptavidin or an antibody) provided on the support. In some embodiments, the protein to be immobilized on the support may be a binding protein, e.g. maltose binding protein, antibody etc. The interaction between the fusion protein and the solid support must be robust enough to allow for washing steps, i.e. the interaction between the fusion protein and solid support is not disrupted (significantly disrupted) by the washing steps. For instance, it is preferred that with each washing step, less than 5%, preferably less than 4, 3, 2, 1, 0.5 or 0.1% of the fusion protein is removed or eluted from the solid phase. In this respect, the inventor has developed a modified maltose binding protein that has an improved binding affinity for maltose and therefore finds particular utility in the methods of the invention.

Thus, a further aspect of the invention provides a maltose binding protein comprising an amino acid sequence as set forth in SEQ ID NO: 70 or a sequence with at least 70% identity with an amino acid sequence as set forth in SEQ ID NO: 70.

In some embodiments, the maltose binding protein above is at least 75, 80, 85, 90, 95, 96, 97, 98, 99 or 100% identical to the sequence to which it is compared.

Preferably, a maltose binding protein with at least 70% identity with an amino acid sequence as set forth in SEQ ID NO: 70 is functionally equivalent to a protein consisting of the amino acid sequence as set forth in SEQ ID NO: 70, i.e. is capable of binding maltose with the same affinity as, or with greater affinity than, a protein consisting of the amino acid sequence as set forth in SEQ ID NO: 70. For instance, the maltose binding protein of the invention has a binding affinity for maltose of less than 0.2 µM, e.g. 0.1, 0.08, 0.05, 0.03, or 0.01 µM or less. In preferred embodiments, the maltose binding protein with at least 70% identity with an amino acid sequence as set forth in SEQ ID NO: 70 comprises a valine at positions 312 and 317.

The invention also provides a nucleic acid molecule encoding the maltose binding protein defined above. In some embodiments, the nucleic acid molecule comprises a nucleotide sequence as set forth in SEQ ID NO: 71 or a sequence with at least 70% sequence identity to a nucleotide sequence as set forth in SEQ ID NO: 71.

In some embodiments, the maltose binding protein comprises (e.g. is conjugated to) a peptide linker as defined herein. In still further embodiments, the maltose binding protein comprises more than one (e.g. 2 or 3) amino acid sequences as defined above, i.e. it comprises a repeated sequence.

The fusion protein, e.g. the first protein to be incorporated in fusion protein, may be immobilized before or after it is contacted with a further protein (e.g. second protein) to be incorporated into the fusion protein. Further, such an "immobilizable" fusion protein may be contacted with the further protein together with the support.

The solid support may be any of the well-known supports or matrices which are currently widely used or proposed for immobilization, separation etc. These may take the form of particles (e.g. beads which may be magnetic, para-magnetic or non-magnetic), sheets, gels, filters, membranes, fibres, capillaries, slides, arrays or microtitre strips, tubes, plates or wells etc.

The support may be made of glass, silica, latex or a polymeric material. Suitable are materials presenting a high surface area for binding of the fusion protein. Such supports may have an irregular surface and may be for example porous or particulate e.g. particles, fibres, webs, sinters or sieves. Particulate materials, e.g. beads are useful due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10, and e.g. not more than 6 µm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the isopeptide bond formation steps.

In some embodiments, the solid support is an amylose resin.

Upon the formation of an isopeptide bond between the penultimate and final proteins in the fusion protein, it may be desirable to remove or elute the protein from the solid support. Thus, in some embodiments, the method comprises a step of eluting or removing the fusion protein from the solid support.

As indicated above, in certain protocols the methods of the invention may allow the simultaneous production of two or more fusion proteins on the same solid support, e.g. array. Thus, in some embodiments, the method of the invention may be viewed as a multiplex and/or high throughput format.

In a further embodiment, the invention provides a fusion protein obtained or obtainable from the method of the invention. In some embodiments, the fusion protein is immobilized on a solid substrate. Thus, in yet a further embodiment, the present invention provides a solid substrate comprising at least one fusion protein, obtained or obtainable from the method of the invention. In some embodiments, the solid substrate may be in the form of an array (i.e. a protein array, particularly a fusion protein array) comprising two or more fusion proteins (fusion proteins with different sequences) obtained or obtainable from the method of the invention. In some embodiments, the array comprises at least 10, 20, 50, 100, 200, 300, 400, 500, 1000, 1500, 2000, 5000 or 10000 fusion proteins i.e. different fusion proteins (with different structures or sequences).

In some embodiments, two or more fusion proteins obtained or obtainable from the method of the invention may be mixed together to form a library of fusion proteins. Thus, in a further embodiment, the invention provides a library of fusion proteins comprising at least two fusion proteins, obtained or obtainable from the method of the invention. In some embodiments, the library comprises at least 10, 20, 50, 100, 200, 300, 400, 500, 1000, 1500, 2000, 5000 or 10000 fusion proteins, i.e. different fusion proteins (with different structures or sequences). In some embodiments, the library may comprise fusion proteins immobilized on a solid substrate, e.g. bead or particle. For instance, each solid substrate, e.g. bead or particle, may comprise a different fusion protein.

Whilst the method of the invention has been exemplified using a heterogeneous embodiment, it will be readily apparent from the disclosures herein that the method may be employed homogeneously (i.e. in solution). However, in order to prevent the production of mixtures of fusion proteins, it may in some embodiments be necessary to separate the fusion protein from other components in the reaction after each round of extension. Separation or purification can be achieved by any suitable means. For instance, one of the proteins in the fusion protein chain may comprise a purification tag or may be a binding protein (e.g. maltose binding protein) that would facilitate separation of the fusion protein from other components in the reaction, e.g. affinity chromatography. Additionally or alternatively, other purification/separation methods may be utilised, e.g. ion-exchange chromatography, size-exclusion chromatography, ultracentrifugation, spin-filtration, dialysis, dia-filtration etc.

Thus, in some embodiments, the method of the invention may comprise a step of separating or purifying the fusion protein after a step of isopeptide bond formation.

In a further embodiment, the invention provides a kit, particularly a kit for use in the methods and uses of the invention, i.e. in the production or synthesis of a fusion protein, wherein said kit comprises:

(a) a recombinant or synthetic polypeptide comprising a peptide linker as defined above; and (b) a recombinant or synthetic polypeptide comprising a peptide linker as defined that is capable of forming an isopeptide bond with the peptide linker in the polypeptide of (a); and/or (c) a nucleic acid molecule, particularly a vector, encoding a peptide linker as defined above; and/or (d) a nucleic acid molecule, particularly a vector, encoding a peptide linker that is capable of forming an isopeptide bond with the peptide linker encoded by the nucleic acid molecule of (b), optionally wherein the recombinant or synthetic polypeptide of (a) and/or (b) comprises a further peptide linker that is part of a pair of peptide linkers that are orthogonal to the peptide linkers in the polypeptides of (a) and (b).

The methods and uses of the invention may be defined as in vitro methods and uses, i.e. the in vitro method for the synthesis of a fusion protein.

It will be evident that the method of the invention is not limited to linking any specific proteins together to form a fusion protein. Thus, the method may utilize any protein or polypeptide as defined herein, i.e. any desired protein or polypeptide. In other words, the invention may utilise any protein or polypeptide that is desired to be included or incorporated into a fusion protein. Furthermore, the recombinant or synthetic polypeptide of the invention may comprise any protein linked to a peptide linker of the invention. The proteins may be derived or obtained from any suitable source. For instance, the proteins may be in vitro translated or purified from biological and clinical samples, e.g. any cell or tissue sample of an organism (eukaryotic, prokaryotic), or any body fluid or preparation derived therefrom, as well as samples such as cell cultures, cell preparations, cell lysates etc. Proteins may be derived or obtained, e.g. purified from environmental samples, e.g. soil and water samples or food samples are also included. The samples may be freshly prepared or they may be prior-treated in any convenient way e.g. for storage.

As noted above, in a preferred embodiment, the proteins to be incorporated in the fusion protein may be produced recombinantly and thus the nucleic acid molecules encoding said proteins may be derived or obtained from any suitable source, e.g. any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. In some embodiments, the proteins to be linked together in the fusion protein may be synthetic proteins.

As a representative example, the proteins to be joined in a fusion protein according to the invention may be enzymes, structural proteins, antibodies, antigens, prions, receptors, ligands, cytokines, chemokines, hormones and so on or any combination thereof.

In some embodiments, the recombinant or synthetic polypeptide of the invention and for use in the methods is not an isopeptide protein or a different isopeptide protein to the isopeptide protein from which the peptide linker is derived.

In some embodiments, the fusion protein comprises a repeated structure, e.g. the same protein may be linked together. Alternatively viewed, the fusion protein may contain two or more protein units of the same sequence. When the fusion protein contains two or more protein units of the same sequence, these protein units may be consecutive, e.g. separated only by the peptide linkers joining the protein units together, or they may be non-consecutive or non-sequential (e.g. separated by one or more proteins with a different sequence). In some preferred embodiments, the fusion protein comprises at least two proteins with different sequences, e.g. at least 2, 3, 4, 5, 6 proteins with different sequences. The proteins with different sequences may be arranged in any suitable order, depending on the purpose of the fusion protein.

In still further embodiments, the protein may consist of two or more peptide linkers as defined herein and optionally one or more spacers, e.g. peptide spacers, joining said peptide linkers. In this respect, the protein may be viewed as a non-functional protein or as a linker protein/peptide, as described above. In these embodiments, the other proteins in the fusion protein are different proteins or functional proteins, i.e. comprise sequences other than peptide linkers and spacers. Thus, in some embodiments the fusion protein comprises one or more proteins comprising an amino acid sequence as set forth in any one of SEQ ID NOs: 56-59 or with at least 70% sequence identity to an amino acid sequence as set forth in any one of SEQ ID NOs: 56-59, wherein said protein comprises at least two peptide linkers as defined above. For instance, a non-functional protein may be used as the second protein in a fusion protein, i.e. linking the first and third proteins, or the fourth protein in a fusion protein, i.e. linking the third and fifth proteins, and so on. In this representative example, the second and fourth proteins may be the same protein or different proteins. Thus, in some embodiments, the protein units in the fusion protein may comprise a linker protein alternately, e.g. function protein-linker protein-functional protein, or linker protein-functional protein-linker protein etc.

In some embodiments, the protein above is at least 75, 80, 85, 90, 95, 96, 97, 98, 99 or 100% identical to the sequence to which it is compared.

A "fusion protein" may be defined as a polymer comprising at least two protein units, e.g. 2, 3, 4, 5, 6, 7, 8, 9 or 10 or more protein units, such as 15, 20, 25 or 50 protein units, linked together by a covalent bond, preferably an isopeptide bond as defined herein. A protein unit may be defined as a molecule comprising at least 40 consecutive amino acids, preferably wherein the protein has a function in vivo, e.g. wherein the protein is capable of interacting specifically with one or more biological components, e.g. wherein the protein is active in vivo. Thus, a fusion protein may be viewed as a megastructure, macromolecule, megamolecule or polyprotein comprising at least two protein units, e.g. 2, 3, 4, 5, 6, 7, 8, 9 or 10 or more protein units, such as 15, 20, 25 or 50 protein units, linked together by a covalent bond, preferably an isopeptide bond as defined herein.

The terms "link", "linked" or "linking" in the context of the present invention with respect to two or more proteins in a fusion protein referred to joining or conjugating said proteins via a covalent bond, particularly an isopeptide bond which forms between the peptide linkers that are incorporated in said proteins (e.g. peptide linkers that form domains of said proteins).

Whilst the invention is described above in terms of pairs linkers that react together to form an isopeptide bond, each (cognate) pair of linkers alternatively may be viewed as a single peptide linker that is formed of two separate or separable parts (tags, tags and binding partners) that react to form an isopeptide bond (to link/conjugate said proteins). Thus, viewed from this perspective, the invention may be viewed as the use of two orthogonal peptide linkers for the production of a fusion protein, wherein each peptide linker comprises or consists of two separable parts that reacts to form an isopeptide bond and wherein each part of the linker is incorporated in (forms a domain of) the proteins to be linked (conjugated) together.

It will be evident that the methods and uses described herein and the fusion proteins obtained or obtainable from the methods described herein have a wide range of utilities. Alternatively viewed, the fusion proteins produced by the methods described herein may be employed in a variety of industries. For instance, the methods of the invention may be useful for producing fusion proteins for vaccination. In this respect, the methods may be useful for linking protein antigens into chains, either to be injected directly or used to decorate Viral-like particles (VLPS), since antigen multimerization gives greatly enhanced immune response.

The methods of the invention may be useful for producing fusion proteins with enhanced enzymatic properties, e.g. substrate channelling. In this respect, enzymes often come together to function in pathways inside cells and traditionally it has been difficult to connect multiple enzymes together outside cells (in vitro). Thus, the method of the invention could be used to enhance activity of multi-step enzyme pathways, which could be useful in a range of industrial conversions and for diagnostics.

The fusion proteins of the invention may also have improved properties with respect to their stability, i.e. the stability of the protein units in the fusion protein may be enhanced relative to their stability as independent proteins. In particular, fusion proteins may improve the thermostability of protein units. In this respect, enzymes are valuable tools in many processes but are unstable and hard to recover. Enzyme polymers have greater stability to temperature, pH and organic solvent and there is an increased desire to use enzyme polymers in industrial processes. However, prior to the present invention, enzyme polymer generation commonly used a glutaraldehyde non-specific reaction and this will damage or denature (i.e. reduce the activity of) many potentially useful enzymes. Site-specific linkage of proteins into chains (polymers) through isopeptide bonds according to the present invention is expected to enhance enzyme resilience, such as in diagnostics or enzymes added to animal feed. In particularly preferred embodiments, enzymes may be stabilized by circularization, as discussed above.

The methods of the invention will also find utility in the production of antibody polymers. In this respect, antibodies are one of the most important class of pharmaceuticals and are often used attached to surfaces. However, antigen mixing in a sample, and therefore capture of said antigen in said sample, are inefficient near surfaces. By extending chains of antibodies, it is anticipated that capture efficiency will be improved. This will be especially valuable in circulating tumour cell isolation, which at present is one of the most promising ways to enable early cancer diagnosis. Also antibodies of different specificities can be combined in any desired order.

In a still further embodiment, the methods of the invention may find utility in the production of drugs for activating cell signalling. In this respect, many of the most effective ways to activate cellular function are through protein ligands. However, in nature a protein ligand will usually not operate alone but with a specific combination of other signalling molecules. Thus, the methods of the invention allows the generation of tailored fusion proteins (i.e. protein teams), which could give optimal activation of cellular signalling. These fusion proteins (protein teams) might be applied for controlling cell survival, division, or differentiation.

In yet further embodiments, the peptide linkers of the invention, particularly pairs of linkers of the invention may find utility in the generation of hydrogels for growth of stem cells, preparation of biomaterials, antibody functionalization with dyes or enzymes and stabilizing enzymes by cyclization.

EXAMPLES

Figure 2:
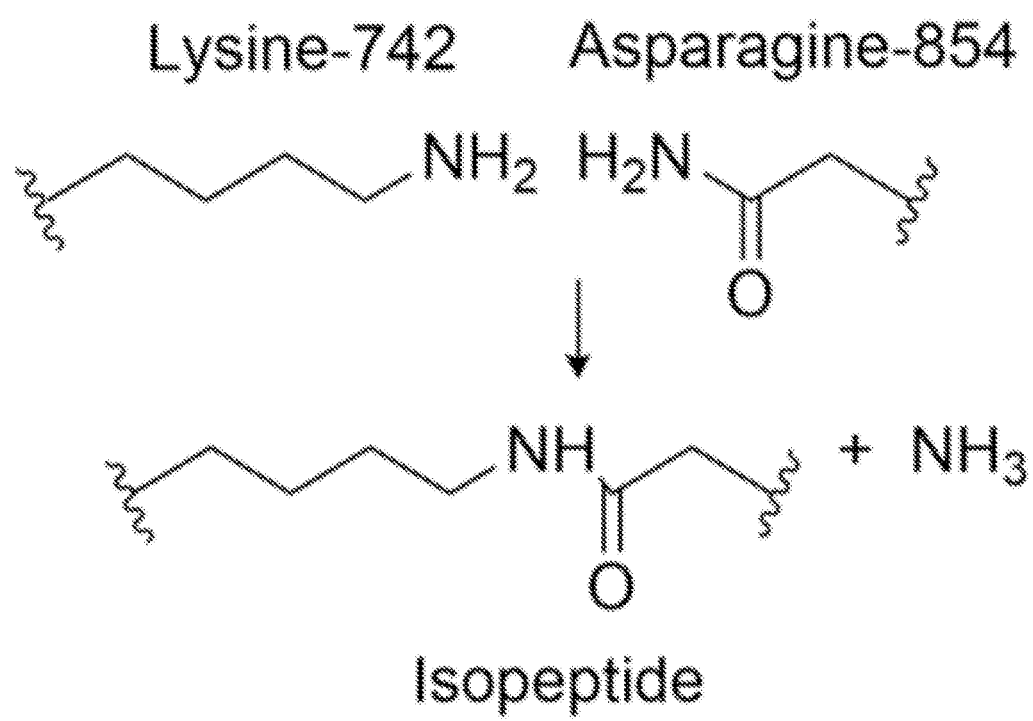
FIG. 2 shows a schematic of the isopeptide bond formation in the RrgA protein from which the SnoopTag and SnoopCatcher peptide linker pair is derived (numbering based on Protein Data Bank ID 2WW8).

Example 1—Design and Synthesis of Cognate Pairs of Peptide Linkers that Form Spontaneous Isopeptide Bonds RrgA (SEQ ID NO: 21) is an adhesin from *Streptococcus pneumoniae*, a Gram-positive bacterium which can cause septicaemia, pneumonia and meningitis in humans. A spontaneous isopeptide bond forms in the D4 immunoglobulin-like domain of RrgA between residues Lys742 and Asn854 (FIG. 2). The inventor split the D4 domain into a pair of peptide linkers termed SnoopTag (residues 734-748, SEQ ID NO: 1) and a protein which we named SnoopCatcher (residues 749-860, SEQ ID NO: 2).

However, the inventors founds that it was necessary introduce two mutations in to the SnoopCatcher peptide linker in order to form a stable pair of peptide linkers for use in the invention. In this respect, the inventor introduced the G842T mutation in SnoopCatcher to stabilize a β-strand and the D848G to stabilize a hairpin turn close to the reaction site.

Figure 3:
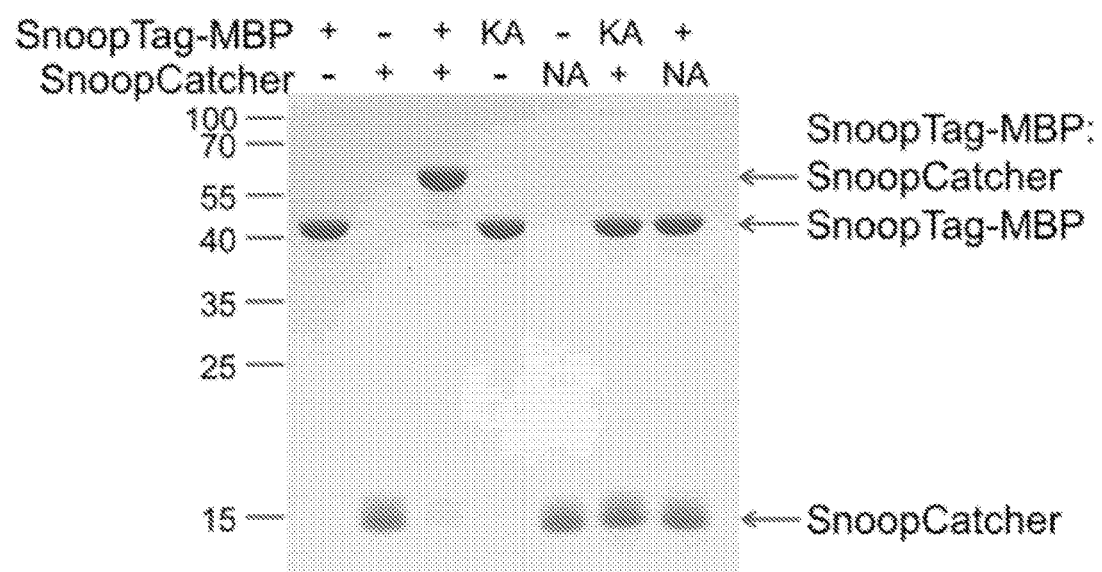
FIG. 3 shows a picture of an SDS-PAGE gel with Coomassie staining characterising the SnoopTag-MBP reaction with SnoopCatcher alongside controls with alanine mutation of SnoopTag's reactive Lys (KA) or SnoopCatcher's reactive Asn (NA).

The SnoopTag peptide was expressed as a recombinant polypeptide fused to the Maltose Binding Protein (MBP) and a His-Tag (SEQ ID NO: 50). SnoopCatcher was expressed as a recombinant polypeptide fused to a His-Tag (SEQ ID NO: 39). SnoopTag-MBP and SnoopCatcher were expressed efficiently as soluble proteins in the cytosol of *Escherichia coli* and purified by Ni-NTA affinity chromatography. SnoopTag-MBP and SnoopCatcher, simply upon mixing, formed a complex stable to boiling in SDS (FIG. 3). Mutations in the putative reactive Lys742 of SnoopTag (SnoopTag KA-MBP) and the putative reactive Asn854 of SnoopCatcher (SnoopCatcher NA) abolished reaction (FIG. 3). Electrospray ionization mass spectrometry supported the loss of $NH_3$ from isopeptide bond formation between Snoop-Catcher and synthetic SnoopTag peptide; acetylated and gluconylated side-products common for *E. coli* overexpression were also observed.

Figure 4:
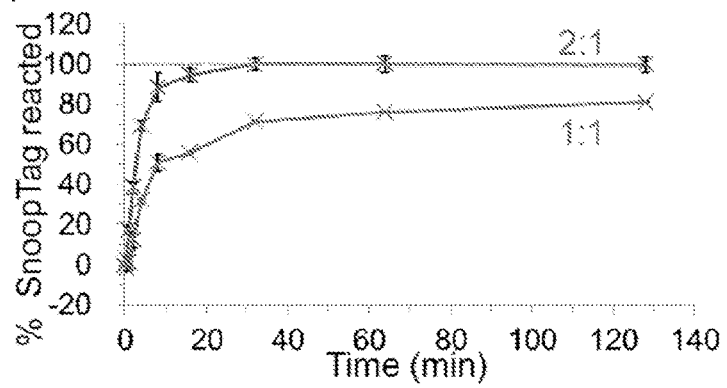
FIG. 4 shows (A) a graph depicting the time-course of SnoopTag reaction with 1:1 or 2:1 ratio of SnoopCatcher to SnoopTag-MBP; (B) a picture of an SDS-PAGE gel with Coomassie staining characterising the SnoopTag-MBP reaction with SnoopCatcher at a 2:1 ratio of SnoopCatcher to SnoopTag-MBP; (C) a graph depicting the time-course of SnoopTag reaction with 1:1, 2:1 or 4:1 ratio of SnoopCatcher to SnoopTag-MBP; and (D) a picture of an SDS-PAGE gel with Coomassie staining characterising the SnoopTag-MBP reaction with SnoopCatcher at a 4:1 ratio of SnoopCatcher to SnoopTag-MBP.
Figure 4:
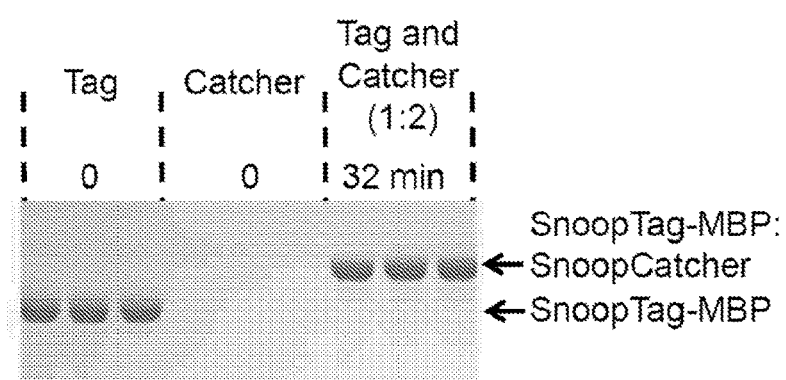
Figure 4:
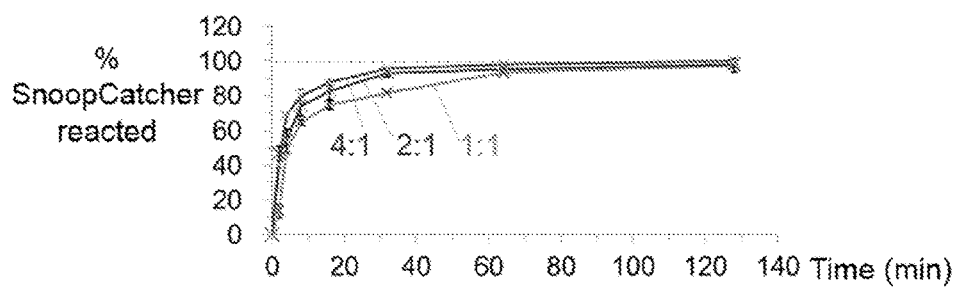
Figure 4:
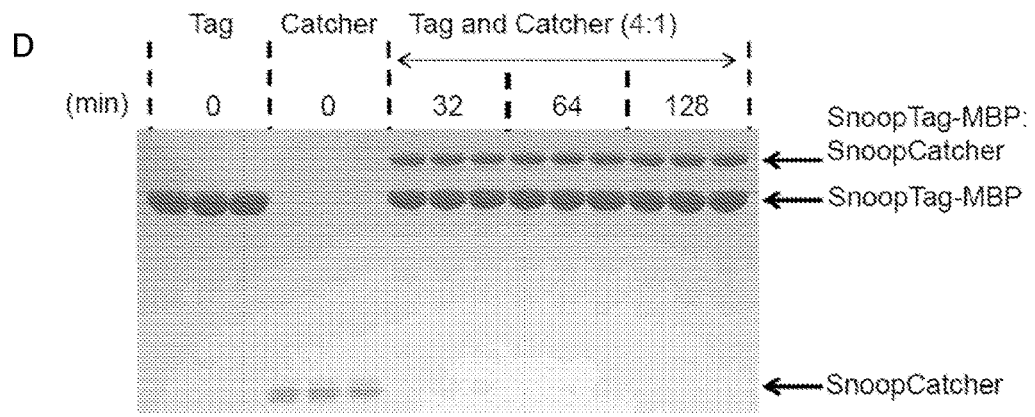

With 1:1 SnoopCatcher to SnoopTag-MBP reaction proceeded to ~80% yield. However, with a two-fold excess of SnoopCatcher, SnoopTag-MBP reacted quantitatively (FIG. 4, parts A and B). Similarly with an excess of SnoopTag-MBP, SnoopCatcher was ~100% consumed (FIG. 4, parts C and D).

Figure 5:
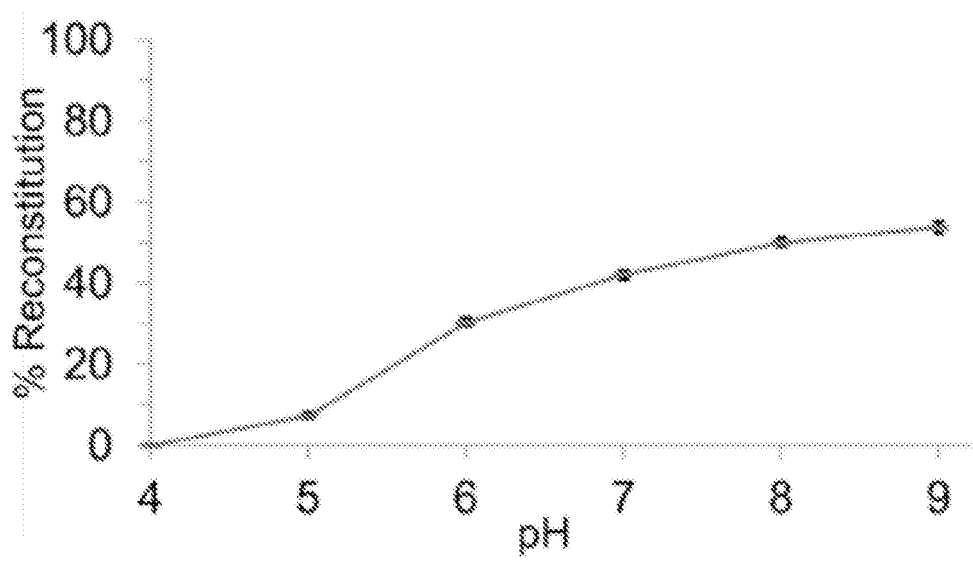
FIG. 5 shows (A) a bar chart depicting the pH-dependence of the isopeptide bond formation between SnoopTag-MBP and SnoopCatcher; and (B) a chart depicting the temperature-dependence of the isopeptide bond formation between SnoopTag-MBP and SnoopCatcher.
Figure 5:
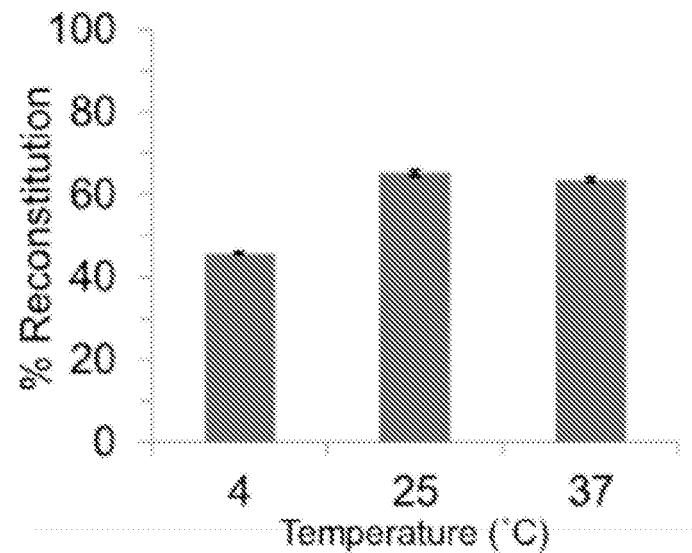
Figure 6:
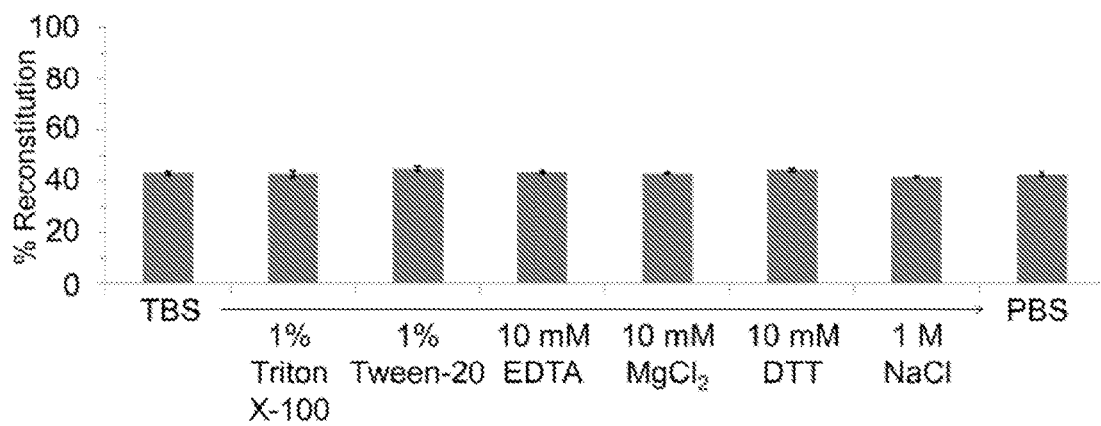
FIG. 6 shows (A) a bar chart depicting the dependence of the isopeptide bond formation between SnoopTag-MBP and SnoopCatcher on salt, reducing agent and detergent; and (B)
Figure 6:
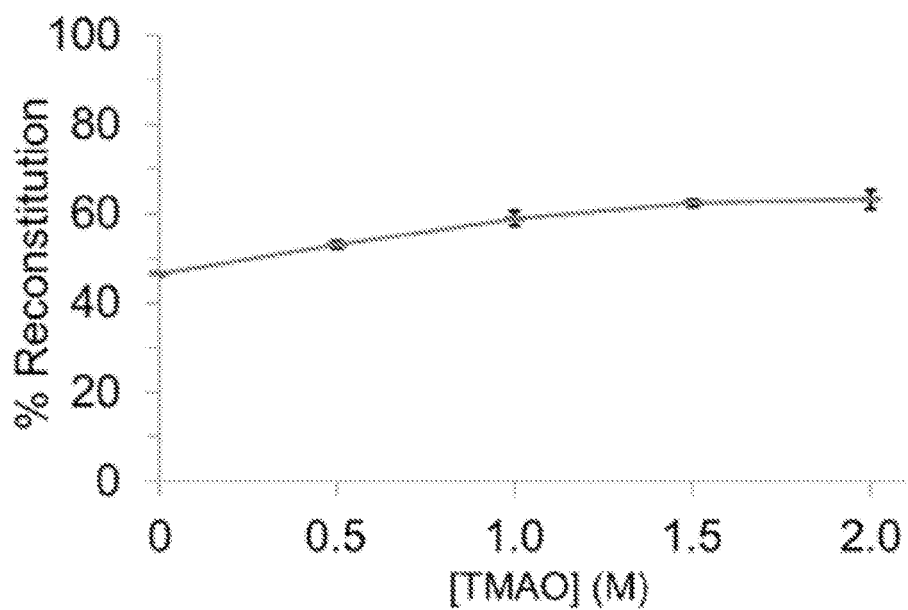

The inventors further established that reaction proceeded efficiently from pH 6-9, but was slowed at pH 5 (FIG. 5, part A). Reaction was fastest at room temperature but also occurred at 4° C. and 37° C. (FIG. 5, part B). Cysteine is absent from SnoopTag and SnoopCatcher so, as expected, the reaction was insensitive to dithiothreitol (DTT). No specific buffer component was required, with reaction in PBS as well as in the presence of the detergents Triton X-100 and Tween 20, or high salt (1 M NaCl) (FIG. 6, part A). The chemical chaperone trimethylamine N-oxide (TMAO) gave a modest enhancement (FIG. 6, part B).

Spontaneous hydrolysis of an amide bond normally takes years under neutral conditions but we tested if hydrolysis was accelerated in this particular protein environment. We looked for cleavage of the SnoopTag-MBP/SnoopCatcher interaction, by competing with excess of an alternative SnoopTag-linked protein or with ammonia but we did not observe reversibility.

A further pair of peptide linkers was developed from the RrgA protein by splitting the D4 immunoglobulin-like domain in a different direction to the SnoopTag/Snoop-Catcher pair of peptide linkers. This pair of peptide linkers was termed RrgATag (SEQ ID NO: 9) and RrgACatcher (SEQ ID NO: 10). A pair of peptide linkers was also developed based on the PsCs protein (SEQ ID NO: 31), termed PsCsTag (SEQ ID NO: 5) and PsCsCatcher (SEQ ID NO: 6).

Each pair of peptide linkers is capable of spontaneously forming an isopeptide bond under a variety of conditions akin to the SnoopTag/SnoopCatcher pair discussed above.

Example 2—Investigating the Cross-Reactivity of Pairs of Peptide Linkers

A peptide tag and binding partner, SpyTag and Spy-Catcher (SEQ ID NOs: 13 and 14), that react spontaneously to form an isopeptide bond have been developed previously (WO2011/098772).

SnoopTag has a reactive Lys, whereas SpyTag has a reactive Asp, so the inventor hypothesized that the SnoopTag/SnoopCatcher and SpyTag/SpyCatcher pairs would be fully orthogonal, i.e. would not show cross-reactivity. Upon mixing the peptide linkers in various combinations, it was found that each cognate pair of peptide linkers reacted efficiently, but found no trace of cross-reaction between pairs was found, even after overnight incubation (FIG. 7). This result confirmed that the SnoopTag/SnoopCatcher pair is orthogonal to SpyTag/Spy-Catcher.

The inventor also tested the PsCsTag/PsCsCatcher pair and RrgATag/RrgACatcher pair for cross-reactivity with the SnoopTag/SnoopCatcher and SpyTag/SpyCatcher pairs. As shown in FIG. 8, parts A and B, no significant cross-reactivity was found between the "PsCs" pair and the "Spy" pair or "Snoop" pair. Similarly, no significant cross-reactivity was found between the "RrgA" pair and the "Spy" pair or "Snoop" pair. Thus, each pair of peptide linkers is orthogonal to the other pairs of peptide linkers.

Example 3—Synthesis of Fusion Proteins Using Two Orthogonal Pairs of Peptide Linkers The inventors used the "Spy" and "Snoop" pairs of peptide linkers to demonstrate that such orthogonal pairs of peptide linkers can be used successfully to synthesise fusion proteins.

The interaction of *E. coli* MBP with amylose resin is widely used in affinity purification: MBP-fusions typically fold and express well and show low non-specific resin binding. MBP shows selective mild elution using maltose, avoiding need for protease removal. The affinity of wild-type MBP for maltose is 1.2 µM, which is practical for protein purification but insufficient for multiple rounds of washing and chain extension in fusion protein synthesis. Therefore, the inventors developed a mutated MBP to improve its maltose-binding stability. Firstly, the inventors modified the polypeptide sequence by introducing mutations A312V and I317V and deleting residues 172, 173, 175 and 176). Secondly, the MBP mutant (SEQ ID NO: 70) was tandemly-linked to generate MBPx (Hexahistidine-MBPmt-linker-MBPmt).

For initial chain building, the inventors incorporated affibodies, a non-immunoglobulin scaffold expressed efficiently in the *E. coli* cytosol. The affibody to HER2 was linked at its N-terminus with SnoopTag and at its C-terminus with SpyTag (SnoopTag-Affi-SpyTag, SEQ ID NO: 72). Affibody units were bridged using SpyCatcher connected through a helical spacer to SnoopCatcher (SpyCatcher-SnoopCatcher (SEQ ID NO: 56), which also expressed efficiently as a soluble protein in *E. coli*) (FIG. 1). Since each linkage is covalent, chain synthesis could be followed by adding maltose to elute from the resin and then boiling the supernatant before SDS-PAGE with Coomassie staining to follow the extension of the fusion protein (FIG. 9, part A). MBPx-SpyCatcher (bound to amylose resin) reacted quantitatively with SnoopTag-Affi-SpyTag (FIG. 9, part A, lane 5). This construct then reacted quantitatively with Spy-Catcher-SnoopCatcher (FIG. 9, part A, lane 6). Sequential addition of SnoopTag-Affi-SpyTag and SpyCatcher-Snoop-Catcher enabled efficient chain growth, extending to a product 10 units long (a decamer, FIG. 9, part A, lane 13).

To demonstrate solid-phase extension with a different kind of solid-phase attachment, a modified SpyCatcher protein was generated, AviTag-SpyCatcher, to allow site-specific N-terminal biotinylation. After linking biotinylated SpyCatcher to streptavidin-coated beads, fusion protein chains were assembled to the length of a decamer in the same way and eluted with free biotin (FIG. 9, part B).

To validate the assembled decamer, electrospray ionization mass spectrometry was performed, showing good correspondence between observed and expected masses (FIG. 10, part A). Whilst mass spectrometry gives a good indication of identity, SDS-PAGE is much better for assessing purity, because lower molecular weight side-products ionize more efficiently. Affibodies are usually monomeric, showing little self-association, thus to analyze whether the decamer formed aggregates size-exclusion chromatography (SEC) was performed. SEC gave one major peak, consistent with the expected monomeric mass of the decamer calibrated with globular protein standards, indicating that there was minimal decamer self-association under these conditions (FIG. 10, part B).

To assess thermostability, the decamer was heated briefly at a range of temperatures and remained largely soluble even at 70° C. (FIG. 11, part A). Decamer integrity to storage was also tested and little degradation and little loss of solubility was observed after 1 or 4 days (FIG. 11, part B).

Expanding from the initial incorporation of AffiHER2 into the chains, it was shown that other protein units could be incorporated efficiently using orthogonal isopeptide bond formation (FIG. 12). In this respect, fluorescent protein fusion protein chains were generated (FIG. 12, part A). Bottle-brush fusion protein polymers were also produced, by joining a tandemly-linked affibody against HER2 with both the tags at the N-terminus (SnoopTag-SpyTag-Affi-Affi-Affi) (FIG. 12, part B).

In summary, the inventor has developed a modular approach to synthesis of fusion proteins, through spontaneous isopeptide bond formation between peptide linkers. The fusion proteins generated according to the method of the invention are linked through irreversible amide bonds, so are stable over time (if protected from proteases) and allow easy analysis by SDS-PAGE. The initiation, extension and release steps use mild conditions, independent of redox state, so should be applicable to a wide range of proteins. With only a single way for the chain to grow, products are molecularly defined, favouring reproducibility and precise tuning of function. Also, subunits do not need to be connected in an N- to C-orientation, as shown with the bottle-brush polymer architectures described above. No chemical modification of the module is required, avoiding time-consuming and hard-to-control bioconjugation steps, so the method is accessible to any laboratory able to express recombinant proteins. Spontaneous isopeptide bond formation has the advantage of a simple reaction pathway between two functional groups having low intrinsic reactivity—an amine with a carboxylic acid or a carboxamide—so there is little side-reaction.

Whilst this example demonstrates fusion protein synthesis using the "Spy" and "Snoop" pairs of peptide linkers, it will be evident that any orthogonal pairs of peptide linkers according to the invention may be utilised in the methods of the invention and, as discussed above, using more than two orthogonal pairs of peptide linkers may be particularly advantageous for synthesizing fusion proteins with complex structures, e.g. branched or circular structures.

Example 4—Design and Synthesis of Improved Cognate Pair of Peptide Linkers Based on the RrgA Protein The RrgATag described in Example 1 was subject to a variety of modifications with the objective of producing a pair of peptide linkers with improved activity relative to the RrgATag/RrgACatcher peptide linker pair.

The inventor synthesized a mutant RrgATag peptide linker comprising a substitution at position 11—Aspartic acid to Glycine (D11G)—called RrgATag2.0 (see Table 2 below). RrgATag2.0 (SEQ ID NO: 111) and RrgATag (SEQ ID NO: 9) were expressed as fusion proteins linked to maltose binding protein (MBP) and their reactivity with RrgACatcher was compared. The reactions were performed for 6 hours in phosphate buffered saline (PBS) at pH 7.4 and room temperature. 10 µM of each protein was used in each reaction.

FIG. 14 shows that RrgATag2.0 has greatly increased reactivity with RrgACatcher when compared with RrgATag.

The inventor synthesized a further eight peptide linkers comprising various mutations relative to the RrgATag (SEQ ID NO: 9), including extensions, truncations, substitutions and combinations thereof. Table 2 shows the sequences of the mutant RrgATag peptide linkers, wherein substitutions and extensions are underlined.

TABLE 2

| Peptide name (SEQ ID NO:) | Sequence | Modification relative to RrgATag (SEQ ID NO: 9) |
|---|---|---|
| RrgATag (SEQ ID NO: 9) | DIPATYEFTNDKHYITNEP | — |
| RrgATag2 (SEQ ID NO: 109) | DIPATYEFTN<u>G</u>KHYITNEP<u>IPPK</u> | D11G (substitution) 4 amino acid C-terminal extension |
| RrgATag2.0 (SEQ ID NO: 111) | DIPATYEFTN<u>G</u>KHYITNEP | D11G (substitution) |
| RrgATag2.1 (SEQ ID NO: 113) | DIPATYEFTN<u>G</u>KHYITNE | D11G (substitution) 1 amino acid C-terminal deletion |
| RrgATag2.2 (SEQ ID NO: 115) | DIPATYEFTN<u>G</u>KHYITN | D11G (substitution) 2 amino acid C-terminal deletion |

TABLE 2-continued

| Peptide name (SEQ ID NO:) | Sequence | Modification relative to RrgATag (SEQ ID NO: 9) |
|---|---|---|
| RrgATag2.3 (SEQ ID NO: 117) | ATYEFTNGKHYITNEP | D11G (substitution) 3 amino acid N-terminal deletion |
| RrgATag2.4 (SEQ ID NO: 119) | KHYITNEP | 11 amino acid N-terminal deletion |
| RrgATag2.5 (SEQ ID NO: 121) | GKHYITNEP | D11G (substitution) 10 amino acid N-terminal deletion |
| RrgATag2.6 (SEQ ID NO: 123) | NGKHYITNEP | D11G (substitution) 9 amino acid N-terminal deletion |
| RrgATag2.7 (SEQ ID NO: 125) | IVPQDIPATYEFTNGKHYITNEP | D11G (substitution) 4 amino acid N-terminal extension |

The mutated RrgATag peptide linkers were expressed as fusion proteins linked to a SUMO (small ubiquitin modifier) protein and the fusion proteins were tested for reactivity with RrgACatcher (SEQ ID NO: 10). The reactions were performed for 30 minutes in phosphate buffered saline (PBS) at pH 7.4 and room temperature. 10 µM of each protein was used in each reaction. FIG. 15 shows that only four of the modified RrgATag peptide linkers showed observable reactivity with RrgACatcher RrgATag 2.0, RrgATag2.3, RrgATag2 and RrgATag2.7. However, RrgATag2 showed a significant increase in activity relative to RrgATag2.0, which as discussed above, has increased activity relative to RrgATag. Thus RrgATag2 has significantly improved reactivity with RrgACatcher in comparison to RrgATag.

The speed of reaction between RrgATag2 (in the form a fusion protein with SUMO) and RrgACatcher is shown in FIG. 16 and indicates that an excess of RrgATag2 increases the speed of reaction. However, the reaction neared completion, i.e. 100% consumption of RrgACatcher, at all concentrations of RrgATag2.

Whilst not wishing to be bound by theory, it is hypothesised that the significantly improved activity of RrgATag2 is a result of the combination of modifications/mutations relative to RrgATag. In this respect, the C-terminal extension, which is based on the native RrgA sequence, is thought to form favourable interactions with the RrgACatcher peptide linker. Furthermore, it is hypothesised that the D to G mutation (i.e. the reduction in the size of the side-chain) in the middle of the RrgATag2 peptide linker stabilises the hairpin turn in the peptide (as seen in the crystal structure to be present in the full length domain).

Example 5—Investigating the Cross-Reactivity of the Improved RrgATag2 Peptide Linker The RrgATag2/RrgACatcher peptide linker pair was tested for cross-reactivity against the SnoopTag/SnoopCatcher and SpyTag/SpyCatcher peptide linker pairs, as described in Example 3 above. The RrgATag2 peptide linker was expressed as a fusion protein linked to SUMO, as described in Example 4.

FIG. 17 shows that no significant cross-reactivity was found between the RrgACatcher peptide linker and the SpyTag or SnoopTag peptide linkers. FIG. 18 shows that no significant cross-reactivity was found between the RrgATag2 peptide linker and the SpyCatcher or SnoopCatcher peptide linkers. Thus, each pair of peptide linkers is orthogonal to the other pairs of peptide linkers.

Materials and Methods

Cloning

KOD Hot Start DNA Polymerase (Roche) was used to perform all PCR and site-directed mutagenesis. Gibson Assembly® Master Mix (NEB) was used according to the manufacturer's instructions. Constructs were initially cloned into chemically competent E. coli DH5α (Life Technologies).

pET28a SpyTag-MBP (Addgene plasmid ID 35050), Glutathione-S-Transferase-BirA and pDEST14-SpyCatcher (GenBank JQ478411, Addgene plasmid ID 35044) have been described in B. Zakeri et al., 2012 (Proc Natl Acad Sci USA 109, E690-697).

pET28a SnoopCatcher was generated by DNAWorks primer-mediated assembly from residues 749-860 of Streptococcus pneumoniae adhesin RrgA (numbering based on Protein Data Bank ID 2WW8), digested with HindIII and NdeI and subcloned into pET28a. To optimize reaction with SnoopTag, the G842T mutation was made in this construct by QuikChange with 5'-GTGCCGCAGGATATTCCGGC-TACATATGAATTTACCAACG (SEQ ID NO: 73), and the D848G mutation with 5'-GCTACATATGAATTTAC-CAACGGTAAACATTATATCACCAATGAACC (SEQ ID NO: 74) and their reverse complements. SnoopCatcher is 132 residues long (assuming fMet cleavage) and has an N-terminal thrombin cleavage site and His$_6$ tag. pET28a SnoopCatcher NA was produced from pET28a SnoopCatcher by QuikChange of N854 to A using the forward primer 5'-ACATTATATCACCGCTGAACCGATAC-CGCCG (SEQ ID NO: 75) and its reverse complement.

pET28a SnoopTag-MBP was generated in two steps. First the reactive peptide based on the N-terminal β-strand of RrgA's D4 domain was cloned (residues 734-748) into pET28a-SpyTag-MBP by site-directed, ligase-independent mutagenesis (SLIM) PCR (Chiu et al., 2004) using 5'-GG-TAGTGGTGAAAGTGGTAAAATCGAAGAAG (SEQ ID NO: 76), 5'-AAACTGGGCGATATTGAATTTATTAAAGT-GAACAAAAACGATAAAGGTAGTGGT GAAAGTGG-TAAAATCGAAGAAG (SEQ ID NO: 77), 5'-TC-CCATATGGCTGCCGCGCG (SEQ ID NO: 78) and 5'-TTTATCGTTTTTGTTCACTTTTAATAAT-TCAATATCGCCCAGTTTTCCCATATGG CTGC-CGCGCG (SEQ ID NO: 79). The 3 C-terminal residues of the peptide were removed using QuikChange with 5'-GAATTTATTAAAGTGAACAAAGGTAGTGGT-GAAAGTGGTAAAATCG (SEQ ID NO: 80) and its reverse complement. pET28a SnoopTag KA-MBP, an unreactive version of SnoopTag, was generated by QuikChange of K742 to A on pET28a SnoopTag-MBP using 5'-GGGCGA-TATTGAATTTATTGCAGTGAACAAAGGTAGTGG (SEQ ID NO: 81) and its reverse complement.

pET28a MBP-SpyCatcher was generated by fusing Spy-Catcher with a Gly/Ser spacer at the C-terminus of MBP, through overlap extension PCR. SpyCatcher was amplified from pDEST14-SpyCatcher using the forward primer 5'-GT-TCGGGCGGTAGTGGTGCCATGGTTGATACCT-TATCAGGTTTATCAAGG CAAG (SEQ ID NO: 82) and the reverse primer 5'-TACTAAGCTTCTATTAAATAT-GAGCGTCACCTTTAGTTGCTTTGCCATTTACAG (SEQ ID NO: 83). The forward primer 5'-ATCT-CATATGGGCAGCAGCCATCATCATCATCATCAC (SEQ ID NO: 84) and the reverse primer 5'-GTATCAAC-CATGGCACCACTACCGCCCGAACCCGAGCTC-GAATTAGTCTGCG (SEQ ID NO: 85) were used to amplify MBP from pET28a SpyTag-MBP. The two resulting PCR products were mixed and amplified again using the SpyCatcher forward primer and the MBP reverse primer, digested with NdeI and HindIII, and subcloned into pET21. To increase the affinity of MBP-SpyCatcher for amylose we first made the A312V and I317V mutations in MBP by QuikChange using the forward primer 5'-GTCTTACGAG-GAAGAGTTGGTGAAAGATCCACGTGTGGCCGC-CACTATGGAA AACGC (SEQ ID NO: 86) and its reverse complement. Residues 172, 173, 175 and 176 were deleted from MBP using QuikChange with 5'-GGGTTATGCGT-TCAAGTATGGCGACATTAAAGACGTGGGCG (SEQ ID NO: 87) and its reverse complement. We then shortened SpyCatcher's N-terminus by QuikChange using 5'-CAC-CATCACCATCACGATTACGATAGTGCTACCCATAT-TAAATTCTC (SEQ ID NO: 88) and its reverse complement. To decrease even further the dissociation from amylose resin, tandem links of this mutant MBP were generated to give MBPx-SpyCatcher (N-terminal His$_6$ tag-MBPmt-spacer-MBPmt-spacer-SpyCatcher). MBPx was amplified and fused to MBPx-SpyCatcher via Gibson assembly using the forward primer 5-GGCGGATCCG-GAGGTGGATCCGGAAAGATAGAGGAGGG-TAAACTGGTAATCT GG (SEQ ID NO: 89), the reverse primer 5-CCTATAGTGAGTCGTATTAATTTCG (SEQ ID NO: 90), the forward primer 5-CGAAATTAATACGACT-CACTATAGG (SEQ ID NO: 91) and the reverse primer 5-TCCGGATCCACCTCCGGATCCGCCGGAACTA-GAATTCGTCTGCGCGTCTTTCA GG (SEQ ID NO: 92).

pET28a SpyCatcher-SnoopCatcher was produced in steps. Initially SpyCatcher was fused with a Gly/Ser spacer at the N-terminus of SnoopCatcher, then the Gly/Ser spacer was replaced with an a-helical spacer (sequence PANLKA-LEAQKQKEQRQAAEELANAKKLKEQLEK, SEQ ID NO: 93). The forward primer 5'-CTTTAAGAAGGAGA-TATACATATGTCGTACTACCATCACCATC (SEQ ID NO: 94) and the reverse primer 5'-CCGCTGCTTCCG-GATCCAATATGAGCGTCACCTTTAGTTG (SEQ ID NO: 95) were used to amplify the SpyCatcher portion from pDEST14-SpyCatcher. The SnoopCatcher part was cloned using the forward primer 5'-CATATTGGATCCGGAAGCA-GCGGCCTGGTGCCGCGCGGATCCCATATGAAGC CGCTGC (SEQ ID NO: 96) and the reverse primer 5'-GTG-GTGGTGGTGGTGCTCGAGTTATTATTTCGGCGG-TATCGGTTC (SEQ ID NO: 97) from pET28a Snoop-Catcher. Following SpyCatcher and SnoopCatcher fusion, the Gly/Ser spacer was replaced with stable a-helical linker using the forward primer 5'-CTAAAGGTGACGCTCATAT-TGGATCCCCCGCCAACCTGAAGGCCCTGGAGGC CCAGAAGCAGAAGGAGCAGAGACAGGCCGC-CGAGGAGC (SEQ ID NO: 98) and the reverse primer 5'-CACGGCACCACGCAGCGGCTTCATATGGGATC-CCTTCTCCAGCTGCTCCTTCA GCTTCTTGGCGTTG-GCCAGCTCCTCGGCGGCCTGTC (SEQ ID NO: 99). 35 residues were deleted from SpyCatcher's N-terminus via QuikChange using the forward primer 5'-CACCATCAC-CATCACGATTACGATAGTGCTACCCATATTAAAT-TCTC (SEQ ID NO: 100) and its reverse complement.

pET28a SnoopTag-Affi-SpyTag (N-terminal His$_d$ tag-SnoopTag-spacer-Affibody against HER2-spacer-SpyTag) was generated by Gibson assembly using the forward primer 5'-GTGAACAAAGGCAGTGGTGAGTCGGGATCCG-GAGCTAGCATGACTGGTGG (SEQ ID NO: 101) and the reverse 5' CATCACGATGTGGGCACCGGAACCTTC-CCCGGATCCCTCGAGGCCTTTCGG (SEQ ID NO: 102) from pET28a-KTag-AffiHer2-SpyTag.

pET28a SnoopTag-AffiTaq-SpyTag, an affibody against Taq DNA polymerase was generated by inverse PCR from pET28a SnoopTag-AffiHer2-SpyTag using 5'-CTAC-CCAACCTAAACGGGGTACAAGTAAAGGCTTTCATA-GACTCGCTAAGGCA TGACCCAAGCCAAAGCGC (SEQ ID NO: 103) and 5'-GTTGAATATCTCCCAAG-TAGCCCACCCTAGCTCCTTGTTGAACTTGTTGTC-TAC TTCTTTGTTGAATTTGTTGTCCACGCC (SEQ ID NO: 104).

pET28a SnoopTag-mEGFP-SpyTag was cloned by substituting mEGFP at the BamHI sites in pET28a SnoopTag-Affi-SpyTag and by PCR to extend the spacer. pET28a SnoopTag-SpyTag-Affi3 was generated by PCR assembly of tandem copies of AffiHER2 linked by Gly/Ser spacers.

AviTag-SpyCatcher, containing a peptide tag for site-specific biotinylation at the N-terminus was cloned by SLIM PCR from pDEST14-SpyCatcher using 5'-GATTACGA-CATCCCAACGACCGAAAACCTG (SEQ ID NO: 105), 5'-GCCTGAACGATATTTTGAAGCGCAGAAAATT-GAATGGCATGAAGGCGATTAC GACATCCCAAC-GACCGAAAACCTG (SEQ ID NO: 106), 5'-GTGATGGT-GATGGTGATGGTAGTACGACATATG (SEQ ID NO: 107) and 5'-TGCCATTCAATTTTCTGCGCT-TCAAAATATCGTTCAGGCCGCTGCCGTGATG GTGATGGTGATGGTAGTACGACATATG (SEQ ID NO: 108).

All mutations and constructs were verified by sequencing.

Protein Expression and Purification

Proteins were expressed in *E. coli* BL21 DE3 RIPL (Agilent). Colonies were grown up overnight at 37° C. in LB containing 0.5 mg/mL kanamycin for pET28a vectors and 0.1 mg/mL ampicillin for pET21. The overnight cultures were diluted 1:100 in LB containing 0.8% glucose with the appropriate antibiotic and grown at 37° C., 200 rpm to $OD_{600}$ 0.5-0.6 and induced with 0.4 mM IPTG at 30° C., 200 rpm for 4 h. Proteins were purified by standard methods on Ni-NTA (Qiagen) and dialyzed thrice with TBS (50 mM Tris HCl pH 8.0 and 50 mM NaCl).

For MBPx-SpyCatcher's purification, after elution from Ni-NTA, the buffer was exchanged by dialysis into 20 mM Tris HCl pH 8.0 at 4° C., loaded onto quaternary high performance (Q-HP) resin (GE Healthcare) and eluted by 10 column volumes (i.e. 10 mL) linear gradient of 0-0.15 M NaCl with a flow rate of 1 mL/min. An extra elution step was performed with a linear gradient of 0.15-0.35 M NaCl at the flow rate of 1.5 mL/min and collecting 0.5 mL fractions. Collected fractions were dialyzed into TBS, concentrated using a Vivaspin centrifugal concentrator 5 kDa cutoff (GE Healthcare) and stored at −80° C.

SnoopTag-Affi-SpyTag was dialyzed in 20 mM 2-(N-morpholino)ethanesulfonic acid (MES) pH 5.8 at 4° C. and loaded onto sulfopropyl high performance (SP-HP) resin (GE Healthcare). Protein was eluted by applying a linear gradient of 0.2-0.5 M NaCl and collecting 1 mL fractions. The eluted fractions were concentrated to 1-2 mg/mL using a Vivaspin centrifugal concentrator 5 kDa cutoff (GE Healthcare), dialyzed into TBS pH 8.0 and stored at −80° C.

For SpyCatcher-SnoopCatcher's purification, after elution from Ni-NTA, the buffer was exchanged by dialysis into 20 mM Tris HCl pH 8.0 at 4° C., loaded onto quaternary high performance (Q-HP) resin and eluted with a linear gradient of 0.2-0.5 M NaCl. Collected fractions were dialyzed into TBS, concentrated using a Vivaspin centrifugal concentrator 5 kDa cut-off and stored at −80° C.

Purified AviTag-SpyCatcher was biotinylated in PBS pH 7.4 containing 5 mM $MgCl_2$, 1 mM ATP, 380 µM D-biotin and 7 µM GST-BirA for 1 hr at 25° C. After 1 hr incubation, further GST-BirA was added to give a final concentration of 14 µM and the reaction was incubated for another hour at 25° C. GST-BirA was removed by incubating the reaction mixture with 50 µL of slurry Hi-Cap Glutathione matrix (Qiagen) at 25° C., with end-over-end rotation for 30 min. Resin was spun down at 4,000 g for 1 min. The supernatant was collected and dialyzed overnight at 4° C. into PBS. To confirm complete biotinylation, a streptavidin gel-shift assay was performed as described.

SDS-PAGE

SDS-PAGE was performed on the indicated percentage polyacrylamide gel using an XCell SureLock gel container (Life Technologies) at 200 V. Gels were stained with Instant Blue Coomassie stain (Triple Red Ltd.) and bands were densitometrically analyzed using a Gel Doc XR imager and Image Lab 3.0 software (Bio-Rad). All running buffers were Tris-glycine, except for FIG. 9, part A which was Tris-acetate to improve resolution of high M. products.

Isopeptide Bond Reconstitution

To assess the formation of a covalent bond between SnoopTag and SnoopCatcher, proteins were mixed each at 10 µM final concentration in TBS pH 8.0 containing 1.5 M trimethylamine N-oxide (TMAO; Sigma-Aldrich). TMAO acts as a chemical chaperone. Reactions were stopped by adding 6×SDS loading buffer (0.23 M Tris-HCl, pH 6.8, 24% v/v glycerol, 120 µM bromophenol blue, 0.23 M SDS). Samples were subsequently heated using a Bio-Rad C1000 thermal cycler at 95° C. for 5 min, before SDS-PAGE on 16% polyacrylamide gels.

To test orthogonality, 10 µM SnoopTag-MBP and 10 µM SnoopCatcher or SpyCatcher were incubated for 1 hr at 25° C. in TBS pH 8.0, before SDS-PAGE. Similarly 10 µM SpyTag-MBP and 10 µM SnoopCatcher or SpyCatcher were incubated as above.

For the other peptide linker pairs, 10 µM RrgATag-MBP or 10 µM PsCsTag-MBP and 10 µM SnoopCatcher, SpyCatcher, SnoopTag-MBP or SpyTag-MBP were incubated for 24 hr at 25° C. in PBS pH 7.4, before SDS-PAGE.

To evaluate the pH-dependence, each protein was mixed at 10 µM in succinate-phosphate-glycine buffer (12.5 mM succinic acid, 43.75 mM $NaH_2PO_4$, 43.75 mM glycine), chosen to enable suitable buffering over a broad pH range, ranging from pH 4.0 to pH 9.0 and incubated at 25° C. for 15 min.

To determine the effect of temperature, 10 µM SnoopTag-MBP and 10 µM SnoopCatcher were mixed for 15 min at the indicated temperatures in phosphate buffered saline (PBS, 10 mM $Na_2HPO_4$ 137 mM NaCl, 27 mM KCl, 1.8 mM $KH_2PO_4$) pH 8.0 containing 1.5 M TMAO. PBS was used in place of TBS because the pH of Tris buffers changes substantially with temperature.

To investigate the sensitivity to the buffer composition, proteins were incubated at 25° C. for 15 min in PBS pH 8.0, TBS pH 8.0 or TBS pH 8.0 containing 1% Triton X-100 (w/v), 1% Tween 20 (v/v), 10 mM ethylene diamine tetraacetate (EDTA), 10 mM $MgCl_2$, 10 mM DTT or 50 mM Tris pH 8.0 with 1 M NaCl.

Reaction rate was determined by reacting SnoopTag-MBP and SnoopCatcher at the indicated concentrations in TBS pH 8.0 containing 1.5 M TMAO and incubating at 25° C. for various times. Reactions were stopped in SDS-loading buffer, as described above, prior to SDS-PAGE. % reconstitution was calculated as 100× the band intensity of the covalent adduct, divided by the sum of band intensities of SnoopTag-MBP, SnoopCatcher and the covalent adduct.

To test reversibility with competing tag, 10 µM SnoopCatcher was incubated with 15 µM SnoopTag-MBP for 6 hr and then SnoopTag-Affi-SpyTag at a final concentration of 130 µM was added for 16 hr, all at 25° C. To test reversibility with ammonia, 10 µM SnoopCatcher was incubated with 10 µM SnoopTag-MBP for 2 hr in TBS pH 8.0 containing 1.5 M TMAO and then TBS pH 8.0 or $NH_4Cl$ pH 9.0 (to a final concentration of 1 M) was added for 16 hr, all at 25° C.

Mass Spectrometry

20 µM SnoopTag-MBP and 20 µM SnoopCatcher were incubated at 25° C. for 2 hr in PBS pH 7.4. Mass spectrometry analysis was performed using a Micromass LCT time-of-flight electrospray ionization MS (Micromass) and m/z spectrum was converted to molecular mass profile using a maximum entropy algorithm and the V4.00.00 software (Waters). ExPASy ProtParam was used to predict the molecular masses based on the protein's amino acid sequence, with the N-terminal fMet cleaved and subtracting 17.0 Da for isopeptide bond formation. Non-enzymatic gluconylation is often observed from expression of His-tagged proteins in E. coli and adds 178 Da. Similarly, E. coli-expressed proteins may also undergo some degree of acetylation.

The decamer was concentrated to 15 µM and buffer-exchanged into 200 mM ammonium acetate using an Amicon Ultra 0.5 mL centrifugal filter with a 10 kDa cut-off (Millipore). Measurements were carried out on a first generation Synapt High Definition Mass Spectrometry Quadrupole Time of Flight mass spectrometer (Waters), calibrated using 10 mg/mL caesium iodide in 250 mM ammonium acetate. 2.5 µL aliquots of sample were delivered by nano-electrospray ionization via gold-coated capillaries, prepared in house. Instrumental parameters were as follows: source pressure 6.0 mbar, capillary voltage 1.20 kV, cone voltage 150 V, trap energy 30 V, transfer energy 10 V, bias voltage 5 V, and trap pressure 0.0163 mbar. Mass spectra were smoothed and peak-centered and masses were assigned using MassLynx v4.1 (Waters).

Solid-Phase Synthesis of Fusion Proteins

40 µL of slurry amylose resin (NEB) was applied to a 1 mL poly-prep column (Bio-Rad), rinsed with 1 mL MilliQ water and equilibrated with 1 mL TBS pH 8.0. 320 pmol tandem MBPx-SpyCatcher in TBS pH 8.0 in a final volume of 80 µL was added to the resin and incubated at 25° C. for 1 hr with 700 rpm shaking on a ThermoMixer comfort (Eppendorf). Unreacted protein was removed from the column by gravity flow and resin was washed with 1 mL Wash Buffer (50 mM Tris HCl pH 8.0 with 500 mM NaCl). 3 nmol SnoopTag-Affi-SpyTag in TBS pH 8.0 in a final volume of 80 µL was added to the resin and incubated at 25° C. for 1 hr with 700 rpm shaking. Unreacted SnoopTag-Affi-SpyTag was removed from the column by gravity flow and resin washed with 1 mL Wash Buffer. 4 nmol SpyCatcher-SnoopCatcher in TBS pH 8.0 with 1.5 M TMAO was added to the resin and incubated at 25° C. for 2 hr with 700 rpm shaking. Unreacted SpyCatcher-SnoopCatcher was removed from the column by gravity flow and the resin was washed with 1 mL Wash Buffer. Chains were produced by sequential addition of SnoopTag-Affi-SpyTag and SpyCatcher-SnoopCatcher, according to the conditions described above. Chains were eluted, after resin washing, by adding 40 µL TBS pH 8.0 containing 50 mM D-maltose (Sigma) and incubating at 25° C. for 10 min with 700 rpm shaking. Chains were collected by centrifuging the column in a 1.5 mL microcentrifuge tube for 10 s at 17,000 g. Chains containing SnoopTag-mEGFP-SpyTag and SnoopTag-SpyTag-Affi3 were synthesized in exactly the same way.

For SDS-PAGE testing after each step, samples were eluted as previously described, mixed with 6×SDS loading buffer and heated at 95° C. for 5 min before SDS-PAGE.

For biotinylated-SpyCatcher-based assembly, 40 µL of slurry monomeric avidin resin (Thermo Scientific) was applied to a 1 mL poly-prep column, rinsed and equilibrated as above. 4 µM biotinylated-SpyCatcher in TBS pH 8.0 in a final volume of 80 µL was added to the resin and incubated at 25° C. for 1 hr with 700 rpm shaking. Unreacted biotinylated-SpyCatcher was removed from the column by gravity flow, resin was washed with 1 mL Wash Buffer, and sequential addition of SnoopTag-Affi-SpyTag and SpyCatcher-SnoopCatcher was performed as described above.

After resin washing, chains were eluted by applying onto the column 40 µL 1 mM D-biotin in TBS pH 8.0 and incubating at 25° C. for 4 hr with 700 rpm shaking. Chains were collected as previously indicated and analyzed by SDS-PAGE on 16 and 8% Tris-glycine gels.

Gel Filtration Chromatography

Decamer chains were analyzed by gel filtration chromatography on a Superdex 200 GL 10/300 column (24 mL bed volume) (GE Healthcare). The column was calibrated by using gel filtration standards (thyroglobulin 670 kDa, IgG 158 kDa, ovalbumin 44 kDa, myoglobin 17 kDa, and vitamin B12 1.35 kDa) (Bio-Rad). Samples were eluted at 0.4 mL/min in 50 mM Tris HCl pH 8.0 with 500 mM NaCl, with absorbance profile measured at 280 nm on an ÄKTA purifier 10 (GE Healthcare).

Stability Testing of Chains

For temperature-stability testing, decamer chains in 150 mM ammonium acetate pH 8.0 at 3 µM in a final volume of 30 µL were incubated at 25, 37, 50, 60 or 70° C. for 3 min and cooled to 10° C. at 3° C./s in a Bio-Rad C1000 Thermal Cycler. Samples were then spun at 17,000 g at 4° C. for 30 min to remove aggregates and the supernatant was analyzed by SDS-PAGE with Coomassie staining on an 8% Tris-glycine gel. For time-dependent stability testing, decamer chains at 3 µM in 150 mM ammonium acetate pH 8.0 containing 0.1% sodium azide, 1 mM phenylmethylsulfonyl fluoride (PMSF), 1 mM EDTA, and EDTA-free mixed protease inhibitors (Roche) in a final volume of 30 µL were incubated at 25° C. for 1 or 4 days. At each time point samples were spun at 17,000 g at 4° C. for 30 min and the supernatant was analyzed by SDS-PAGE with Coomassie staining on an 8% Tris-glycine gel.

The invention claimed is:

1. A method of producing a fusion protein, said method comprising:
   a) contacting a first protein with a second protein under conditions that enable the formation of an isopeptide bond between said proteins, wherein said first protein and said second protein each comprise a peptide linker, wherein said peptide linkers are a pair of peptide linkers which react to form an isopeptide bond that links said first protein to said second protein to form a linked protein; and
   b) contacting the linked protein from (a) with a third protein under conditions that enable the formation of an isopeptide bond between said third protein and said linked protein, wherein said third protein comprises a peptide linker which reacts with a further peptide linker in the linked protein from (a), and wherein said peptide linkers are a pair of peptide linkers that react to form an isopeptide bond that links said third protein to said linked protein to form a fusion protein,
   wherein said pair of peptide linkers used in (a) are orthogonal to the pair of peptide linkers used in (b) and wherein the orthogonal pairs of peptide linkers are selected from:
   (1) a first peptide linker comprising the amino acid sequence of SEQ ID NO: 1 or a sequence with at least 70% sequence identity to the amino acid sequence of SEQ ID NO: 1, wherein said amino acid sequence comprises a lysine residue at position 9, wherein said peptide linker has 6-50 amino acids and a second peptide linker comprising the amino acid sequence of SEQ ID NO: 2 or a sequence with at least 70% sequence identity to the amino acid sequence of SEQ ID NO: 2, wherein said amino acid sequence comprises a glutamate or aspartate residue at position 55, a threonine residue at position 94, a glycine residue at position 100 and an asparagine or aspartate residue at position 106, wherein said peptide linker has 50-200 amino acids;
   (2) a first peptide linker comprising the amino acid sequence of SEQ ID NO: 5 or a sequence with at least 70% sequence identity to the amino acid sequence of SEQ ID NO: 5, wherein said amino acid sequence comprises an aspartate or asparagine residue at position 8, wherein said peptide linker has 6-50 amino acids and a second peptide linker comprising the amino acid sequence of SEQ ID NO: 6 or a sequence with at least 70% sequence identity to the amino acid sequence of SEQ ID NO: 6, wherein said amino acid sequence comprises a lysine residue at position 8, wherein said peptide linker has 50-200 amino acids;
   (3) a first peptide linker comprising the amino acid sequence of SEQ ID NO: 9 or a sequence with at least 70% sequence identity to the amino acid sequence of SEQ ID NO: 9, wherein said amino acid sequence comprises a threonine residue at position 5, an asparagine or aspartate residue at position 17 and wherein said peptide linker has 6-50 amino acids and a second peptide linker the amino acid sequence of SEQ ID NO: 10 or a sequence with at least 70% sequence identity to the amino acid sequence of SEQ ID NO: 10, wherein said amino acid sequence comprises a lysine residue at position 9 and a glutamate or aspartate residue at position 70, wherein said peptide linker has 50-200 amino acids; and
   (4) a first peptide linker comprising the amino acid sequence of SEQ ID NO: 109 or a sequence with at least 70% sequence identity to the amino acid sequence of SEQ ID NO: 109, wherein said amino acid sequence comprises an asparagine or aspartate residue at position 17, a glycine residue at position 11 and, wherein said peptide linker has 6-50 amino acids and a second peptide linker the amino acid sequence of SEQ ID NO: 10 or a sequence with at least 70% sequence identity to the amino acid sequence of SEQ ID NO: 10, wherein said amino acid sequence comprises a lysine residue at position 9 and a glutamate or aspartate residue at position 70, wherein said peptide linker has 50-200 amino acids.

2. The method of claim 1, being a method of producing a fusion protein, said method comprising:

a) providing a first protein comprising a first peptide linker;
b) contacting said first protein with a second protein, wherein said second protein comprises a second peptide linker and a third peptide linker, under conditions that enable said first peptide linker and said second peptide linker to form an isopeptide bond, thereby linking said first and second proteins; and
c) contacting said linked first and second proteins with a third protein, wherein said third protein comprises a fourth peptide linker, under conditions that enable said third peptide linker and said fourth peptide linker to form an isopeptide bond, thereby linking said second and third proteins to produce a fusion protein,
wherein said first and second peptide linkers are a pair of peptide linkers that are orthogonal to the pair of peptide linkers consisting of said third and fourth peptide linkers.

3. The method of claim 1, wherein the method further comprises a step of extending the fusion protein, wherein the new protein to be linked to the fusion protein comprises a peptide linker that forms part of a pair of peptide linkers that is orthogonal to the pair of peptide linkers used to form the previous isopeptide bond in the fusion protein, wherein the peptide linker in the new protein is capable of forming an isopeptide bond with a peptide linker in a protein of the fusion protein, said method comprising contacting said new protein with said fusion protein under conditions that enable said new protein to form an isopeptide bond with a peptide linker in the fusion protein.

4. The method of claim 1, wherein said method is performed on a solid phase, optionally further comprising a step of eluting the fusion protein from the solid phase.

5. A peptide linker comprising:
(i) the amino acid sequence of SEQ ID NO: 1 or a sequence with at least 70% sequence identity to the amino acid sequence of SEQ ID NO: 1, wherein said amino acid sequence comprises a lysine residue at position 9, wherein said peptide linker has 6-50 amino acids and is: (a) conjugated to another molecule or a substrate; and/or (b) a non-naturally occurring peptide;
(ii) the amino acid sequence of SEQ ID NO: 2 or a sequence with at least 70% sequence identity to the amino acid sequence of SEQ ID NO: 2, wherein said amino acid sequence comprises a glutamate or aspartate residue at position 55, a threonine residue at position 94, a glycine residue at position 100 and an asparagine or aspartate residue at position 106, wherein said peptide linker has 50-200 amino acids;
(iii) the amino acid sequence of SEQ ID NO: 5 or a sequence with at least 70% sequence identity to the amino acid sequence of SEQ ID NO: 5, wherein said amino acid sequence comprises an aspartate or asparagine residue at position 8, wherein said peptide linker has 6-50 amino acids and is: (a) conjugated to another molecule or a substrate; and/or (b) a non-naturally occurring peptide;
(iv) the amino acid sequence of SEQ ID NO: 6 or a sequence with at least 70% sequence identity to the amino acid sequence of SEQ ID NO: 6, wherein said amino acid sequence comprises a lysine residue at position 8, wherein said peptide linker has 50-200 amino acids and is: (a) conjugated to another molecule or a substrate; and/or (b) a non-naturally occurring peptide;
(v) the amino acid sequence as set forth in SEQ ID NO: 9 or a sequence with at least 70% sequence identity to the amino acid sequence of SEQ ID NO: 9, wherein said amino acid sequence comprises a threonine residue at position 5, an asparagine or aspartate residue at position 17 and wherein said peptide linker has 6-50 amino acids;
(vi) the amino acid sequence of SEQ ID NO: 10 or a sequence with at least 70% sequence identity to the amino acid sequence of SEQ ID NO: 10, wherein said amino acid sequence comprises a lysine residue at position 9 and a glutamate or aspartate residue at position 70, wherein said peptide linker has 50-200 amino acids and is: (a) conjugated to another molecule or a substrate; and/or (b) non-naturally occurring peptide; or
(vii) the amino acid sequence of SEQ ID NO: 109 or a sequence with at least 70% sequence identity to the amino acid sequence of SEQ ID NO: 109, wherein said amino acid sequence comprises an asparagine or aspartate residue at position 17, a glycine residue at position 11 and, wherein said peptide linker has 6-50 amino acids.

6. The peptide linker of claim 5, wherein the peptide linker is conjugated to another molecule or a substrate.

7. The peptide linker of claim 6, wherein the molecule is a peptide or protein.

8. The peptide linker of claim 7, wherein the peptide linker is conjugated to the protein or peptide directly.

9. The peptide linker of claim 7, wherein the peptide or protein is an enzyme, structural protein, antibody, antigen, prion, receptor, ligand, cytokine, chemokine, hormone or any combination thereof.

10. The peptide linker of claim 6, wherein the substrate is a particle, sheet, gel, filter, membrane, fibre, capillary, slide, array, microtitre strip, tube, plate or well.

11. The peptide linker of claim 6, wherein the substrate is glass, silica, latex or a polymeric material.

12. The peptide linker of claim 5, wherein the peptide linker is conjugated to a member selected from a nucleic acid molecule, protein, peptide, antibody, small-molecule organic compound, fluorophore, metal-ligand complex, polysaccharide, nanoparticle, nanotube, polymer or a combination thereof.

13. The peptide linker of claim 5, wherein the peptide linker is conjugated to a member selected from an antibiotic, an anti-viral agent, a vaccine, an anti-tumor agent, a radioisotope, a fluorescent label, a luminescent label, a chromophore label, an enzyme, an enzyme substrate, a magnetic resonance imaging label, a positron emission tomography probe, boron 10, and a hexahistadine tag.

14. A pair of peptide linkers comprising:
(1) a first peptide linker comprising the amino acid sequence of SEQ ID NO: 1 or a sequence with at least 70% sequence identity to the amino acid sequence of SEQ ID NO: 1, wherein said amino acid sequence comprises a lysine residue at position 9, wherein said peptide linker has 6-50 amino acids, and a second peptide linker comprising the amino acid sequence of SEQ ID NO: 2 or a sequence with at least 70% sequence identity to the amino acid sequence of SEQ ID NO: 2, wherein said amino acid sequence comprises a glutamate or aspartate residue at position 55, a threonine residue at position 94, a glycine residue at position 100 and an asparagine or aspartate residue at position 106, wherein said peptide linker has 50-200 amino acids;
(2) a first peptide linker comprising the amino acid sequence of SEQ ID NO: 5 or a sequence with at least 70% sequence identity to the amino acid sequence of SEQ ID NO: 5, wherein said amino acid sequence comprises an aspartate or asparagine residue at position 8, wherein said peptide linker has 6-50 amino acids and a second peptide linker comprising the amino acid sequence of SEQ ID NO: 6 or a sequence with at least 70% sequence identity to the amino acid sequence of SEQ ID NO: 6, wherein said amino acid sequence comprises a lysine residue at position 8, wherein said peptide linker has 50-200 amino acids;

(3) a first peptide linker comprising the amino acid sequence of SEQ ID NO: 9 or a sequence with at least 70% sequence identity to the amino acid sequence of SEQ ID NO: 9, wherein said amino acid sequence comprises a threonine residue at position 5, an asparagine or aspartate residue at position 17 and wherein said peptide linker has 6-50 amino acids and a second peptide linker comprising the amino acid sequence of SEQ ID NO: 10 or a sequence with at least 70% sequence identity to the amino acid sequence of SEQ ID NO: 10, wherein said amino acid sequence comprises a lysine residue at position 9 and a glutamate or aspartate residue at position 70, wherein said peptide linker has 50-200 amino acids; or (4) a first peptide linker comprising the amino acid sequence of SEQ ID NO: 109 or a sequence with at least 70% sequence identity to the amino acid sequence of SEQ ID NO: 109, wherein said amino acid sequence comprises an asparagine or aspartate residue at position 17, a glycine residue at position 11 and, wherein said peptide linker has 6-50 amino acids and a second peptide linker the amino acid sequence of SEQ ID NO: 10 or a sequence with at least 70% sequence identity to the amino acid sequence of SEQ ID NO: 10, wherein said amino acid sequence comprises a lysine residue at position 9 and a glutamate or aspartate residue at position 70, wherein said peptide linker has 50-200 amino acids.

15. The pair of peptide linkers of claim 14, wherein at least one peptide linker in the pair is conjugated to another molecule or a substrate.

16. The pair of peptide linkers of claim 14, wherein at least one peptide linker in the pair is a non-naturally occurring peptide.

* * * * *